(12) United States Patent
Goldfarb et al.

(10) Patent No.: US 12,121,231 B2
(45) Date of Patent: Oct. 22, 2024

(54) METHODS AND DEVICES FOR TISSUE GRASPING AND ASSESSMENT

(71) Applicant: EVALVE, INC., Santa Clara, CA (US)

(72) Inventors: Eric A. Goldfarb, San Francisco, CA (US); Troy L. Thornton, San Francisco, CA (US); Alfred H. Raschdorf, St. James, NY (US); Jaime E. Sarabia, Mableton, GA (US); John P. Madden, Palo Alto, CA (US); Ferolyn T. Powell, San Francisco, CA (US); Brian B. Martin, Boulder Creek, CA (US); Sylvia Erickson, San Carlos, CA (US); Jan Komtebedde, Los Gatos, CA (US); Yen C. Liao, San Mateo, CA (US)

(73) Assignee: EVALVE, INC., Santa Clara, CA (US)

( * ) Notice: Subject to any disclaimer, the term of this patent is extended or adjusted under 35 U.S.C. 154(b) by 227 days.

(21) Appl. No.: 17/723,402

(22) Filed: Apr. 18, 2022

(65) Prior Publication Data
US 2022/0240920 A1 Aug. 4, 2022

Related U.S. Application Data

(60) Continuation of application No. 16/912,361, filed on Jun. 25, 2020, now Pat. No. 11,304,715, which is a
(Continued)

(51) Int. Cl.
*A61B 17/29* (2006.01)
*A61B 17/00* (2006.01)
(Continued)

(52) U.S. Cl.
CPC .......... *A61B 17/0401* (2013.01); *A61B 17/08* (2013.01); *A61B 17/29* (2013.01); *A61B 2017/00243* (2013.01); *A61B 2017/00783* (2013.01); *A61B 2017/081* (2013.01); *A61B 2017/22088* (2013.01);
(Continued)

(58) Field of Classification Search
CPC ............................. A61F 2/2487; A61F 2/2478
See application file for complete search history.

(56) References Cited

U.S. PATENT DOCUMENTS 2,097,018 A 10/1937 Chamberlain
2,108,206 A 2/1938 Meeker
(Continued)

FOREIGN PATENT DOCUMENTS

DE 3504292 C1 7/1986
EP 0 179 562 B1 7/1989
(Continued)

OTHER PUBLICATIONS

U.S. Appl. No. 11/237,213 (U.S. Pat. No. 7,635,329), filed Sep. 27, 2005 (Dec. 22, 2009).
(Continued)

*Primary Examiner* — Jacqueline Woznicki
(74) *Attorney, Agent, or Firm* — SLEMAN & LUND LLP

(57) ABSTRACT

Devices, systems and methods are provided for stabilizing and grasping tissues such as valve leaflets, assessing the grasp of these tissues, approximating and fixating the tissues, and assessing the fixation of the tissues to treat cardiac valve regurgitation, particularly mitral valve regurgitation.

17 Claims, 38 Drawing Sheets

Related U.S. Application Data continuation of application No. 16/279,523, filed on Feb. 19, 2019, now Pat. No. 11,484,331, which is a continuation of application No. 14/070,936, filed on Nov. 4, 2013, now abandoned, which is a continuation of application No. 13/239,514, filed on Sep. 22, 2011, now abandoned, which is a continuation of application No. 12/575,100, filed on Oct. 7, 2009, now Pat. No. 8,052,592, which is a division of application No. 11/237,213, filed on Sep. 27, 2005, now Pat. No. 7,635,329.

(60) Provisional application No. 60/613,867, filed on Sep. 27, 2004.

(51) Int. Cl.
*A61B 17/04* (2006.01)
*A61B 17/08* (2006.01)
*A61B 17/28* (2006.01)
*A61B 90/00* (2016.01)
*A61F 2/24* (2006.01)
*A61B 17/22* (2006.01)
*A61B 17/30* (2006.01)
*A61B 17/34* (2006.01)

(52) U.S. Cl.
CPC ............... *A61B 2017/22089* (2013.01); *A61B 2017/22098* (2013.01); *A61B 2017/2825* (2013.01); *A61B 2017/2926* (2013.01); *A61B 2017/2931* (2013.01); *A61B 2017/306* (2013.01); *A61B 17/3478* (2013.01); *A61B 2090/3908* (2016.02); *A61B 2090/3925* (2016.02); *A61F 2/2478* (2013.01); *A61F 2/2487* (2013.01); *A61F 2210/0014* (2013.01); *A61F 2220/0016* (2013.01); *A61F 2230/001* (2013.01)

(56) References Cited

U.S. PATENT DOCUMENTS

| | | |
|---|---|---|
| 3,296,668 A | 1/1967 | Aiken |
| 3,378,010 A | 4/1968 | Codling et al. |
| 3,671,979 A | 6/1972 | Moulopoulos |
| 3,779,108 A | 12/1973 | Reiter |
| 3,874,338 A | 4/1975 | Happel |
| 3,874,388 A | 4/1975 | King et al. |
| 4,007,743 A | 2/1977 | Blake |
| 4,056,854 A | 11/1977 | Boretos et al. |
| 4,064,881 A | 12/1977 | Meredith |
| 4,112,951 A | 9/1978 | Hulka et al. |
| 4,235,238 A | 11/1980 | Ogiu et al. |
| 4,297,749 A | 11/1981 | Davis et al. |
| 4,425,908 A | 1/1984 | Simon |
| 4,484,579 A | 11/1984 | Meno et al. |
| 4,487,205 A | 12/1984 | Di Giovanni et al. |
| 4,498,476 A | 2/1985 | Cerwin et al. |
| 4,510,934 A | 4/1985 | Batra |
| 4,578,061 A | 3/1986 | Lemelson |
| 4,641,366 A | 2/1987 | Yokoyama et al. |
| 4,686,965 A | 8/1987 | Bonnet et al. |
| 4,691,674 A | 9/1987 | Otsuka et al. |
| 4,700,179 A | 10/1987 | Fancher |
| 4,710,727 A | 12/1987 | Rutt |
| 4,777,951 A | 10/1988 | Cribier et al. |
| 4,809,695 A | 3/1989 | Gwathmey et al. |
| 4,850,358 A | 7/1989 | Millar |
| 4,917,089 A | 4/1990 | Sideris |
| 4,944,295 A | 7/1990 | Gwathmey et al. |
| 4,969,890 A | 11/1990 | Sugita et al. |
| 4,994,077 A | 2/1991 | Dobben |
| 5,015,249 A | 5/1991 | Nakao et al. |
| 5,019,096 A | 5/1991 | Fox, Jr. et al. |
| 5,042,707 A | 8/1991 | Taheri |
| 5,047,041 A | 9/1991 | Samuels |
| 5,049,153 A | 9/1991 | Nakao et al. |
| 5,052,407 A | 10/1991 | Hauser et al. |
| 5,061,277 A | 10/1991 | Carpentier et al. |
| 5,069,679 A | 12/1991 | Taheri |
| 5,080,179 A | 1/1992 | Gien et al. |
| 5,090,558 A | 2/1992 | Hatouchi |
| 5,100,684 A | 3/1992 | El-Nokaly et al. |
| 5,108,368 A | 4/1992 | Hammerslag et al. |
| 5,125,758 A | 6/1992 | DeWan |
| 5,171,252 A | 12/1992 | Friedland |
| 5,171,259 A | 12/1992 | Inoue |
| 5,190,554 A | 3/1993 | Coddington et al. |
| 5,195,968 A | 3/1993 | Lundquist et al. |
| 5,209,756 A | 5/1993 | Seedhom et al. |
| 5,226,429 A | 7/1993 | Kuzmak |
| 5,226,911 A | 7/1993 | Chee et al. |
| 5,234,437 A | 8/1993 | Sepetka |
| 5,250,071 A | 10/1993 | Palermo |
| 5,251,611 A | 10/1993 | Zehel et al. |
| 5,254,130 A | 10/1993 | Poncet et al. |
| 5,261,916 A | 11/1993 | Engelson |
| 5,275,578 A | 1/1994 | Adams |
| 5,282,845 A | 2/1994 | Bush et al. |
| 5,304,131 A | 4/1994 | Paskar |
| 5,306,283 A | 4/1994 | Conners |
| 5,306,286 A | 4/1994 | Stack et al. |
| 5,312,415 A | 5/1994 | Palermo |
| 5,314,424 A | 5/1994 | Nicholas |
| 5,318,525 A | 6/1994 | West et al. |
| 5,320,632 A | 6/1994 | Heidmueller |
| 5,325,845 A | 7/1994 | Adair |
| 5,327,891 A | 7/1994 | Rammler |
| 5,330,442 A | 7/1994 | Green et al. |
| 5,332,402 A | 7/1994 | Teitelbaum |
| 5,348,536 A | 9/1994 | Young |
| 5,350,397 A | 9/1994 | Palermo et al. |
| 5,350,399 A | 9/1994 | Erlebacher et al. |
| 5,359,994 A | 11/1994 | Kreuter et al. |
| 5,364,352 A | 11/1994 | Cimino et al. |
| 5,368,564 A | 11/1994 | Savage |
| 5,368,601 A | 11/1994 | Sauer et al. |
| 5,383,886 A | 1/1995 | Kensey et al. |
| 5,403,291 A | 4/1995 | Abrahamson |
| 5,403,312 A | 4/1995 | Yates et al. |
| 5,403,326 A | 4/1995 | Harrison et al. |
| 5,411,552 A | 5/1995 | Andersen et al. |
| 5,417,699 A | 5/1995 | Klein et al. |
| 5,417,700 A | 5/1995 | Egan |
| 5,423,857 A | 6/1995 | Rosenman et al. |
| 5,423,858 A | 6/1995 | Bolanos et al. |
| 5,423,882 A | 6/1995 | Jackman et al. |
| 5,431,666 A | 7/1995 | Sauer et al. |
| 5,437,551 A | 8/1995 | Chalifoux |
| 5,437,681 A | 8/1995 | Meade et al. |
| 5,447,966 A | 9/1995 | Hermes et al. |
| 5,450,860 A | 9/1995 | O'Connor |
| 5,456,400 A | 10/1995 | Shichman et al. |
| 5,456,684 A | 10/1995 | Schmidt et al. |
| 5,462,527 A | 10/1995 | Stevens-Wright et al. |
| 5,472,044 A | 12/1995 | Hall et al. |
| 5,476,470 A | 12/1995 | Fitzgibbons, Jr. |
| 5,477,856 A | 12/1995 | Lundquist |
| 5,478,309 A | 12/1995 | Sweezer et al. |
| 5,478,353 A | 12/1995 | Yoon |
| 5,487,746 A | 1/1996 | Yu et al. |
| 5,507,725 A | 4/1996 | Savage et al. |
| 5,507,757 A | 4/1996 | Sauer et al. |
| 5,520,701 A | 5/1996 | Lerch |
| 5,522,873 A | 6/1996 | Jackman et al. |
| 5,527,313 A | 6/1996 | Scott et al. |
| 5,527,321 A | 6/1996 | Hinchliffe |
| 5,527,322 A | 6/1996 | Klein et al. |
| 5,536,251 A | 7/1996 | Evard et al. |
| 5,538,504 A | 7/1996 | Linden et al. |
| 5,540,705 A | 7/1996 | Meade et al. |
| 5,542,949 A | 8/1996 | Yoon |

(56) References Cited

U.S. PATENT DOCUMENTS

| | | |
|---|---|---|
| 5,554,185 A | 9/1996 | Block et al. |
| 5,562,678 A | 10/1996 | Booker |
| 5,569,274 A | 10/1996 | Rapacki et al. |
| 5,571,085 A | 11/1996 | Accisano, III |
| 5,571,137 A | 11/1996 | Marlow et al. |
| 5,571,215 A | 11/1996 | Sterman et al. |
| 5,575,802 A | 11/1996 | McQuilkin et al. |
| 5,582,611 A | 12/1996 | Tsuruta et al. |
| 5,584,803 A | 12/1996 | Stevens et al. |
| 5,593,424 A | 1/1997 | Northrup, III |
| 5,593,435 A | 1/1997 | Carpentier et al. |
| 5,609,598 A | 3/1997 | Laufer et al. |
| 5,618,306 A | 4/1997 | Roth et al. |
| 5,620,452 A | 4/1997 | Yoon |
| 5,626,588 A | 5/1997 | Sauer et al. |
| 5,634,932 A | 6/1997 | Schmidt |
| 5,636,634 A | 6/1997 | Kordis et al. |
| 5,639,277 A | 6/1997 | Mariant et al. |
| 5,640,955 A | 6/1997 | Ockuly et al. |
| 5,649,937 A | 7/1997 | Bito et al. |
| 5,662,681 A | 9/1997 | Nash et al. |
| 5,669,917 A | 9/1997 | Sauer et al. |
| 5,690,671 A | 11/1997 | McGurk et al. |
| 5,695,504 A | 12/1997 | Gifford, III et al. |
| 5,695,505 A | 12/1997 | Yoon |
| 5,702,825 A | 12/1997 | Keital et al. |
| 5,706,824 A | 1/1998 | Whittier |
| 5,709,707 A | 1/1998 | Lock et al. |
| 5,713,910 A | 2/1998 | Gordon et al. |
| 5,713,911 A | 2/1998 | Racene et al. |
| 5,715,817 A | 2/1998 | Stevens-Wright et al. |
| 5,716,367 A | 2/1998 | Koike et al. |
| 5,718,725 A | 2/1998 | Sterman |
| 5,719,725 A | 2/1998 | Nakao |
| 5,722,421 A | 3/1998 | Francese et al. |
| 5,725,542 A | 3/1998 | Yoon |
| 5,725,556 A | 3/1998 | Moser et al. |
| 5,738,649 A | 4/1998 | Macoviak |
| 5,741,280 A | 4/1998 | Fleenor |
| 5,749,828 A | 5/1998 | Solomon et al. |
| 5,769,812 A | 6/1998 | Stevens et al. |
| 5,769,863 A | 6/1998 | Garrison |
| 5,772,578 A | 6/1998 | Heimberger et al. |
| 5,782,845 A | 7/1998 | Shewchuk |
| 5,797,927 A | 8/1998 | Yoon |
| 5,797,960 A | 8/1998 | Stevens et al. |
| 5,801,999 A | 9/1998 | Satou et al. |
| 5,810,724 A | 9/1998 | Gronvall |
| 5,810,847 A | 9/1998 | Laufer et al. |
| 5,810,849 A | 9/1998 | Kontos |
| 5,810,853 A | 9/1998 | Yoon |
| 5,810,876 A | 9/1998 | Kelleher |
| 5,814,029 A | 9/1998 | Hassett |
| 5,820,592 A | 10/1998 | Hammerslag |
| 5,820,631 A | 10/1998 | Nobles |
| 5,823,955 A | 10/1998 | Kuck et al. |
| 5,823,956 A | 10/1998 | Roth et al. |
| 5,824,065 A | 10/1998 | Gross |
| 5,827,237 A | 10/1998 | Macoviak et al. |
| 5,829,447 A | 11/1998 | Stevens et al. |
| 5,833,671 A | 11/1998 | Macoviak et al. |
| 5,836,955 A | 11/1998 | Buelna et al. |
| 5,840,081 A | 11/1998 | Anderson et al. |
| 5,843,031 A | 12/1998 | Hermann et al. |
| 5,843,167 A | 12/1998 | Dwyer et al. |
| 5,849,019 A | 12/1998 | Yoon |
| 5,853,422 A | 12/1998 | Huebsch et al. |
| 5,855,271 A | 1/1999 | Eubanks et al. |
| 5,855,614 A | 1/1999 | Stevens et al. |
| 5,860,990 A | 1/1999 | Nobles et al. |
| 5,868,733 A | 2/1999 | Ockuly et al. |
| 5,876,399 A | 3/1999 | Chia et al. |
| 5,879,307 A | 3/1999 | Chio et al. |
| 5,885,271 A | 3/1999 | Hamilton et al. |
| 5,891,160 A | 4/1999 | Williamson, IV et al. |
| 5,904,703 A | 5/1999 | Gilson |
| 5,916,147 A | 6/1999 | Boury |
| 5,928,224 A | 7/1999 | Laufer |
| 5,944,733 A | 8/1999 | Engelson |
| 5,947,363 A | 9/1999 | Bolduc et al. |
| 5,954,732 A | 9/1999 | Hart et al. |
| 5,957,949 A | 9/1999 | Leonhardt et al. |
| 5,964,223 A | 10/1999 | Baran |
| 5,972,020 A | 10/1999 | Carpentier et al. |
| 5,972,030 A | 10/1999 | Garrison et al. |
| 5,980,455 A | 11/1999 | Daniel et al. |
| 5,989,284 A | 11/1999 | Laufer |
| 6,010,516 A | 1/2000 | Hulka |
| 6,015,417 A | 1/2000 | Reynolds, Jr. |
| 6,019,722 A | 2/2000 | Spence et al. |
| 6,022,360 A | 2/2000 | Reimels et al. |
| 6,033,378 A | 3/2000 | Lundquist et al. |
| 6,036,699 A | 3/2000 | Andreas et al. |
| 6,048,351 A | 4/2000 | Gordon et al. |
| 6,059,757 A | 5/2000 | Macoviak et al. |
| 6,060,628 A | 5/2000 | Aoyama et al. |
| 6,060,629 A | 5/2000 | Pham et al. |
| 6,063,106 A | 5/2000 | Gibson |
| 6,066,146 A | 5/2000 | Carroll et al. |
| 6,068,628 A | 5/2000 | Fanton et al. |
| 6,068,629 A | 5/2000 | Haissaguerre et al. |
| 6,077,214 A | 6/2000 | Mortier et al. |
| 6,086,600 A | 7/2000 | Kortenbach |
| 6,088,889 A | 7/2000 | Luther et al. |
| 6,099,553 A | 8/2000 | Hart et al. |
| 6,102,887 A | 8/2000 | Altman |
| 6,110,145 A | 8/2000 | Macoviak |
| 6,117,144 A | 9/2000 | Nobles et al. |
| 6,117,159 A | 9/2000 | Huebsch et al. |
| 6,123,699 A | 9/2000 | Webster, Jr. |
| 6,126,658 A | 10/2000 | Baker |
| 6,132,447 A | 10/2000 | Dorsey |
| 6,136,010 A | 10/2000 | Modesitt et al. |
| 6,143,024 A | 11/2000 | Campbell et al. |
| 6,159,240 A | 12/2000 | Sparer et al. |
| 6,162,233 A | 12/2000 | Williamson, IV et al. |
| 6,165,164 A | 12/2000 | Hill et al. |
| 6,165,183 A | 12/2000 | Kuehn et al. |
| 6,165,204 A | 12/2000 | Levinson et al. |
| 6,168,614 B1 | 1/2001 | Andersen et al. |
| 6,171,320 B1 | 1/2001 | Monassevitch |
| 6,174,322 B1 | 1/2001 | Schneidt |
| 6,182,664 B1 | 2/2001 | Cosgrove |
| 6,187,003 B1 | 2/2001 | Buysse et al. |
| 6,190,408 B1 | 2/2001 | Melvin |
| 6,203,531 B1 | 3/2001 | Ockuly et al. |
| 6,203,553 B1 | 3/2001 | Robertson et al. |
| 6,206,893 B1 | 3/2001 | Klein et al. |
| 6,206,907 B1 | 3/2001 | Marino et al. |
| 6,210,419 B1 | 4/2001 | Mayenberger et al. |
| 6,210,432 B1 | 4/2001 | Solem et al. |
| 6,245,079 B1 | 6/2001 | Nobles et al. |
| 6,267,746 B1 | 7/2001 | Bumbalough |
| 6,267,781 B1 | 7/2001 | Tu |
| 6,269,534 B1 | 8/2001 | Mattmann et al. |
| 6,269,819 B1 | 8/2001 | Oz et al. |
| 6,277,555 B1 | 8/2001 | Duran et al. |
| 6,283,127 B1 | 9/2001 | Sterman et al. |
| 6,283,962 B1 | 9/2001 | Tu et al. |
| 6,299,637 B1 | 10/2001 | Shaolian et al. |
| 6,306,133 B1 | 10/2001 | Tu et al. |
| 6,312,447 B1 | 11/2001 | Grimes |
| 6,319,250 B1 | 11/2001 | Falwell et al. |
| 6,322,559 B1 | 11/2001 | Daulton et al. |
| 6,332,893 B1 | 12/2001 | Mortier et al. |
| 6,352,708 B1 | 3/2002 | Duran et al. |
| 6,355,030 B1 | 3/2002 | Aldrich et al. |
| 6,358,277 B1 | 3/2002 | Duran |
| 6,368,326 B1 | 4/2002 | Dakin et al. |
| 6,402,780 B2 | 6/2002 | Williamson et al. |
| 6,402,781 B1 | 6/2002 | Langberg et al. |
| 6,406,420 B1 | 6/2002 | McCarthy et al. |
| 6,419,669 B1 | 7/2002 | Frazier et al. |
| 6,461,366 B1 | 10/2002 | Seguin |

(56) References Cited

U.S. PATENT DOCUMENTS

| | | |
|---|---|---|
| 6,464,707 B1 | 10/2002 | Bjerken |
| 6,482,224 B1 | 11/2002 | Michler et al. |
| 6,485,489 B2 | 11/2002 | Teirstein et al. |
| 6,508,828 B1 | 1/2003 | Akerfeldt et al. |
| 6,533,796 B1 | 3/2003 | Sauer et al. |
| 6,537,314 B2 | 3/2003 | Langberg et al. |
| 6,540,755 B2 | 4/2003 | Ockuly et al. |
| 6,551,331 B2 | 4/2003 | Nobles et al. |
| 6,562,037 B2 | 5/2003 | Paton et al. |
| 6,562,052 B2 | 5/2003 | Nobles et al. |
| 6,575,971 B2 | 6/2003 | Hauck et al. |
| 6,582,451 B1 | 6/2003 | Marucci |
| 6,585,761 B2 | 7/2003 | Taheri |
| 6,599,311 B1 | 7/2003 | Biggs et al. |
| 6,616,684 B1 | 9/2003 | Vidlund et al. |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,641,592 B1 | 11/2003 | Sauer et al. |
| 6,656,221 B2 | 12/2003 | Taylor et al. |
| 6,669,687 B1 | 12/2003 | Saadat |
| 6,685,648 B2 | 2/2004 | Flaherty et al. |
| 6,689,164 B1 | 2/2004 | Seguin |
| 6,695,866 B1 | 2/2004 | Kuehn et al. |
| 6,701,929 B2 | 3/2004 | Hussein |
| 6,702,825 B2 | 3/2004 | Frazier et al. |
| 6,702,826 B2 | 3/2004 | Liddicoat et al. |
| 6,709,382 B1 | 3/2004 | Horner |
| 6,709,456 B2 | 3/2004 | Langberg et al. |
| 6,709,458 B2 | 3/2004 | Michelson |
| 6,712,836 B1 | 3/2004 | Berg |
| 6,718,985 B2 | 4/2004 | Hlavka et al. |
| 6,719,767 B1 | 4/2004 | Kimblad |
| 6,723,038 B1 | 4/2004 | Schroeder et al. |
| 6,726,716 B2 | 4/2004 | Marquez |
| 6,740,107 B2 | 5/2004 | Loeb et al. |
| 6,746,471 B2 | 6/2004 | Mortier et al. |
| 6,752,813 B2 | 6/2004 | Goldfarb et al. |
| 6,755,777 B2 | 6/2004 | Schweich et al. |
| 6,764,510 B2 | 7/2004 | Vidlund et al. |
| 6,767,349 B2 | 7/2004 | Ouchi |
| 6,770,083 B2 | 8/2004 | Seguin |
| 6,773,440 B2 | 8/2004 | Gannoe et al. |
| 6,797,001 B2 | 9/2004 | Mathis et al. |
| 6,797,002 B2 | 9/2004 | Spence et al. |
| 6,860,179 B2 | 3/2005 | Hopper et al. |
| 6,875,224 B2 | 4/2005 | Grimes |
| 6,926,715 B1 | 8/2005 | Hauck et al. |
| 6,945,978 B1 | 9/2005 | Hyde |
| 6,949,122 B2 | 9/2005 | Adams et al. |
| 6,966,914 B2 | 11/2005 | Abe |
| 6,986,775 B2 | 1/2006 | Morales et al. |
| 6,991,625 B1 | 1/2006 | Gately |
| 7,004,970 B2 | 2/2006 | Cauthen, III et al. |
| 7,011,669 B2 | 3/2006 | Kimblad |
| 7,048,754 B2 | 5/2006 | Martin et al. |
| 7,112,207 B2 | 9/2006 | Allen et al. |
| 7,226,467 B2 | 6/2007 | Lucatero et al. |
| 7,288,097 B2 | 10/2007 | Seguin |
| 7,381,210 B2 | 6/2008 | Zarbatany et al. |
| 7,464,712 B2 | 12/2008 | Oz et al. |
| 7,497,822 B1 | 3/2009 | Kugler et al. |
| 7,527,647 B2 | 5/2009 | Spence |
| 7,533,790 B1 | 5/2009 | Knodel et al. |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,604,646 B2 | 10/2009 | Goldfarb et al. |
| 7,608,091 B2 | 10/2009 | Goldfarb et al. |
| 7,635,329 B2 | 12/2009 | Goldfarb et al. |
| 7,938,827 B2 | 5/2011 | Hauck |
| 8,029,518 B2 | 10/2011 | Goldfarb |
| 8,216,230 B2 | 7/2012 | Hauck |
| 8,459,520 B2 | 6/2013 | Giordano et al. |
| 10,624,640 B2 | 4/2020 | Dell et al. |
| 10,653,427 B2 | 5/2020 | Goldfarb et al. |
| 2001/0004715 A1 | 6/2001 | Duran et al. |
| 2001/0005787 A1 | 6/2001 | Oz et al. |
| 2001/0018611 A1 | 8/2001 | Solem et al. |
| 2001/0022872 A1 | 9/2001 | Marui |
| 2001/0037084 A1 | 11/2001 | Nardeo |
| 2001/0039411 A1 | 11/2001 | Johansson et al. |
| 2001/0044568 A1 | 11/2001 | Langberg et al. |
| 2002/0013571 A1 | 1/2002 | Goldfarb et al. |
| 2002/0022848 A1 | 2/2002 | Garrison et al. |
| 2002/0026233 A1 | 2/2002 | Shaknovich |
| 2002/0035361 A1 | 3/2002 | Houser et al. |
| 2002/0035381 A1 | 3/2002 | Bardy et al. |
| 2002/0042651 A1 | 4/2002 | Liddicoat et al. |
| 2002/0055774 A1 | 5/2002 | Liddicoat |
| 2002/0055775 A1 | 5/2002 | Carpentier et al. |
| 2002/0058995 A1 | 5/2002 | Stevens |
| 2002/0077687 A1 | 6/2002 | Ahn |
| 2002/0087148 A1 | 7/2002 | Brock et al. |
| 2002/0087169 A1 | 7/2002 | Brock et al. |
| 2002/0087173 A1 | 7/2002 | Alferness et al. |
| 2002/0103532 A1 | 8/2002 | Langberg et al. |
| 2002/0107534 A1 | 8/2002 | Schaefer et al. |
| 2002/0123802 A1 | 9/2002 | Snyders |
| 2002/0147456 A1 | 10/2002 | Diduch et al. |
| 2002/0156526 A1 | 10/2002 | Hlavka et al. |
| 2002/0158528 A1 | 10/2002 | Tsuzaki et al. |
| 2002/0161378 A1 | 10/2002 | Downing |
| 2002/0169360 A1 | 11/2002 | Taylor et al. |
| 2002/0183766 A1 | 12/2002 | Seguin |
| 2002/0183835 A1 | 12/2002 | Taylor et al. |
| 2003/0012068 A1 | 1/2003 | Satani |
| 2003/0018329 A1 | 1/2003 | Hooven |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0074012 A1 | 4/2003 | Nguyen et al. |
| 2003/0078654 A1 | 4/2003 | Taylor et al. |
| 2003/0083742 A1 | 5/2003 | Spence et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0120341 A1 | 6/2003 | Shennib et al. |
| 2003/0130669 A1 | 7/2003 | Damarati |
| 2003/0130730 A1 | 7/2003 | Cohn et al. |
| 2003/0144623 A1 | 7/2003 | Heath |
| 2003/0144697 A1 | 7/2003 | Mathis et al. |
| 2003/0149463 A1 | 8/2003 | Solymar |
| 2003/0167071 A1 | 9/2003 | Martin et al. |
| 2003/0171776 A1 | 9/2003 | Adams et al. |
| 2003/0187467 A1 | 10/2003 | Schreck |
| 2003/0195562 A1 | 10/2003 | Collier et al. |
| 2003/0208231 A1 | 11/2003 | Williamson, IV et al. |
| 2003/0229395 A1 | 12/2003 | Cox |
| 2003/0233038 A1 | 12/2003 | Hassett |
| 2004/0002719 A1 | 1/2004 | Oz et al. |
| 2004/0003819 A1 | 1/2004 | St Goar |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049211 A1 | 3/2004 | Tremulis et al. |
| 2004/0073302 A1 | 4/2004 | Rourke et al. |
| 2004/0078053 A1 | 4/2004 | Berg et al. |
| 2004/0087975 A1 | 5/2004 | Lucatero et al. |
| 2004/0088047 A1 | 5/2004 | Spence et al. |
| 2004/0092962 A1 | 5/2004 | Thornton et al. |
| 2004/0093023 A1 | 5/2004 | Allen et al. |
| 2004/0097878 A1 | 5/2004 | Anderson et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |

(56) References Cited

U.S. PATENT DOCUMENTS

| | | |
|---|---|---|
| 2004/0122448 A1 | 6/2004 | Levine |
| 2004/0127981 A1 | 7/2004 | Rahdert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133082 A1 | 7/2004 | Abraham-Fuchs et al. |
| 2004/0133192 A1 | 7/2004 | Houser et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0138745 A1 | 7/2004 | Macoviak et al. |
| 2004/0148021 A1 | 7/2004 | Cartledge et al. |
| 2004/0152847 A1 | 8/2004 | Emri et al. |
| 2004/0152947 A1 | 8/2004 | Schroeder et al. |
| 2004/0153124 A1 | 8/2004 | Whitman |
| 2004/0153144 A1 | 8/2004 | Seguin |
| 2004/0158123 A1 | 8/2004 | Jayaraman |
| 2004/0162610 A1 | 8/2004 | Laiska et al. |
| 2004/0167539 A1 | 8/2004 | Kuehn et al. |
| 2004/0186486 A1 | 9/2004 | Roue et al. |
| 2004/0186566 A1 | 9/2004 | Hindrichs et al. |
| 2004/0193191 A1 | 9/2004 | Starksen et al. |
| 2004/0215339 A1 | 10/2004 | Drasler et al. |
| 2004/0220593 A1 | 11/2004 | Greenhalgh |
| 2004/0220657 A1 | 11/2004 | Nieminen et al. |
| 2004/0225300 A1 | 11/2004 | Goldfarb et al. |
| 2004/0236354 A1 | 11/2004 | Seguin |
| 2004/0243229 A1 | 12/2004 | Vidlund et al. |
| 2004/0249452 A1 | 12/2004 | Adams et al. |
| 2004/0249453 A1 | 12/2004 | Cartledge et al. |
| 2005/0004583 A1 | 1/2005 | Oz et al. |
| 2005/0004665 A1 | 1/2005 | Aklog |
| 2005/0004668 A1 | 1/2005 | Aklog et al. |
| 2005/0021056 A1 | 1/2005 | St. Goer et al. |
| 2005/0021057 A1 | 1/2005 | St. Goer et al. |
| 2005/0021058 A1 | 1/2005 | Negro |
| 2005/0033446 A1 | 2/2005 | Deem et al. |
| 2005/0038508 A1 | 2/2005 | Gabbay |
| 2005/0049698 A1 | 3/2005 | Bolling et al. |
| 2005/0055089 A1 | 3/2005 | Macoviak et al. |
| 2005/0059351 A1 | 3/2005 | Cauwels et al. |
| 2005/0119597 A1 | 6/2005 | O'Mahony |
| 2005/0131390 A1 | 6/2005 | Heinrich |
| 2005/0149014 A1 | 7/2005 | Hauck et al. |
| 2005/0159810 A1 | 7/2005 | Filsoufi |
| 2005/0177180 A1 | 8/2005 | Kaganov et al. |
| 2005/0197694 A1 | 9/2005 | Pai et al. |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0251001 A1 | 11/2005 | Hassett |
| 2005/0267493 A1 | 12/2005 | Schreck et al. |
| 2005/0273160 A1 | 12/2005 | Lashinski et al. |
| 2005/0287493 A1 | 12/2005 | Novak et al. |
| 2006/0004247 A1 | 1/2006 | Kute et al. |
| 2006/0015003 A1 | 1/2006 | Moaddes et al. |
| 2006/0020275 A1 | 1/2006 | Goldfarb |
| 2006/0030866 A1 | 2/2006 | Schreck |
| 2006/0030867 A1 | 2/2006 | Zadno |
| 2006/0030885 A1 | 2/2006 | Hyde |
| 2006/0058871 A1 | 3/2006 | Zakay et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0089671 A1 | 4/2006 | Goldfarb et al. |
| 2006/0089711 A1 | 4/2006 | Dolan |
| 2006/0135993 A1 | 6/2006 | Seguin |
| 2006/0184203 A1 | 8/2006 | Martin et al. |
| 2006/0195012 A1 | 8/2006 | Mortier et al. |
| 2006/0229708 A1 | 10/2006 | Powell et al. |
| 2006/0252984 A1 | 11/2006 | Randert et al. |
| 2006/0287661 A1 | 12/2006 | Bolduc |
| 2007/0038293 A1 | 2/2007 | St. Goar et al. |
| 2007/0100356 A1 | 5/2007 | Lucatero et al. |
| 2007/0118155 A1 | 5/2007 | Goldfarb et al. |
| 2007/0129737 A1 | 6/2007 | Goldfarb et al. |
| 2007/0197858 A1 | 8/2007 | Goldfarb et al. |
| 2007/0198082 A1 | 8/2007 | Kapadia et al. |
| 2008/0039935 A1 | 2/2008 | Buch et al. |
| 2008/0051703 A1 | 2/2008 | Thornton et al. |
| 2008/0051807 A1 | 2/2008 | St. Goar et al. |
| 2008/0097489 A1 | 4/2008 | Goldfarb et al. |
| 2008/0167714 A1 | 7/2008 | St. Goer et al. |
| 2008/0183194 A1 | 7/2008 | Goldfarb et al. |
| 2008/0208329 A1 | 8/2008 | Bishop et al. |
| 2009/0043381 A1 | 2/2009 | Macoviak et al. |
| 2009/0156995 A1 | 6/2009 | Martin et al. |
| 2009/0163862 A1 | 6/2009 | Kauphusman et al. |
| 2009/0163934 A1 | 6/2009 | Raschdorf, Jr. et al. |
| 2009/0177266 A1 | 7/2009 | Powell et al. |
| 2009/0198322 A1 | 8/2009 | Deem et al. |
| 2009/0270858 A1 | 10/2009 | Hauck et al. |
| 2009/0326567 A1 | 12/2009 | Goldfarb et al. |
| 2010/0016958 A1 | 1/2010 | St. Goer et al. |
| 2010/0022823 A1 | 1/2010 | Goldfarb et al. |
| 2010/0204662 A1 | 8/2010 | Orlov et al. |
| 2011/0178596 A1 | 7/2011 | Hauck |
| 2011/0307055 A1 | 12/2011 | Goldfarb |
| 2015/0257883 A1 | 9/2015 | Basude et al. |
| 2018/0021134 A1 | 1/2018 | McNiven et al. |
| 2018/0126127 A1 | 5/2018 | Devereux et al. |
| 2019/0261997 A1 | 8/2019 | Goldfarb et al. |

FOREIGN PATENT DOCUMENTS

| | | |
|---|---|---|
| EP | 0 558 031 B1 | 2/1993 |
| EP | 0 684 012 A2 | 11/1995 |
| EP | 0 727 239 A2 | 8/1996 |
| EP | 1520530 | 4/2005 |
| EP | 1 674 040 A2 | 6/2006 |
| FR | 2 768 324 A1 | 3/1999 |
| GB | 1 598 111 A | 9/1981 |
| GB | 2 151 142 A | 7/1985 |
| JP | 2-63478 A | 3/1990 |
| JP | H0263478 | 3/1990 |
| JP | 10-234653 A | 9/1998 |
| JP | H10234653 | 9/1998 |
| JP | 11-089937 A | 4/1999 |
| WO | WO 81/00668 A1 | 3/1981 |
| WO | WO 91/01689 A1 | 2/1991 |
| WO | WO 91/18881 A1 | 12/1991 |
| WO | WO 92/12690 A1 | 8/1992 |
| WO | WO 94/18881 A1 | 9/1994 |
| WO | WO 94/18893 A1 | 9/1994 |
| WO | WO 95/15715 A1 | 6/1995 |
| WO | WO 96/14032 A1 | 5/1996 |
| WO | WO 96/22735 A1 | 8/1996 |
| WO | WO 96/30072 A1 | 10/1996 |
| WO | WO 97/25927 A1 | 7/1997 |
| WO | WO 97/26034 A1 | 7/1997 |
| WO | WO 97/38748 A2 | 10/1997 |
| WO | WO 97/39688 A2 | 10/1997 |
| WO | WO 97/48436 A2 | 12/1997 |
| WO | WO 98/07375 A1 | 2/1998 |
| WO | WO 98/24372 A1 | 6/1998 |
| WO | WO 98/30153 A1 | 7/1998 |
| WO | WO 98/32382 A1 | 7/1998 |
| WO | WO 98/35638 A1 | 8/1998 |
| WO | WO 99/00059 A1 | 1/1999 |
| WO | WO 99/07354 A2 | 2/1999 |
| WO | WO 99/13777 A1 | 3/1999 |
| WO | WO 99/66967 A1 | 12/1999 |
| WO | WO 00/02489 A1 | 1/2000 |
| WO | WO 00/03651 A1 | 1/2000 |
| WO | WO 00/03759 A2 | 1/2000 |
| WO | WO 00/12168 A1 | 3/2000 |
| WO | WO 00/44313 A1 | 8/2000 |
| WO | WO 00/59382 A1 | 10/2000 |
| WO | WO 00/60995 A2 | 10/2000 |
| WO | WO 01/00111 A1 | 1/2001 |
| WO | WO 01/00114 A1 | 1/2001 |

(56) References Cited

FOREIGN PATENT DOCUMENTS

| | | |
|---|---|---|
| WO | WO 01/03651 A2 | 1/2001 |
| WO | WO 01/26557 A1 | 4/2001 |
| WO | WO 01/26586 A1 | 4/2001 |
| WO | WO 01/26587 A1 | 4/2001 |
| WO | WO 01/26588 A2 | 4/2001 |
| WO | WO 01/26703 A1 | 4/2001 |
| WO | WO 01/28432 A1 | 4/2001 |
| WO | WO 01/28455 A1 | 4/2001 |
| WO | WO 01/47438 A1 | 7/2001 |
| WO | WO 01/49213 A2 | 7/2001 |
| WO | WO 01/50985 A1 | 7/2001 |
| WO | WO 01/54618 A1 | 8/2001 |
| WO | WO 01/56512 A1 | 8/2001 |
| WO | WO 01/66001 A2 | 9/2001 |
| WO | WO 01/70320 A1 | 9/2001 |
| WO | WO 01/89440 A2 | 11/2001 |
| WO | WO 01/95831 A2 | 12/2001 |
| WO | WO 01/95832 A2 | 12/2001 |
| WO | WO 01/97741 A2 | 12/2001 |
| WO | WO 02/00099 A2 | 1/2002 |
| WO | WO 02/01999 A2 | 1/2002 |
| WO | WO 02/03892 A1 | 1/2002 |
| WO | WO 02/34167 A2 | 5/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 03/001893 A2 | 1/2003 |
| WO | WO 03/003930 A1 | 1/2003 |
| WO | WO 03/020179 A1 | 3/2003 |
| WO | WO 03/028558 A2 | 4/2003 |
| WO | WO 03/037171 A2 | 5/2003 |
| WO | WO 03/047467 A1 | 6/2003 |
| WO | WO 03/049619 A2 | 6/2003 |
| WO | WO 03/073910 A2 | 9/2003 |
| WO | WO 03/073913 A2 | 9/2003 |
| WO | WO 03/105667 A2 | 12/2003 |
| WO | WO 2004/004607 A1 | 1/2004 |
| WO | WO 2004/012583 A2 | 2/2004 |
| WO | WO 2004/012789 A2 | 2/2004 |
| WO | WO 2004/014282 A2 | 2/2004 |
| WO | WO 2004/019811 A2 | 3/2004 |
| WO | 2004030571 A2 | 4/2004 |
| WO | WO 2004/030570 A2 | 4/2004 |
| WO | WO 2004/037317 A2 | 5/2004 |
| WO | WO 2004/045370 A2 | 6/2004 |
| WO | WO 2004/045378 A2 | 6/2004 |
| WO | WO 2004/045463 A2 | 6/2004 |
| WO | WO 2004/047679 A1 | 6/2004 |
| WO | WO 2004/062725 A1 | 7/2004 |
| WO | WO 2004/082523 A2 | 9/2004 |
| WO | WO 2004/082538 A2 | 9/2004 |
| WO | WO 2004/093730 A2 | 11/2004 |
| WO | WO 2004/112585 A2 | 12/2004 |
| WO | WO 2004/112651 A2 | 12/2004 |
| WO | WO 2005/002424 A2 | 1/2005 |
| WO | 2005018426 | 3/2005 |
| WO | WO 2005/018507 A2 | 3/2005 |
| WO | WO 2005/027797 A1 | 3/2005 |
| WO | WO 2005/032421 A2 | 4/2005 |
| WO | WO 2005/062931 A2 | 7/2005 |
| WO | WO 2005/112792 A2 | 12/2005 |
| WO | 2006037073 A2 | 4/2006 |
| WO | WO 2006/105008 A1 | 10/2006 |
| WO | WO 2006/105009 A1 | 10/2006 |
| WO | WO 2006/115875 A2 | 11/2006 |
| WO | WO 2006/115876 A2 | 11/2006 |

OTHER PUBLICATIONS

U.S. Appl. No. 12/575,100 (U.S. Pat. No. 8,052,592), filed Oct. 7, 2009 (Nov. 8, 2011).
U.S. Appl. No. 11/237,213 (Abandoned), filed Sep. 22, 2011.
U.S. Appl. No. 14/070,936 (Abandoned), filed Nov. 4, 2013.
U.S. Appl. No. 16/279,523 (US 2019-0175203), filed Feb. 19, 2019 (Jun. 13, 2019).
U.S. Appl. No. 16/912,361 (U.S. Pat. No. 11,304,715), filed Jun. 25, 2020 (Apr. 19, 2022).
U.S. Appl. No. 11/237,213, Oct. 7, 2009 Issue Fee Payment.
U.S. Appl. No. 11/237,213, Sep. 23, 2009 Notice of Allowance.
U.S. Appl. No. 11/237,213, Aug. 5, 2009 Response to Non-Final Office Action.
U.S. Appl. No. 11/237,213, Jul. 24, 2009 Non-Final Office Action.
U.S. Appl. No. 11/237,213, Sep. 24, 2008 Response to Non-Final Office Action.
U.S. Appl. No. 11/237,213, Sep. 10, 2008 Non-Final Office Action.
U.S. Appl. No. 11/237,213, Jun. 30, 2008 Response to Restriction Requirement.
U.S. Appl. No. 11/237,213, Jun. 23, 2008 Restriction Requirement.
U.S. Appl. No. 12/575,100, Sep. 25, 2011 Issue Fee Payment.
U.S. Appl. No. 12/575,100, Jul. 26, 2011 Notice of Allowance.
U.S. Appl. No. 12/575,100, May 2, 2011 Response to Non-Final Office Action.
U.S. Appl. No. 12/575,100, Feb. 1, 2011 Non-Final Office Action.
U.S. Appl. No. 12/575,100, Nov. 9, 2010 Response to Non-Final Office Action.
U.S. Appl. No. 12/575,100, Aug. 25, 2010 Non-Final Office Action.
U.S. Appl. No. 13/239,514, Mar. 12, 2014 Notice of Abandonment.
U.S. Appl. No. 13/239,514, Sep. 9, 2013 Applicant Initiated Interview Summary.
U.S. Appl. No. 13/239,514, Aug. 12, 2013 Advisory Action.
U.S. Appl. No. 13/239,514, Aug. 2, 2013 Response after Final Action.
U.S. Appl. No. 13/239,514, May 2, 2013 Final Office Action.
U.S. Appl. No. 13/239,514, Mar. 22, 2013 Response to Non-Final Office Action.
U.S. Appl. No. 13/239,514, Sep. 26, 2012 Non-Final Office Action.
U.S. Appl. No. 13/239,514, Aug. 22, 2012 Response to Restriction Requirement.
U.S. Appl. No. 13/239,514, Jul. 23, 2012 Restriction Requirement.
U.S. Appl. No. 14/070,936, Feb. 22, 2019 Notice of Abandonment.
U.S. Appl. No. 14/070,936, Dec. 18, 2018 Patent Board Decision—Examiner Affirmed.
U.S. Appl. No. 14/070,936, Jul. 14, 2017 Reply Brief Filed.
U.S. Appl. No. 14/070,936, May 16, 2017 Examiner's Answer to Appeal Brief.
U.S. Appl. No. 14/070,936, Apr. 10, 2017 Appeal Brief Filed.
U.S. Appl. No. 14/070,936, Feb. 6, 2017 Notice of Appeal Filed.
U.S. Appl. No. 14/070,936, Aug. 8, 2016 Final Office Action.
U.S. Appl. No. 14/070,936, Jul. 20, 2016 Response to Non-Final Office Action.
U.S. Appl. No. 14/070,936, Jun. 13, 2016 Applicant Initiated Interview Summary.
U.S. Appl. No. 14/070,936, Apr. 25, 2016, Non-Final Office Action.
U.S. Appl. No. 14/070,936, Dec. 9, 2015 Request for Continued Examination (RCE).
U.S. Appl. No. 14/070,936, Oct. 5, 2015 Advisory Action.
U.S. Appl. No. 14/070,936, Sep. 28, 2015 Amendment and Request for Continued Examination (RCE).
U.S. Appl. No. 14/070,936, Jul. 9, 2015 Final Office Action.
U.S. Appl. No. 14/070,936, Jun. 15, 2015 Response to Non-Final Office Action.
U.S. Appl. No. 14/070,936, Feb. 13, 2015 Non-Final Office Action.
U.S. Appl. No. 14/070,936, Jan. 22, 2015 Response to Restriction Requirement.
U.S. Appl. No. 14/070,936, Nov. 25, 2014 Restriction Requirement.
U.S. Appl. No. 16/279,523, Sep. 21, 2022 Issue Fee Payment.
U.S. Appl. No. 16/279,523, Jul. 26, 2022 Notice of Allowance.
U.S. Appl. No. 16/279,523, Jul. 5, 2022 Response to Non-Final Office Action.
U.S. Appl. No. 16/279,523, Feb. 3, 2022 Non-Final Office Action.
U.S. Appl. No. 16/279,523, Nov. 22, 2021 Request for Continued Examination (RCE).
U.S. Appl. No. 16/279,523, Nov. 4, 2021 Advisory Action.
U.S. Appl. No. 16/279,523, Nov. 4, 2021 After Final Consideration Program Decision.

(56) References Cited

OTHER PUBLICATIONS

U.S. Appl. No. 16/279,523, Oct. 25, 2021 After Final Consideration Program Request and Response to Final Office Action.
U.S. Appl. No. 16/279,523, Jul. 23, 2021 Final Office Action.
U.S. Appl. No. 16/279,523, Jul. 2, 2021 Resposnse to Non-Final Office Action.
U.S. Appl. No. 16/279,523, Apr. 2, 2021 Non-Final Office Action.
U.S. Appl. No. 16/279,523, Jan. 5, 2021 Amendment and Request for Continued Examination (RCE).
U.S. Appl. No. 16/279,523, Oct. 5, 2020 Final Office Action.
U.S. Appl. No. 16/279,523, Sep. 2, 2020 Response to Non-Final Office Action.
U.S. Appl. No. 16/279,523, Jun. 2, 2020 Non-Final Office Action.
U.S. Appl. No. 16/279,523, May 15, 2020 Response to Restriction/Election Requirement.
U.S. Appl. No. 16/279,523, Mar. 25, 2020 Restriction/Election Requirement.
U.S. Appl. No. 16/912,361, Mar. 15, 2022 Issue Fee Payment.
U.S. Appl. No. 16/912,361, Dec. 15, 2021 Notice of Allowance.
U.S. Appl. No. 16/912,361, Nov. 17, 2021 Letter Withdrawing/Vacating Office Action.
U.S. Appl. No. 16/912,361, Nov. 8, 2021 Non-Final Office Action.
U.S. Appl. No. 16/912,361, Oct. 18, 2021 Appeal Brief.
U.S. Appl. No. 16/912,361, Aug. 16, 2021 Notice of Appeal.
U.S. Appl. No. 16/912,361, May 14, 2021 Non-Final Office Action.
U.S. Appl. No. 16/912,361, Apr. 23, 2021 Request for Continued Examination (RCE).
U.S. Appl. No. 16/912,361, Apr. 2, 2021 Advisory Action.
U.S. Appl. No. 16/912,361, Apr. 2, 2021 After Final Consideration Program Decision.
U.S. Appl. No. 16/912,361, Mar. 26, 2021 After Final Consideration Program Request and Response to Final Office Action.
U.S. Appl. No. 16/912,361, Jan. 27, 2021 Final Office Action.
U.S. Appl. No. 16/912,361, Jan. 13, 2021 Response to Non-Final Office Action.
U.S. Appl. No. 16/912,361, Oct. 21, 2020 Applicant Summary of Interview with Examiner.
U.S. Appl. No. 16/912,361, Oct. 13, 2020 Non-Final Office Action.
U.S. Appl. No. 16/912,361, Sep. 21, 2020 Applicant Initiated Interview Summary.
U.S. Appl. No. 16/912,361, Sep. 17, 2020 Response to Restriction/Election Requirement.
U.S. Appl. No. 16/912,361, Jul. 17, 2020 Restriction/Election Requirement.
Abe et al., "De Vega's annuloplasty for acquired tricuspid disease: Early and late results in 110 patients," Ann. Thorac. Surg. (Nov. 1989) 48:670-676.
Abe et al., "Updated: De Vega's annuloplasty for acqiuried tricuspiddisease: Early and late results in patients," Ann. Thorac. Surg. (Dec. 1996) 62:1876-1877.
Agricola et al., "Mitral Valve Reserve in Double Orifice Technique: an Exercise Echocardiographic Study," Journal of Heart Valve Disease, 11(5):637-643 (2002).
Alfieri et al., "An Effective Technique to Correct Anterior Mitral Leaflet Prolapse," J. Card Surg., 14:468-470 (1999).
Alfieri et al., "Novel Suture Device for Beating Heart Mitral Leaflet Approximation," Annals of Thoracic Surgery, 74:1488-1493 (2002).
Alfieri et al., "The double orifice technique in mitral valve repair: a simple solution for complex problems," Journal of Thoracic and Cardiovascular Surgery, 122:674-681 (2001).
Alfieri et al., "The Edge to Edge Technique," The European Association For Cardio-Thoracic Surgery, 14th Annual Meeting, Frankfurt / Germany, Oct. 7-11, 2000, Post Graduate Courses, Book of Proceedings.
Alfieri, "The Edge-to-Edge Repair of the Mitral Valve," [Abstract] 6th Annual New Era Cardiac Care: Innovation & Technology, Heart Surgery Forum, (Jan. 2003) pp. 103.
Alvarez et al., "Repairing the Degenerative Mitral Valve: Ten- to Fifteen-Year Follow-up," J. Thorac. Cardiovasc. Surg. (Aug. 1996) 112:238-247.
Arisi et al., "Mitral Valve Repair with Alfieri Technique in Mitral Regurgitation of Diverse Etiology: Early Echocardiographic Results," Circulation Supplement II, 104(17):3240 (2001).
Bach et al., "Early improvement in congestive heart failure after correction of secondary mitral regurgitation in end-stage cardiomyopathy," Am. Heart J., (Jun. 1995) 129:1165-1170.
Bach et al., "Improvement following correction of secondary mitrel regurgitation in end-stage cardiomyopathy with mitral annuloplasty," Am. J. Cardiol., (Oct. 1996) 78:966-969.
Bailey, "Mitral Regurgitation" in Surgery of the Heart, Chapter 20, pp. 686-737 (1955).
Bernal et al., "The Valve Racket: a new and different concept of atrioventricular valve repair," Eur. J. Cardio-thoracic Surgery 29:1026-1029 (2006).
Bhudia et al., "Edge-to-Edge (Alfieri) Mitral Repair: Results in Diverse Clinical Settings," Ann Thorac Surg, 77:1598-1606 (2004).
Bhudia, #58 Edge-to-edge mitral repair: a versatile mitral repair technique, 2003 STS Presentation, [Abstract Only].
Bolling et al., "Surgery for acquired heart disease" (Apr. 1995) 109:676-683.
Borghetti et al., "Preliminary observations on haemodynamics during physiological stress conditions following 'double-orifice' mitral valve repair," European Journal of Cardio-thoracic Surgery, 20:262-269 (2001).
Castedo, "Edge-to-Edge Tricuspid Repair for Redeveloped Valve Incompetence after DeVega's Annuloplasty," Ann Thora Surg., 75:605-606 (2003).
Dec et al., "Idiopathic dilated cardiomyopathy," N. Engl. J.Med. (Dec. 1994) 331:1564-1575.
Derwent citing German language patent EP 684012 published Nov. 12, 1995 for: "Thread for constructing surgical seam has flexible section with two ends, with lower fastening part on thread first end having hollow cylinder with continuous hole through which surgical needle threads," 2 pgs.
Derwent citing Japanese language patent JP 11089937 published 614/99 for: "Catheter for mitral regurgitation test—includes jet nozzles provided on rear side of large diameter spindle shaped portion attached to end of narrow diametered tube" 1 pg.
Dottori et al., "Echocardiographic imaging of the Alfieri type mitral valve repair," Ital. Heart J., 2(4):319-320 (2001).
Downing et al., "Beating heart mitral valve surgery: Preliminary model and methodology," Journal of Thoracic and Cardiovascular Surgery, 123(6): 1141-1146 (2002).
Extended European Search Report issued in European Application No. 05805707.6 dated Aug. 7, 2012.
Falk et al., "Computer-Enhanced Mitral Valve Surgery: Toward a Total Endoscopic Procedure," Seminars in Thoracic and Cardiovascular Surgery, 11(3):244-249 (1999).
Filsoufi et al., "Restoring Optimal Surface of Coaptation With a Mini Leaflet Prosthesis: A New Surgical Concept for the Correction of Mitral Valve Prolapse," Intl. Soc. for Minimally Invasive Cardiothoracic Surgery 1(4):186-87 (2006).
Frazier et al., "Early Clinical Experience with an Implantable, Intracardiac Circulatory Support Device: Operative Considerations and Physiologic Implications," http://www.sts.org/doc/7007 accessed on Sep. 24, 2008.
Fucci et al., "Improved results with mitral valve repair using new surgical techniques", Eur. J. Cardiothorac. Surg. (Nov. 1995) 9:621-627.
Fundaro et al., "Chordal Plication and Free Edge Remodeling for Mitral Anterior Leaflet Prolapse Repair: 8-Year Follow-up," Annals of Thoracic Surgery, 72:1515-1519 (2001).
Garcia-Rinaldi et al., "Left Ventricular vol. Reduction and Reconstruction is Ischemic Cardiomyopathy," Journal of Cardiac Surgery, 14:199-210 (1999).
Gateliene et al., "Early and late postoperative results of mitral and tricuspid valve insufficiency surgical treatment using edge-to-edge central coaptation procedure," Medicina (Kaunas) 38(Suppl. 2):172-175 (2002).
Gatti et al., "The edge to edge technique as a trick to rescue an imperfect mitral valve repair," Eur. J. Cardiothorac Surg, 22:817-820 (2002).

(56) References Cited

OTHER PUBLICATIONS

Gillinov et al., "Is Minimally Invasive Heart Valve Surgery a Paradigm for the Future?" Current Cardiology Reports, 1:318-322 (1999).
Gundry et al., "Facile Mitral Valve Repair Utilizing Leaflet Edge Approximation: Midterm Results of the Alfieri Figure of Eight Repair," The Western Thoracic Surgical Association, Scientific Session (May 1999).
Gupta et al., "Influence of Older Donor Grafts on Heart Transplant Survival: Lack of Recipient Effects," http://www.sts.org/doc/7007 accessed on Sep. 24, 2008.
Ikeda et al., "Batista's Operation with Coronary Artery Bypass Grafting and Mitral Valve Plasty for Ischemic Dilated Cardiomyopathy," The Japanese Journal of Thoracic and Cardiovascular Surgery, 48:746-749 (2000).
International Search Report and Written Opinion of PCT Application No. PCT/U505/34902, dated Jul. 23, 2008, 10 pages total.
Izzat et al., "Early Experience with Partial Left Ventriculectomy in the Asia-Pacific Region," Annuals of Thoracic Surgery, 67:1703-1707 (1999).
Kallner et al., "Transaortic Approach for the Alfieri Stitch," Ann Thorac Surg, 71:378-380 (2001).
Kameda et al., "Annuloplasty for severe mitral regurgitation due to dilated cardiomyopathy," Am. Thorac. Surg. (Jun. 1996) 61:1829-1832.
Kavarana et al., "Transaortic Repair of Mitral Regurgitation," The Heart Surgery Forum, #2000-2389, 3(1):24-28 (2000).
Kaza et al., "Ventricular Reconstruction Results in Improved Left Ventricular Function and Amelioration of Mitral Insufficiency," Annals of Surgery, 235(6):828-832 (2002).
Khan et al. "Blade atrial septostomy: Experience with the first 50 procedures" Cathet. Cardiovasc. Diagn. (Aug. 1991) 23: 257-262.
Kherani et al., "The Edge-To-Edge Mitral Valve Repair: The Columbia Presbyterian Experience," Ann. Thorac. Surg., 78:73-76 (2004).
Konertz et al., "Results After Partial Left Ventriculectomy in a European Heart Failure Population," Journal of Cardiac Surgery, 14:129-135 (1999).
Kron et al., "Surgical Relocation of the Posterior Papillary Muscle in Chronic Ischemic Mitral Regurgitation," Annals. Of Thoracic Surgery, 74:600-601 (2002).
Kruger et al., "P73—Edge to Edge Technique in Complex Mitral Valve Repair," Thorac Cardiovasc Surg., 48(Suppl. 1):106 (2000).
Langer et al., "Posterier mitral leaflet extensions: An adjunctive repair option for ischemic mitral regurgitation?" J Thorac Cardiovasc Surg, 131:868-877 (2006).
Lorusso et al., "'Double-Orifice' Technique to Repair Extensive Mitral Valve Excision Following Acute Endocarditis," J. Card Surg, 13:24-26 (1998).
Lorusso et al., "The double-orifice technique for mitral valve reconstruction: predictors of postoperative outcome," Eur J. Cardiothorac Surg, 20:583-589 (2001).
Maisano et al., "The Double Orifice Repair for Barlow Disease: A Simple Solution for Complex Repair," Circulation 100(18):1-94 (1999).
Maisano et al., "The double orifice technique as a standardized approach to treat mitral regurgitation due to severe myxomatous disease: surgical technique," European Journal of Cardio-thoracic Surgery, 17:201-205 (2000).
Maisano et al., "The edge-to-edge technique: A simplified method to correct mitral insufficiency," Eur. J. Cardiothorac. Surg., (Mar. 1998) 13:240-246.
Maisano et al., "The hemodynamic effects of double-orifice valve repair for mitral regurgitation: a 3D computational model," European Journal of Cardio-thoracic Surgery, 15:419-425 (1999).
Maisano et al., "Valve repair for traumatic tricuspid regurgitation," Eur. J. Cardio-thorac Surg, 10:867-873 (1996).
Mantovani et al., "Edge-to-edge Repair of Congenital Familiar Tricuspid Regurgitation: Case Report," J. Heart Valve Dis., 9:641-643 (2000).
McCarthy et al., "Partial left ventriculectomy and mitral valve repair for end-stage congestive heart failure," European Journal of Cardio-thoracic Surgery, 13:337-343 (1998).
McCarthy et al., "Tricuspid Valve Reapir with the Cosgrove-Edwards Annuloplasty System," Ann. Thorac.Surg., (Jul. 1997) 64:267-268.
Moainie et al., "Correction of Traumatic Tricuspid Regurgitation Using the Double Orifice Technique," Annals of Thoracic Surgery, 73:963-965 (2002).
Morales et al., "Development of an Off Bypass Mitral Valve Repair," The Heart Surgery Forum #1999-4693, 2(2):115-120 (1999).
Nakanishi et al., "Early Outcome with the Alfieri Mitral Valve Repair," J. Cardiol., 37: 263-266 (2001) [Abstract in English; Article in Japanese].
Nielsen et al., "Edge-to-Edge Mitral Repair: Tension of the Approximating Suture and Leaflet Deformation During Acute Ischemic Mitral Regurgitation in the Ovine Heart," Circulation, 104(Suppl. I):I-29-I-35 (2001).
Noera et al., "Tricuspid Valve Incompetence Caused by Nonpenetrating Thoracic Trauma", Annals of Thoracic Surgery, 51:320-322 (1991).
Osawa et al., "Partial Left Ventriculectomy in a 3-Year Old Boy with Dilated Cardiomyopathy," Japanese Journal of Thoracic and Cardiovascular Surg, 48:590-593 (2000).
Park et al., "Clinical use of a blade atrial septostomy" Circulation (Oct. 1978) 58:600-608.
Patel et al., "Epicardial Atrial Defibrillation: Novel Treatment of Postoperative Atrial Fibrillation," http://www.sts.org/doc/7007 accessed on Sep. 23, 2008.
Privitera et al., "Alfieri Mitral Valve Repair: Clinical Outcome and Pathology," Circulation, 106:e173-e174 (2002).
Redaelli et al., "A Computational Study of the Hemodynamics After 'Edge-To-Edge' Mitral Valve Repair," Journal of Biomechanical Engineering, 123:565-570 (2001).
Reul et al., "Mitral Valve Reconstruction for Mitral Insufficiency," Progress in Cardiovascular Diseases, XXXIX(6):567-599 (1997).
Ricchi et al., "Linear segmental annuloplasty for mitral valve repair" Ann. Thorac. Surg., (Jun. 1997) 63:1805-1806.
Robicsek et al., "The Bicuspid Aortic Valve. How Does It Function? Why Does It Fail," http://www.sts.org/doc/7007 accessed on Sep. 24, 2008.
Tager et al., "Long-term follow-up of rheumatic patients undergoing left-sided valve replacement with tricuspid annuloplasty-Validity of preoperative echocardiographic criteria in the decision to perform tricuspid annuloplasty," Am. J. Cardiol., (Apr. 1998) 81:1013-1016.
Tamura et al., "Edge to Edge Repair for Mitral Regurgitation in a Patient with Chronic Hemodialysis: Report of A Case," Kyobu Geka. The Japanese Journal of Thoracic Surgery, 54(9):788-790 (2001).
Tibayan et al., "Annular Geometric Remodeling in Chronic Ischemic Mitral Regurgitation," http://www.sts.org/doc/7007 accessed on Sep. 24, 2008.
Timek et al., "Edge-to-edge mitral repair: gradients and three-dimensional annular dynamics in vivo during inotropic stimulation," Eur J. of Cardiothoracic Surg., 19:431-437 (2001).
Timek, "Edge-to-Edge Mitral Valve Repair without Annuloplasty Ring in Acute Ischemic Mitral Regurgitation," [Abstract] Clinical Science, Abstracts from Scientific Sessions, 106(19):2281 (2002).
Totaro, "Mitral valve repair for isolated prolapse of the anterior leaflet: an 11-year follow-up," European Journal of Cardio-thoracic Surgery, 15:119-126 (1999).
Uchida et al., "Percutaneous cardiomyotomy and valvulotomy with angioscopic guidance," Am. Heart J., (Apr. 1991) 121:1221-1224.
Umana et al., "''Bow-tie' Mitral Valve Repair Successfully Addresses Subvalvular Dysfunction in Ischemic Mitral Regurgitation," Surgical Forum, XLVIII:279-280 (1997).
Umana et al., "Bow-tie" mitral valve repair: An Adjuvant technique for ischemic regurgitation Ann. Thorac. Surg., (Nov. 1998) 66:1640-1646.
Votta et al., "3-D Computational Analysis of the Stress Distribution on the Leaflets after Edge-to-Edge Repair of Mitral Regurgitation," Journal of Heart Valve Disease, 11:810-822 (2002).

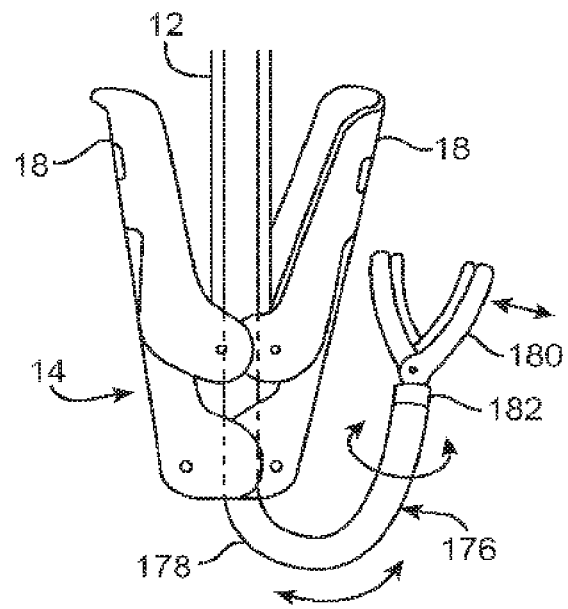
FIG. 19A
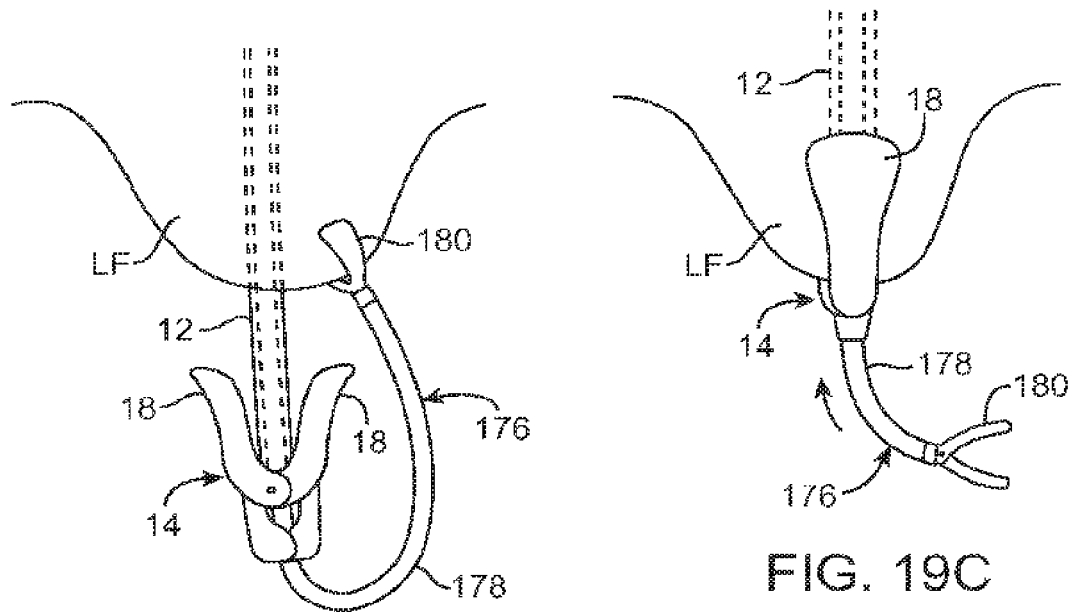
FIG. 19B
FIG. 19C

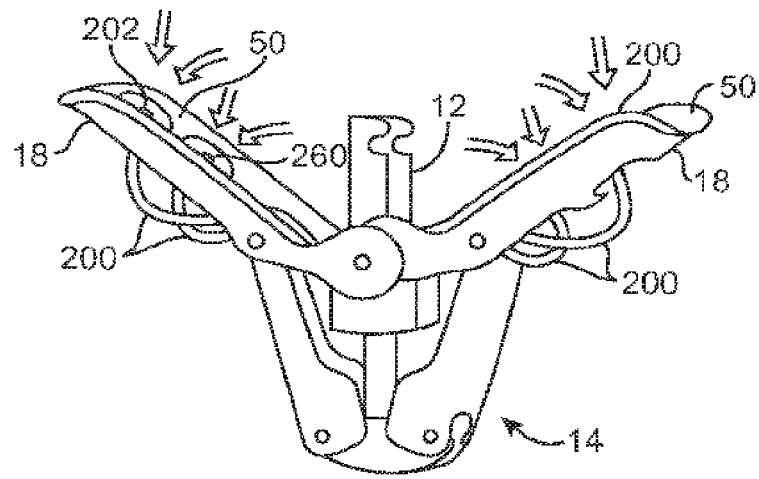
FIG. 23
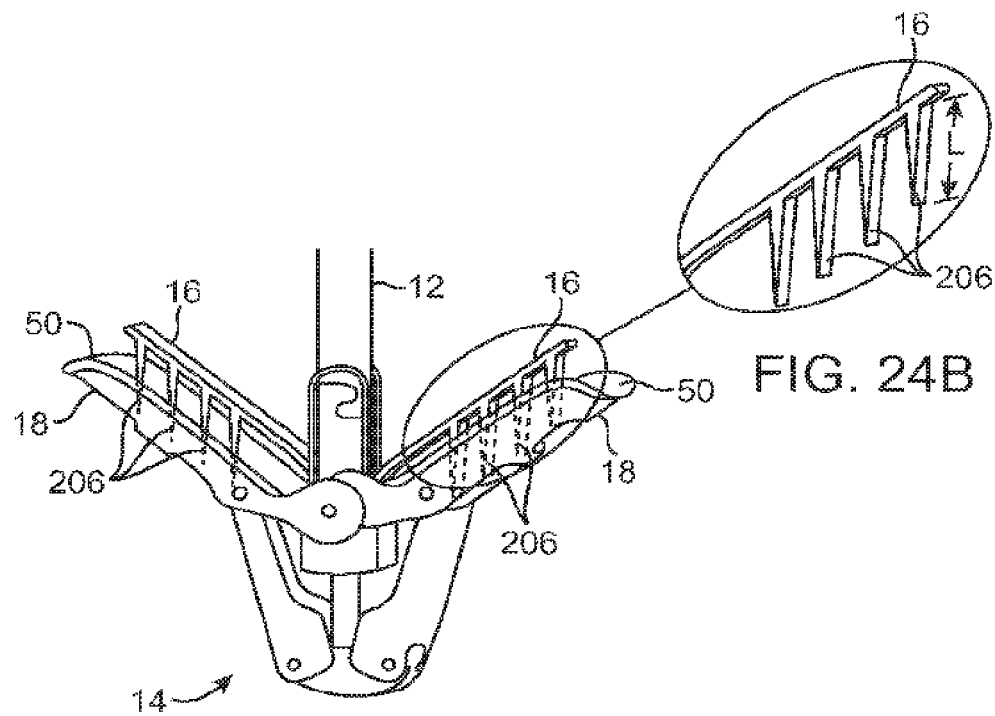
FIG. 24B
FIG. 24A

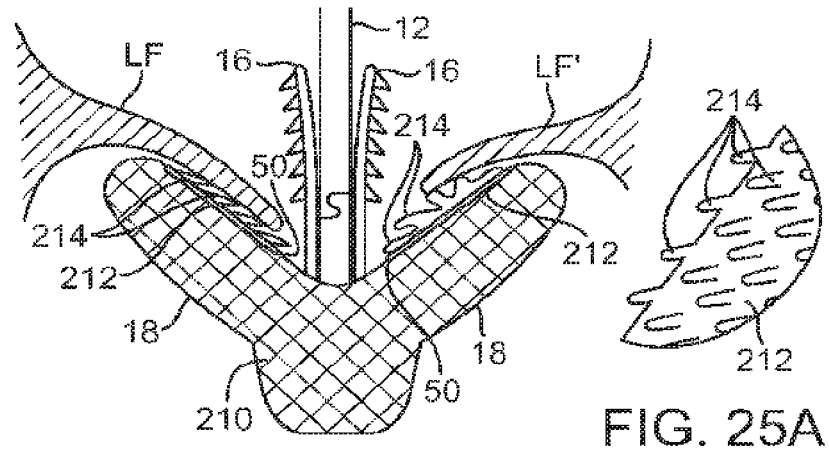
FIG. 25A
FIG. 25B
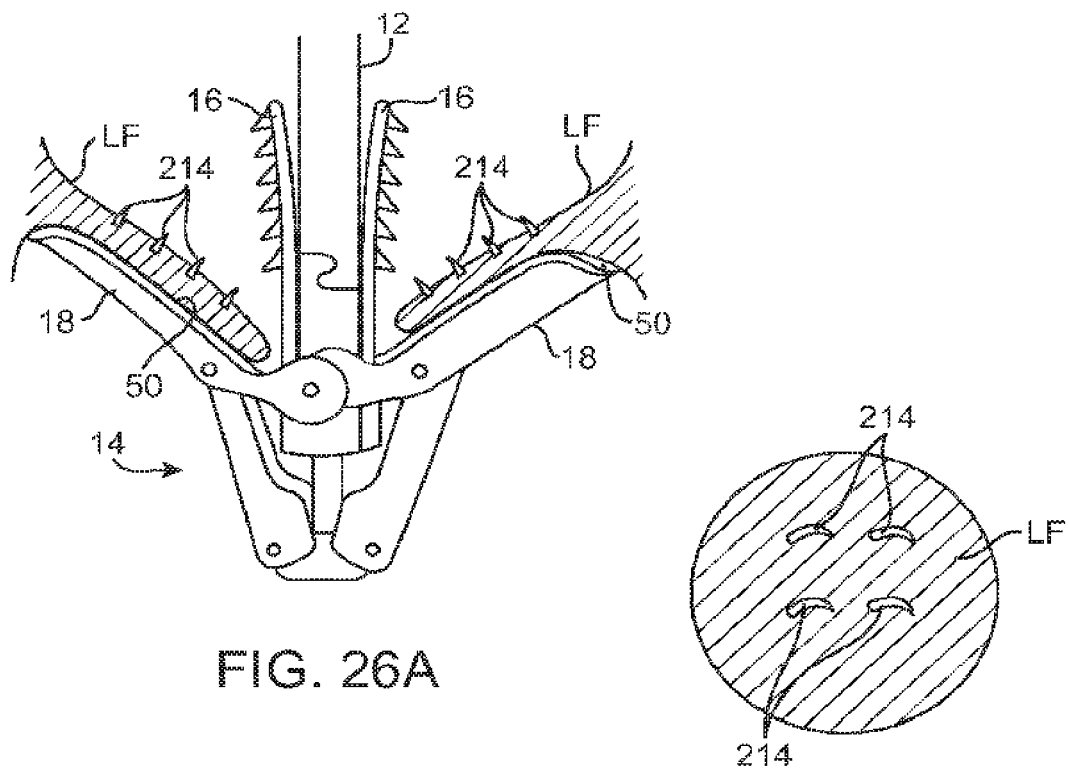
FIG. 26A
FIG. 26B

METHODS AND DEVICES FOR TISSUE GRASPING AND ASSESSMENT

CROSS-REFERENCES TO RELATED APPLICATIONS

The present application is a continuation of U.S. patent application Ser. No. 16/912,361, filed Jun. 25, 2020, which is a continuation of U.S. patent application Ser. No. 16/279,523, filed Feb. 19, 2019, which is a continuation of U.S. patent application Ser. No. 14/070,936, filed Nov. 4, 2013, which is a continuation of U.S. patent application Ser. No. 13/239,514, filed Sep. 22, 2011, now abandoned, which is a continuation of U.S. patent application Ser. No. 12/575,100, now U.S. Pat. No. 8,052,592, filed Oct. 7, 2009, which is a divisional of U.S. patent application Ser. No. 11/237,213, now U.S. Pat. No. 7,635,329, filed Sep. 27, 2005 which claims the benefit and priority of U.S. Provisional Patent Application No. 60/613,867, filed Sep. 27, 2004, the full disclosures of which are hereby incorporated by reference.

BACKGROUND OF THE INVENTION

1. Field of the Invention

The present invention relates generally to medical methods, devices, and systems. In particular, the present invention relates to methods, devices, and systems for the endovascular, percutaneous or minimally invasive surgical treatment of bodily tissues, such as tissue approximation or valve repair. More particularly, the present invention relates to repair of valves of the heart and venous valves.

Surgical repair of bodily tissues often involves tissue approximation and fastening of such tissues in the approximated arrangement. When repairing valves, tissue approximation includes coapting the leaflets of the valves in a therapeutic arrangement which may then be maintained by fastening or fixing the leaflets. Such coaptation can be used to treat regurgitation which most commonly occurs in the mitral valve.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the valve can significantly decrease the pumping efficiency of the heart, placing the patient at risk of severe, progressive heart failure.

Mitral valve regurgitation can result from a number of different mechanical defects in the mitral valve or the left ventricular wall. The valve leaflets, the valve chordae which connect the leaflets to the papillary muscles, the papillary muscles or the left ventricular wall may be damaged or otherwise dysfunctional. Commonly, the valve annulus may be damaged, dilated, or weakened limiting the ability of the mitral valve to close adequately against the high pressures of the left ventricle.

The most common treatments for mitral valve regurgitation rely on valve replacement or repair including leaflet and annulus remodeling, the latter generally referred to as valve annuloplasty. A recent technique for mitral valve repair which relies on suturing adjacent segments of the opposed valve leaflets together is referred to as the "bow-tie" or "edge-to-edge" technique. While all these techniques can be very effective, they usually rely on open heart surgery where the patient's chest is opened, typically via a sternotomy, and the patient placed on cardiopulmonary bypass. The need to both open the chest and place the patient on bypass is traumatic and has associated high mortality and morbidity.

Consequently, alternative and additional methods, devices, and systems for performing the repair of mitral and other cardiac valves have been developed. Such methods, devices, and systems preferably do not require open chest access and are capable of being performed either endovascularly, i.e., using devices which are advanced to the heart from a point in the patient's vasculature remote from the heart or by a minimally invasive approach. Examples of such methods, devices and systems are provided in U.S. Pat. Nos. 6,629,534 6,752,813, and U.S. patent application Ser. Nos. 10/441,753, 10/441,531, 11/130,818, 10/441,508, 10/441,687, 10/975,555, all of which are incorporated herein by reference for all purposes.

In some instances, however, a variety of challenges are faced in desirably fixating the valve leaflets. For example, it is commonly found in cases of mitral valve regurgitation that a portion of the leaflet is moving out of phase with the other leaflets or portions of the leaflets. This can occur due to an elongation or disconnection of the structures (chordae tendinae) holding the leaflets stable and in synchrony. Such a malfunction can lead to one leaflet or portion of a leaflet to swing or "flail" above the level of healthy coaptation, thereby allowing blood to regurgitate into the right atrium. Such flailing provides a challenge to the practitioner when attempting to fix the leaflets together, particularly via an endoscopic approach. The leaflets may be difficult to grasp, and even when grasped, the leaflets may not be desirably grasped. For example, a leaflet may only be partially grasped rather than having full contact with a grasping element. This may lead to less desirable coaptation and/or eventual slippage of the leaflet from fixation.

Therefore, devices, systems and methods are desired which stabilize the tissue, to resist flailing and other movement, prior to and/or during grasping of the tissue. Further, devices, systems and methods are desired which assist in grasping the tissue, enable more desirable coaptation of tissues, provide grasping assessment, and enable the practitioner to determine if desirable grasping of the tissues has occurred, particularly prior to fixation. And still further, devices, systems and methods are desired which enable fixation assessment, enabling the practitioner to determine if desirable fixation of the tissues has occurred. These would be useful for repair of tissues in the body other than leaflets and other than heart valves. At least some of these objectives will be met by the inventions described hereinbelow.

BRIEF SUMMARY OF THE INVENTION

The present invention provides a variety of devices, systems and methods for stabilizing, grasping, assessing and fixating tissues, particularly valve leaflets in the treatment of cardiac valve regurgitation, more particularly mitral valve regurgitation. Many of the devices, systems and methods utilize or are utilized in conjunction with a preferred embodiment of a fixation device having at least one proximal element and at least one distal element, wherein the tissue is grasped therebetween. It may be appreciated, however, that the devices, systems and methods of the present invention may utilize any suitable device, particularly any minimally invasive device. When treating valve leaflets, the leaflets are typically grasped to position the fixation device along the line of coaptation at a location which reduces regurgitation of the valve, such as near the center of the valve simulating a standard surgical bow-tie repair. However, more than one fixation device may be placed, and in various arrangements, as will be discussed in later sections.

To assist in desirable grasping of the tissue, a variety of devices and techniques are provided to stabilize the tissue prior to grasping. Such stabilization is aimed to assist in effectively and efficiently grasping the tissue thereby increasing the likelihood that the desired amount of tissue will be incorporated into the fixation device without necessitating multiple grasps. Further, a variety of devices and techniques are provided to improve a grasp, such as by adjusting the position of the grasped tissue between the proximal and distal elements. Once the tissue or leaflets have been grasped, it is often desired to evaluate or assess the quality of the grasp, such as the amount of purchase, orientation of the tissues and likelihood that the fixation device will maintain the grasp over time. Thus, a variety of devices and techniques are provided to assess the quality of the grasp. Further, once the tissue has been fixed by the fixation device, the quality of the fixation of the tissue may be evaluated or assessed. This can be achieved by evaluating the improvement in the medical condition being treated, such as improvement in regurgitation. It is often desired to assess the fixation prior to decoupling the fixation device from the delivery catheter so that the fixation device may be repositioned if the improvement is not satisfactory. Thus, a variety of devices and techniques are provided to assess the fixation prior to decoupling the fixation devices. Additional devices, systems and methods are also provided.

In one aspect of the present invention, methods are provided for assessing the grasp of one or more tissues by a minimally invasive device. In one embodiment, the method includes advancing a minimally invasive device having a proximal element and a distal element into a body cavity having a tissue, grasping the tissue between the proximal element and the distal element and assessing the presence of the tissue in a target area between the proximal and distal elements. Typically, the tissue comprises valve leaflets. In some embodiments, assessing the presence comprises observing the target area under fluoroscopy, ultrasound or echocardiography. In such instances, the method may further comprise enhancing the visibility of at least a portion of the proximal element and/or the distal element. Alternatively or in addition, the method may further comprise enhancing the visibility of the tissue.

In a variety of embodiments, the device includes an indicator which indicates the presence of tissue within the target area. In such instances, the method may further comprise observing the indicator. When the indicator changes shape and/or orientation based on the presence of tissue within the target area, observing the indicator may include observing the change in shape and/or orientation.

In some embodiments, the device includes an injectable enhanced visibility substance. In such instances, assessing the presence of tissue in the target area may comprise observing a flow pattern of the enhanced visibility substance. When the substance is contained in a reservoir having ports, assessing the presence of tissue in the target area may comprise observing the substance flowing through ports near the target area.

In further embodiments, the method further comprising introducing an injectable enhanced visibility substance through the device. In such instances, assessing the presence of tissue in the target area may comprise observing the absence of a flow pattern of the enhanced visibility substance. In still further embodiments, the method further includes advancing a probe into the target area. In such instances, assessing the presence of the tissue in a target area may comprise determining a depth of the probe advancement. In some embodiments, the device includes a sensor which indicates the presence of tissue within the target area, wherein the method further comprises evaluating a signal from the sensor.

In another aspect of the present invention, methods are provided for adjusting the tissue grasped between the proximal and distal element. In some embodiments, the method comprises advancing a minimally invasive device having a proximal element and a distal element into a body cavity having a tissue, grasping the tissue between the proximal element and the distal element, and adjusting the tissue between the proximal element and the distal element. Adjusting may comprise applying suction to the tissue and moving the tissue by suction forces. When the device includes a secondary grasper, adjusting may comprise grasping and moving the tissue with the secondary grasper. When the device includes a rotating component which moves the tissue between the proximal and distal elements, adjusting may comprise rotating the rotating component. When the proximal element is moveable relative to the distal element, adjusting may comprise moving the proximal element relative to the distal element. Typically, the tissue comprises valve leaflets.

In another aspect of the present invention, methods are provided for temporarily stabilizing valve leaflets. In some embodiments, the method includes advancing a minimally invasive device into a chamber of a heart having a valve with valve leaflets, temporarily stabilizing the valve leaflets by reducing movement of the valve leaflets. When the chamber comprises the left atrium, the valve comprises the mitral valve, and the device includes a stabilizer, temporarily stabilizing may comprise positioning the stabilizer against the atrial side of the leaflets so as to reduce flail of the leaflets. In some embodiments, the stabilizer comprises an expandable member, a flap or at least one loop. When the device includes at least one loop, temporarily stabilizing may comprises positioning the at least one loop against the leaflets so as to reduce movement of the leaflets. In some embodiments, temporarily stabilizing further comprises moving the at least one loop along the leaflets toward the center of the valve so as to reduce movement of the leaflets. When the chamber comprises a ventricle including chordae extending from the ventricle to the valve leaflets, temporarily stabilizing may comprise holding the chordae with the device so as to reduce movement of the valve leaflets. When the device includes an expandable member, holding the chordae may comprise expanding the expandable member against the chordae. In some embodiments, temporarily stabilizing the valve leaflets comprises temporarily slowing the natural pace of the heart with a pacing instrument.

In a further aspect of the invention, a minimally invasive device is provided comprising at least one proximal element and at least one distal element configured for grasping tissue therebetween, and an indicator which indicates a presence or absence of tissue in a target area between the at least one proximal and distal elements. In some embodiments, the indicator comprises an enhanced visibility substance. For example, the enhanced visibility substance may be disposed on or within the at least one proximal and/or the at least one distal elements. The device may further comprise a reservoir within which the enhanced visibility substance is disposed. In some embodiments, the reservoir is configured to release at least a portion of the enhanced visibility substance due to the presence of tissue in the target area between the at least one proximal and distal elements. Alternatively or in addition, the reservoir may be configured to move locations due to the presence of tissue in the target area between the at least one proximal and distal elements. Or, the device may further comprise a conduit through which the enhanced visibility substance is injectable toward the target area.

In some embodiments, the indicator is configured to change shape and/or orientation based on a presence of tissue within the target area. For example, the indicator may be configured to extend into the target area in the absence of tissue within the target area and to change shape or orientation within the target area due to the presence of tissue within the target area. In some instances, the indicator comprises a floating block, a flap, a reservoir, a loop, a slackline, a probe, a detectable element, or a combination of any of these.

In other embodiments, the indicator comprises a sensor. Examples of sensors include a conductor, a strain gauge, a radiosensor, an optical sensor, an ultrasound sensor, a magnetic sensor, an electrical resistance sensor, an infrared sensor, an intravascular ultrasound sensor, a pressure sensor or a combination of any of these. Optionally, the indicator may be configured to contact the at least one distal element forming a closed circuit when the tissue is absent within the target area.

In another aspect of the present invention, a minimally invasive device is provided comprising at least one proximal element and at least one distal element configured for grasping tissue therebetween, and an adjustment element configured to adjust a position of the tissue between the at least one proximal and distal elements. In some embodiments, the adjustment element comprises a vacuum line configured to apply suction to the tissue to adjust the position of the tissue between the at least one proximal and distal elements. In other embodiments, the adjustment element comprises a secondary grasper configured to grasp the tissue to adjust the position of the tissue between the at least one proximal and distal elements. In still other embodiments, the adjustment element comprises a rotating component configured to move the tissue between the at least one proximal and distal elements. And, in yet other embodiments, the adjustment element is configured to adjust a position of the at least one proximal element so as to move the tissue in relation to the at least one distal element.

In a further aspect of the present invention, a minimally invasive device is provided comprising at least one proximal element and at least one distal element configured for grasping tissue therebetween, and a stabilizer configured to reduce movement of the tissue prior to grasping the tissue between the at least one proximal and distal elements. When the tissue comprises a leaflet of a mitral valve, the stabilizer may comprise an expandable member, a flap, an overtube or at least one loop configured to be positioned against an atrial side of the leaflets so as to reduce flail of the leaflets. For example, the stabilizer may comprise at least one loop which is moveable toward a center of the valve so as to reduce movement of the leaflet. When the tissue comprises a leaflet having chordae extending therefrom, the stabilizer may comprise an expandable member configured to hold the chordae upon expansion so as to reduce movement of the leaflet.

In another aspect of the present invention, a system is provided for assessing quality of fixation of a tissue within a body comprising a fixation device having at least one proximal element and at least one distal element configured for grasping tissue therebetween, a catheter having a proximal end, a distal end and a lumen therethrough, the catheter configured for endoluminal advancement through at least a portion of the body to the tissue, and a shaft removably coupled to the fixation device. The shaft is configured to pass through the lumen of the catheter, and at least a portion of the shaft is flexible to allow movement of the fixation device relative to the catheter while the tissue is grasped between the at least one proximal element and the at least one distal element. In some embodiments, the shaft comprises a compression coil. Thus, the system may further include a center actuation wire configured to extend through the compression coil so as to rigidify the coil during placement of the fixation device. Optionally, the system may include a sheath extendable over at least a portion of the flexible shaft so as to rigidify the shaft during placement of the fixation device. Such rigidifying elements are then removed to allow movement of the fixation device while the tissue is grasped to evaluate the desirability of the fixation.

In another aspect of the present invention, a method of fixing a pair of valve leaflets together along their coaptation line is provided. The method comprises fixing the pair of valve leaflets together at a first location along the coaptation line with a first fixation device, and fixing the pair of valve leaflets together at a second location along the coaptation line with a second fixation device, wherein the first and second locations differ. In some embodiments, the first and second locations are adjacent to each other. Or, the first and second locations may be spaced apart, such as approximately 1 cm apart. The first and second locations may be positioned so as to provide a single orifice, double orifice or triple orifice geometry, to name a few, when a pressure gradient opens the pair of valve leaflets.

In some embodiments, the first fixation device has a first pair of grasping elements and a second pair of grasping elements. Thus, fixing the pair of valve leaflets together at the first location may comprise grasping one leaflet of the pair of valve leaflets between the first pair of grasping elements and grasping another leaflet of the pair of valve leaflets between the second pair of grasping elements. And, fixing the pair of valve leaflets together at the second location may comprise grasping one leaflet of the pair of valve leaflets between the first pair of grasping elements of the second fixation device and grasping another leaflet of the pair of valve leaflets between the second pair of grasping elements of the second fixation device. In some embodiments, the method further comprises assessing performance of the valve leaflets after the step of fixing the pair of valve leaflets together at the first location to determine need for the step of fixing the pair of valve leaflets together at the second location.

Other objects and advantages of the present invention will become apparent from the detailed description to follow, together with the accompanying drawings.

BRIEF DESCRIPTION OF THE DRAWINGS

FIGS. 19A-19C illustrate an embodiment of a fixation device adapted for use with a pre-grasper.

FIG. 23 illustrates an embodiment of a fixation device having suction to maintain leaflet position after grasping.

FIGS. 24A-24B illustrate an embodiment of a fixation device having extended frictional accessories.

FIGS. 25A-25B illustrate an embodiment of a fixation device having a textured gripping surface.

FIG. 26A-26B illustrate an embodiment of a fixation device having a gripping surface which penetrates and holds the grasped leaflets within the fixation device.

DETAILED DESCRIPTION OF THE INVENTION

Figure 1A:
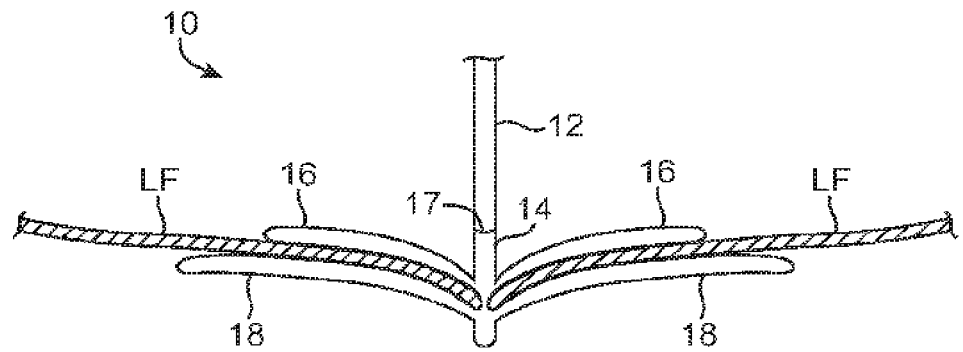
FIGS. 1A-1C illustrate grasping of the leaflets with a fixation device, inversion of the distal elements of the fixation device and removal of the fixation device, respectively.

The present invention provides devices, systems and methods for stabilizing and grasping tissues such as valve leaflets, assessing the grasp of these tissues, approximating and fixating the tissues, and assessing the fixation of the tissues to treat cardiac valve regurgitation, particularly mitral valve regurgitation.

Grasping will preferably be atraumatic providing a number of benefits. By atraumatic, it is meant that the devices and methods of the invention may be applied to the valve leaflets and then removed without causing any significant clinical impairment of leaflet structure or function. The leaflets and valve continue to function substantially the same as before the invention was applied. Thus, some minor penetration or denting of the leaflets may occur using the invention while still meeting the definition of "atraumatic". This enables the devices of the invention to be applied to a diseased valve and, if desired, removed or repositioned without having negatively affected valve function. In addition, it will be understood that in some cases it may be necessary or desirable to pierce or otherwise permanently affect the leaflets during either grasping, fixing or both. In addition, once a leaflet is grasped, it may be desirable to further incorporate leaflet tissue to ensure that the initial grasp will result in secure tissue fixation. Furthermore, it may be desirable once the leaflet is grasped to provide the user with feedback that sufficient leaflet is incorporated, and/or to provide the user an indication of the resulting placement, both prior to releasing the fixation device thereby allowing repositioning or correction of the placement if desired.

It may be appreciated that each the steps of stabilizing, grasping, approximating, fixating and assessing may be accomplished by a separate device or a plurality of steps may be accomplished by a single device. In some embodiments, all of the steps may be achieved by a single device. Further, in some embodiments, steps are provided by separate devices which approach the tissue from different directions. For example, when treating a mitral valve, some devices may use an atrial approach while other devices use a ventricular approach. Although a number of embodiments are provided to achieve these results, a general overview of the basic features will be presented herein. Such features are not intended to limit the scope of the invention and are presented with the aim of providing a basis for descriptions of individual embodiments presented later in the application.

I. Fixation Device Overview

Many of the devices, systems and methods of the present invention utilize or are utilized in conjunction with a preferred embodiment of a fixation device described herein and in U.S. Pat. No. 6,629,534 and U.S. patent application Ser.

Nos. 10/441,531, 11/130,818, 10/975,555, all of which are incorporated herein by reference for all purposes. The fixation device is provided by an interventional tool that is positioned near a desired treatment site and used to grasp the target tissue. In endovascular applications, the interventional tool is typically an interventional catheter. In surgical applications, the interventional tool is typically an interventional instrument. In preferred embodiments, fixation of the grasped tissue is accomplished by maintaining grasping with a portion of the interventional tool which is left behind as an implant. While the invention may have a variety of applications for tissue approximation and fixation throughout the body, it is particularly well adapted for the repair of valves, especially cardiac valves such as the mitral valve.

Referring to FIG. 1A, an interventional tool 10, having a delivery device, such as a shaft 12, and a fixation device 14, is illustrated having approached the mitral valve MV from the atrial side and grasped the leaflets LF. The mitral valve may be accessed either surgically or by using endovascular techniques, and either by a retrograde approach through the ventricle or by an antegrade approach through the atrium, as described above. For illustration purposes, an antegrade approach is described.

The fixation device 14 is releasably attached to the shaft 12 of the interventional tool 10 at its distal end. When describing the devices of the invention herein, "proximal" shall mean the direction toward the end of the device to be manipulated by the user outside the patient's body, and "distal" shall mean the direction toward the working end of the device that is positioned at the treatment site and away from the user. With respect to the mitral valve, proximal shall refer to the atrial or upstream side of the valve leaflets and distal shall refer to the ventricular or downstream side of the valve leaflets.

The fixation device 14 typically comprises proximal elements 16 (or gripping elements) and distal elements 18 (or fixation elements) which protrude radially outward and are positionable on opposite sides of the leaflets LF as shown so as to capture or retain the leaflets therebetween. The proximal elements 16 are preferably comprised of cobalt chromium, nitinol or stainless steel, and the distal elements 18 are preferably comprised of cobalt chromium alloy (such as Elgiloy®) or stainless steel, however any suitable materials may be used. The fixation device 14 is coupleable to the shaft 12 by a coupling mechanism 17. The coupling mechanism 17 allows the fixation device 14 to detach and be left behind as an implant to hold the leaflets together in the coapted position.

Figure 1B:
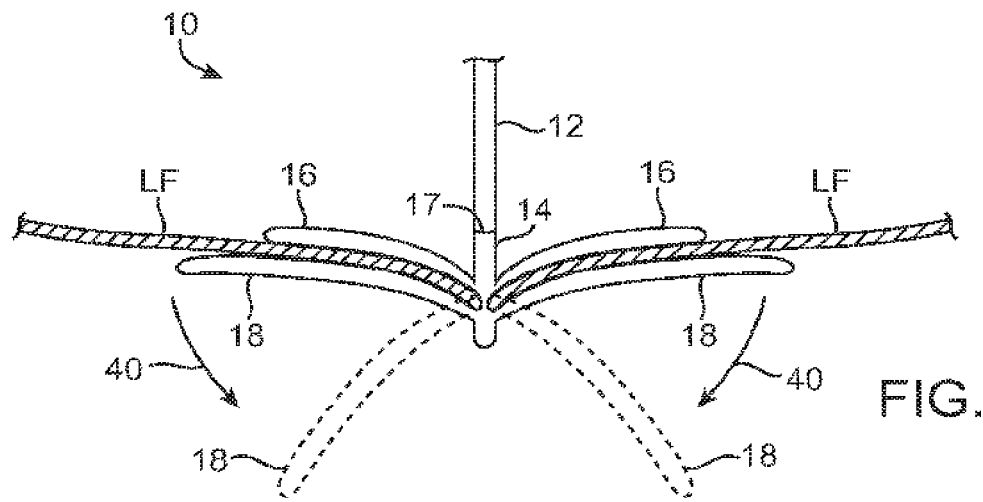
Figure 1C:
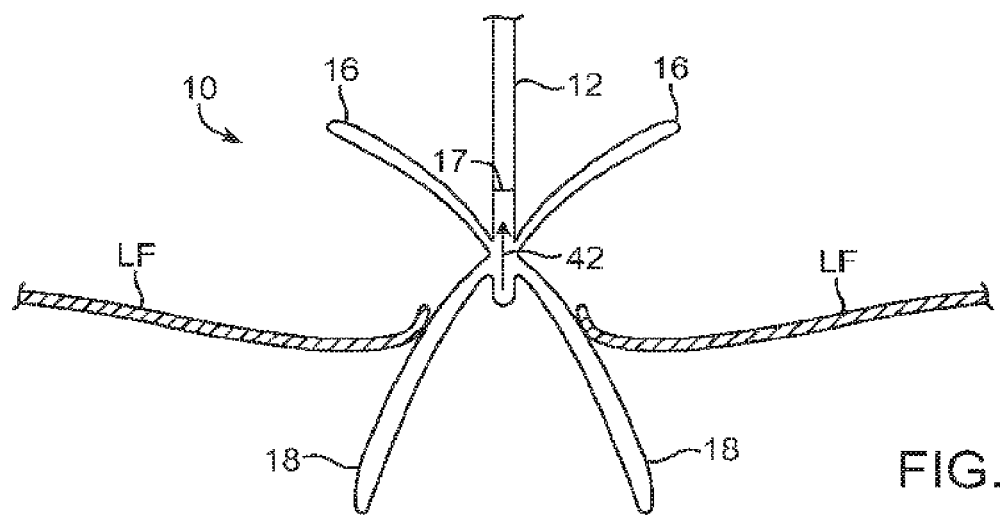

In some situations, it may be desired to reposition or remove the fixation device 14 after the proximal elements 16, distal elements 18, or both have been deployed to capture the leaflets LF. Such repositioning or removal may be desired for a variety of reasons, such as to reapproach the valve in an attempt to achieve better valve function, more optimal positioning of the device 14 on the leaflets, better purchase on the leaflets, to detangle the device 14 from surrounding tissue such as chordae, to exchange the device 14 with one having a different design, or to abort the fixation procedure, to name a few. To facilitate repositioning or removal of the fixation device 14 the distal elements 18 are releasable and optionally invertible to a configuration suitable for withdrawal of the device 14 from the valve without tangling or interfering with or damaging the chordae, leaflets or other tissue. FIG. 1B illustrates inversion wherein the distal elements 18 are moveable in the direction of arrows 40 to an inverted position. Likewise, the proximal elements 16 may be raised, if desired. In the inverted position, the device 14 may be repositioned to a desired orientation wherein the distal elements may then be reverted to a grasping position against the leaflets as in FIG. 1A. Alternatively, the fixation device 14 may be withdrawn (indicated by arrow 42) from the leaflets as shown in FIG. 1C. Such inversion reduces trauma to the leaflets and minimizes any entanglement of the device with surrounding tissues. Once the device 14 has been withdrawn through the valve leaflets, the proximal and distal elements may be moved to a closed position or configuration suitable for removal from the body or for reinsertion through the mitral valve.

Figure 2A:
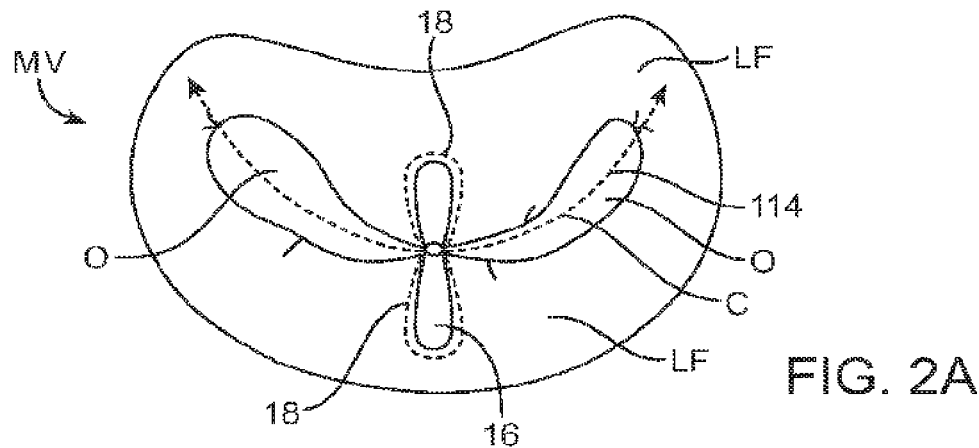
FIG. 2A-2E illustrate example positions of fixation devices in desired orientations relative to the leaflets.
Figure 2B:
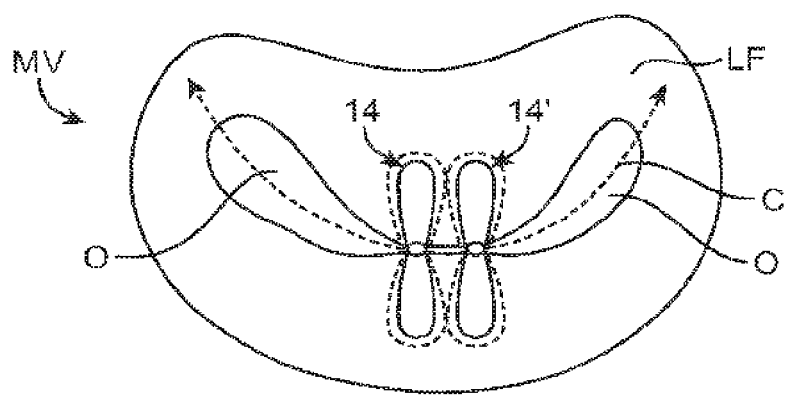
Figure 2C:
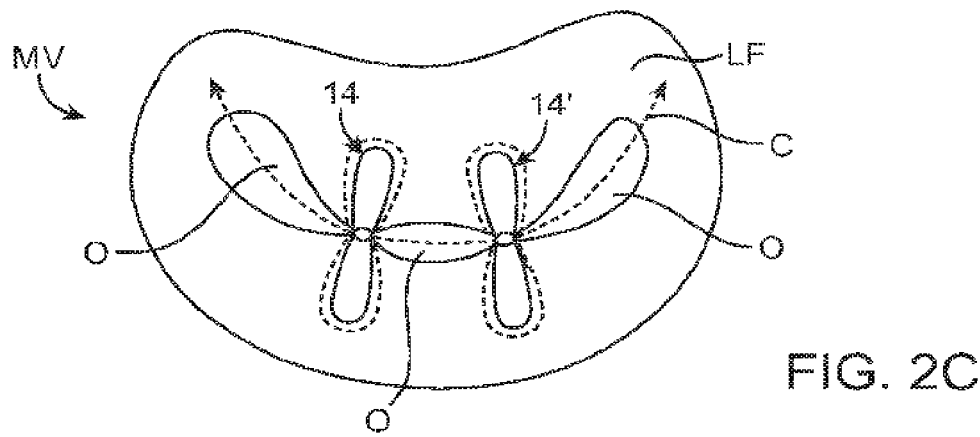
Figure 2D:
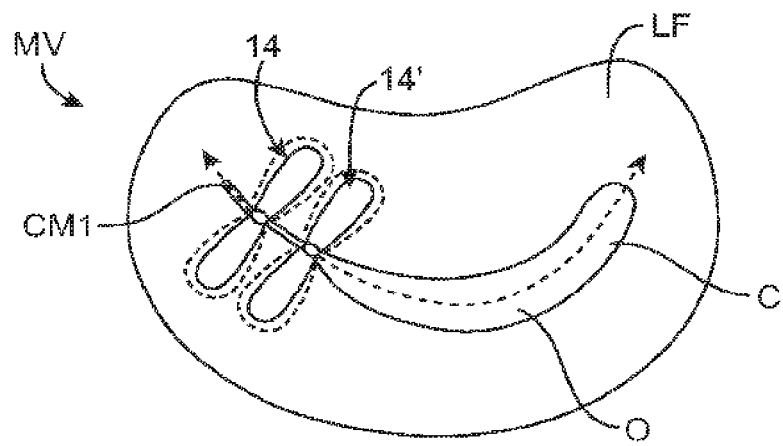
Figure 2E:
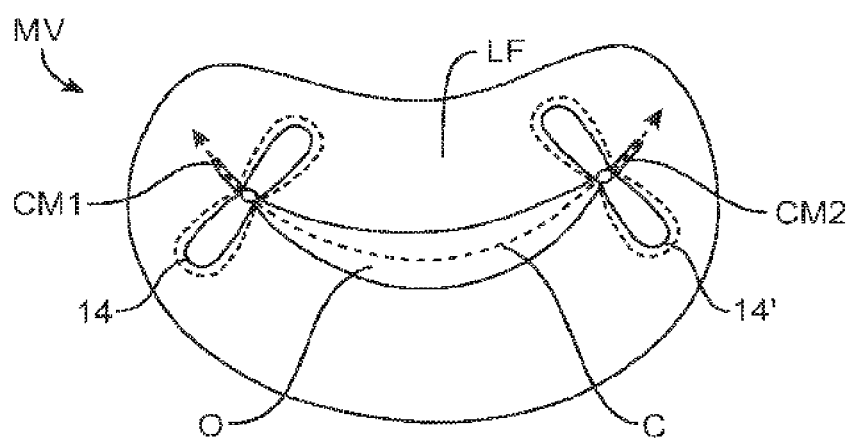

FIGS. 2A-2C illustrate example positions of one or more fixation devices 14 in desired orientations in relation to the leaflets LF. These are short-axis views of the mitral valve MV from the atrial side, therefore, the proximal elements 16 are shown in solid line and the distal elements 18 are shown in dashed line. The proximal and distal elements 16, 18 are typically positioned to be substantially perpendicular to the line of coaptation C. The devices 14 may be moved roughly along the line of coaptation to any desired location for fixation. The leaflets LF are held in place so that during diastole, as shown in FIG. 2A-2C, the leaflets LF remain in position between the elements 16, 18 surrounded by openings O which result from the diastolic pressure gradient. Advantageously, leaflets LF are coapted such that their proximal or upstream surfaces are facing each other in a vertical orientation, parallel to the direction of blood flow through mitral valve MV. The upstream surfaces may be brought together so as to be in contact with one another or may be held slightly apart, but will preferably be maintained in the vertical orientation in which the upstream surfaces face each other at the point of coaptation. Referring to FIG. 2A, the placement of one fixation device near the center of the leaflets LF simulates the double orifice geometry of a standard surgical bow-tie repair. Color Doppler echo will show if the regurgitation of the valve has been reduced. If the resulting mitral flow pattern is satisfactory, the leaflets may be fixed together in this orientation. If the resulting color Doppler image shows insufficient improvement in mitral regurgitation, the interventional tool 10 may be repositioned. This may be repeated until an optimal result is produced wherein the leaflets LF are held in place. Once the leaflets are coapted in the desired arrangement, the fixation device 14 is then detached from the shaft 12 and left behind as an implant to hold the leaflets together in the coapted position. It may be desired to add an additional fixation element 14', such as illustrated in FIGS. 2B-2E. In FIG. 2B, the additional fixation element 14' is positioned beside the previously place fixation element 14 retaining the double orifice geometry. In FIG. 2C, the additional fixation element 14' is positioned a distance, such as up to 1 cm, from the previously placed fixation element 14 creating a triple orifice geometry. In FIG. 2D, the fixation elements 14, 14' are positioned adjacent to each other near a first commissure CM1. Such arrangement creates generally a single orifice geometry by plicating on one side of the valve opening. Likewise, as shown in FIG. 2E, one fixation element 14 may be positioned near the first commissure CM1 and an additional fixation element 14' may be positioned near a second commissure CM2. Such arrangement also creates generally a single orifice geometry by plicating on either side of the valve opening. The additional fixation element 14' may be desired to ensure adequate fixation of the leaflets LF and/or to further reposition the leaflets LF. The additional fixation element 14' may be added at any time during the procedure or at a separate procedure at a later point in time. It may be appreciated that any number of fixation elements 14 may be positioned to fixate the leaflets or any other tissue, including two, three, four, five or more fixation elements 14.

Figure 3:
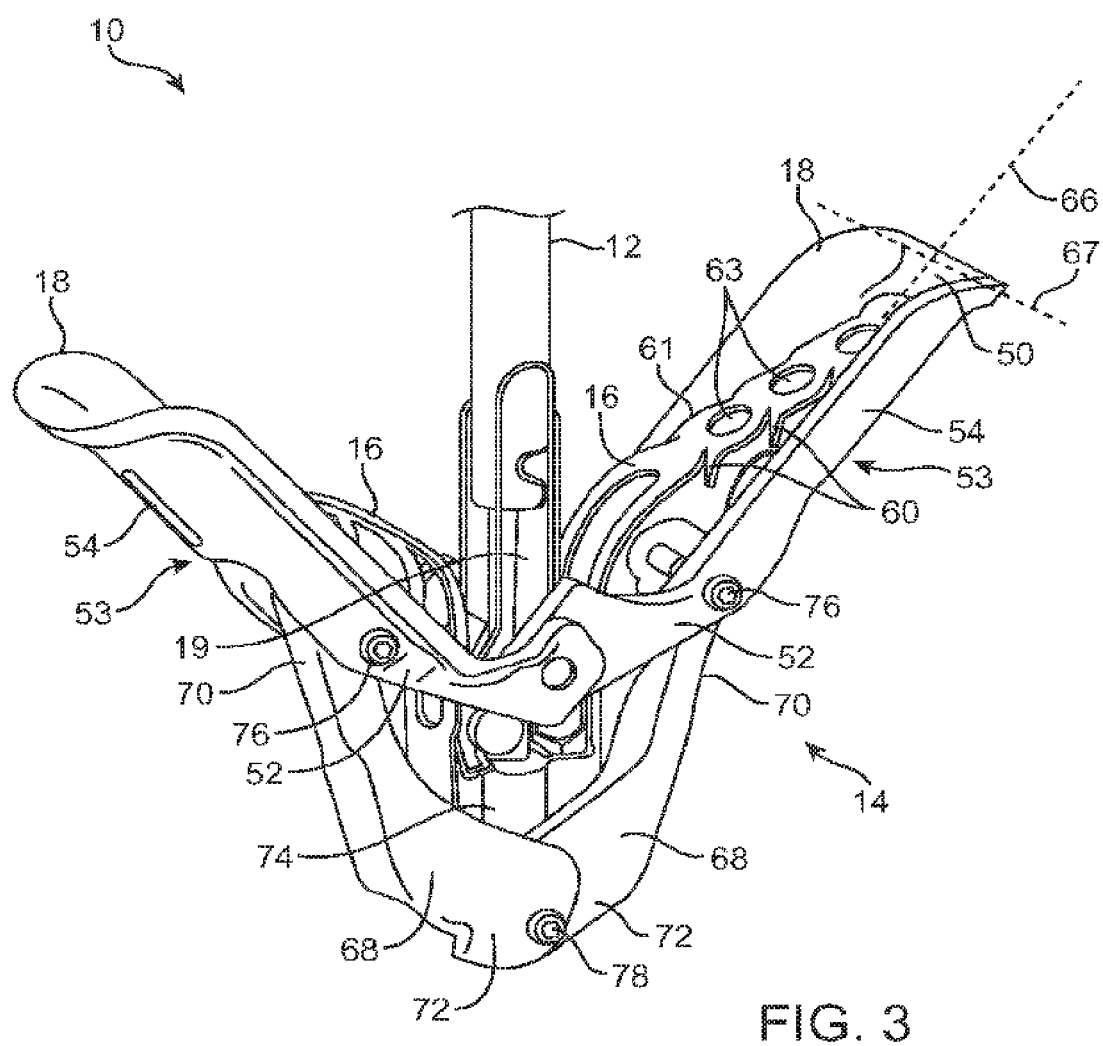
FIGS. 3, 4A-4B, 5A-5B, 6A-6B, 7A-7B illustrate an embodiment of a fixation device in various positions.

FIG. 3 illustrates an embodiment of a fixation device 14. Here, the fixation device 14 is shown coupled to a shaft 12 to form an interventional tool 10. The fixation device 14 includes a coupling member 19 and a pair of opposed distal elements 18. The distal elements 18 comprise elongate arms 53, each arm having a proximal end 52 rotatably connected to the coupling member 19 and a free end 54. The free ends 54 have a rounded shape to minimize interference with and trauma to surrounding tissue structures. Preferably, each free end 54 defines a curvature about two axes, one being a longitudinal axis 66 of arms 53. Thus, engagement surfaces 50 have a cupped or concave shape to surface area in contact with tissue and to assist in grasping and holding the valve leaflets. This further allows arms 53 to nest around the shaft 12 in a closed position to minimize the profile of the device. Preferably, arms 53 are at least partially cupped or curved inwardly about their longitudinal axes 66. Also, preferably, each free end 54 defines a curvature about an axis 67 perpendicular to longitudinal axis 66 of arms 53. This curvature is a reverse curvature along the most distal portion of the free end 54. Likewise, the longitudinal edges of the free ends 54 may flare outwardly. Both the reverse curvature and flaring minimize trauma to the tissue engaged therewith. Arms 53 further include a plurality of openings to enhance grip and to promote tissue ingrowth following implantation.

The valve leaflets are grasped between the distal elements 18 and proximal elements 16. In some embodiments, the proximal elements 16 are flexible, resilient, and cantilevered from coupling member 19. The proximal elements are preferably resiliently biased toward the distal elements. Each proximal element 16 is shaped and positioned to be at least partially recessed within the concavity of the distal element 18 when no tissue is present. When the fixation device 14 is in the open position, the proximal elements 16 are shaped such that each proximal element 16 is separated from the engagement surface 50 near the proximal end 52 of arm 53 and slopes toward the engagement surface 50 near the free end 54 with the free end of the proximal element contacting engagement surface 50, as illustrated in FIG. 3. This shape of the proximal elements 16 accommodates valve leaflets or other tissues of varying thicknesses.

Proximal elements 16 may include a plurality of openings 63 and scalloped side edges 61 to increase grip on tissue. The proximal elements 16 optionally include frictional accessories, frictional features or grip-enhancing elements to assist in grasping and/or holding the leaflets. In preferred embodiments, the frictional accessories comprise barbs 60 having tapering pointed tips extending toward engagement surfaces 50. It may be appreciated that any suitable frictional accessories may be used, such as prongs, windings, bands, barbs, grooves, channels, bumps, surface roughening, sintering, high-friction pads, coverings, coatings or a combination of these. Optionally, magnets may be present in the proximal and/or distal elements. It may be appreciated that the mating surfaces will be made from or will include material of opposite magnetic charge to cause attraction by magnetic force. For example, the proximal elements and distal elements may each include magnetic material of opposite charge so that tissue is held under constant compression between the proximal and distal elements to facilitate faster healing and ingrowth of tissue. Also, the magnetic force may be used to draw the proximal elements 16 toward the distal elements 18, in addition to or alternatively to biasing of the proximal elements toward the distal elements. This may assist in deployment of the proximal elements 16.

In another example, the distal elements 18 each include magnetic material of opposite charge so that tissue positioned between the distal elements 18 is held therebetween by magnetic force.

The fixation device 14 also includes an actuation mechanism 58. In this embodiment, the actuation mechanism 58 comprises two link members or legs 68, each leg 68 having a first end 70 which is rotatably joined with one of the distal elements 18 at a riveted joint 76 and a second end 72 which is rotatably joined with a stud 74. The legs 68 are preferably comprised of a rigid or semi-rigid metal or polymer such as Elgiloy®, cobalt chromium or stainless steel, however any suitable material may be used. While in the embodiment illustrated both legs 68 are pinned to stud 74 by a single rivet 78, it may be appreciated, however, that each leg 68 may be individually attached to the stud 74 by a separate rivet or pin. The stud 74 is joinable with an actuator rod 64 (not shown) which extends through the shaft 12 and is axially extendable and retractable to move the stud 74 and therefore the legs 68 which rotate the distal elements 18 between closed, open and inverted positions. Likewise, immobilization of the stud 74 holds the legs 68 in place and therefore holds the distal elements 18 in a desired position. The stud 74 may also be locked in place by a locking feature.

In any of the embodiments of fixation device 14 disclosed herein, it may be desirable to provide some mobility or flexibility in distal elements 18 and/or proximal elements 16 in the closed position to enable these elements to move or flex with the opening or closing of the valve leaflets. This provides shock absorption and thereby reduces force on the leaflets and minimizes the possibility for tearing or other trauma to the leaflets. Such mobility or flexibility may be provided by using a flexible, resilient metal or polymer of appropriate thickness to construct the distal elements 18. Also, the locking mechanism of the fixation device (described below) may be constructed of flexible materials to allow some slight movement of the proximal and distal elements even when locked. Further, the distal elements 18 can be connected to the coupling mechanism 19 or to actuation mechanism 58 by a mechanism that biases the distal element into the closed position (inwardly) but permits the arms to open slightly in response to forces exerted by the leaflets. For example, rather than being pinned at a single point, these components may be pinned through a slot that allowed a small amount of translation of the pin in response to forces against the arms. A spring is used to bias the pinned component toward one end of the slot.

Figure 4A:
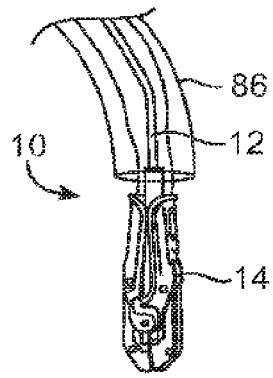
Figure 4B:
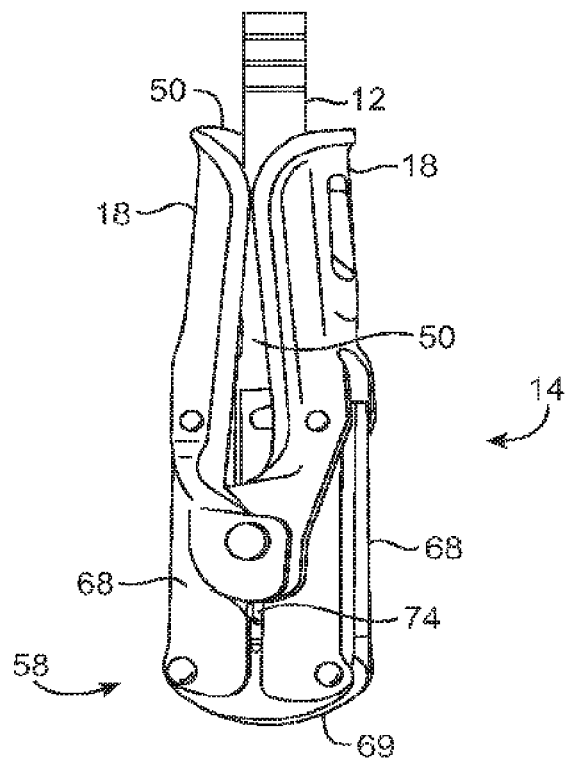

FIGS. 4A-4B, 5A-5B, 6A-6B, 7A-7B illustrate embodiments of the fixation device 14 of FIG. 3 in various possible positions during introduction and placement of the device 14 within the body to perform a therapeutic procedure. FIG. 4A illustrates an embodiment of an interventional tool 10 delivered through a catheter 86. It may be appreciated that the interventional tool 10 may take the form of a catheter, and likewise, the catheter 86 may take the form of a guide catheter or sheath. However, in this example the terms interventional tool 10 and catheter 86 will be used. The interventional tool 10 comprises a fixation device 14 coupled to a shaft 12 and the fixation device 14 is shown in the closed position. FIG. 4B illustrates a similar embodiment of the fixation device of FIG. 4A in a larger view. In the closed position, the opposed pair of distal elements 18 are positioned so that the engagement surfaces 50 face each other. Each distal element 18 comprises an elongate arm 53 having a cupped or concave shape so that together the arms 53 surround the shaft 12 and optionally contact each other on opposite sides of the shaft. This provides a low profile for the fixation device 14 which is readily passable through the catheter 86 and through any anatomical structures, such as the mitral valve. In addition, FIG. 4B further includes an actuation mechanism 58. In this embodiment, the actuation mechanism 58 comprises two legs 68 which are each movably coupled to a base 69. The base 69 is joined with an actuator rod 64 which extends through the shaft 12 and is used to manipulate the fixation device 14. In some embodiments, the actuator rod 64 attaches directly to the actuation mechanism 58, particularly the base 69. However, the actuator rod 64 may alternatively attach to a stud 74 which in turn is attached to the base 69. In some embodiments, the stud 74 is threaded so that the actuator rod 64 attaches to the stud 74 by a screw-type action. However, the rod 64 and stud 74 may be joined by any mechanism which is releasable to allow the fixation device 14 to be detached from shaft 12.

Figure 5A:
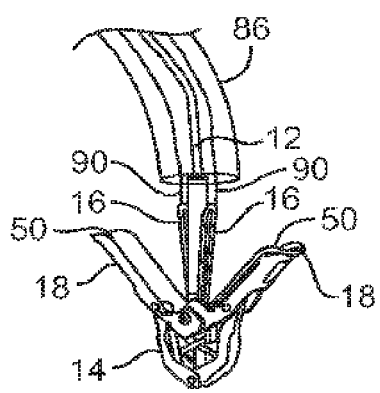
Figure 5B:
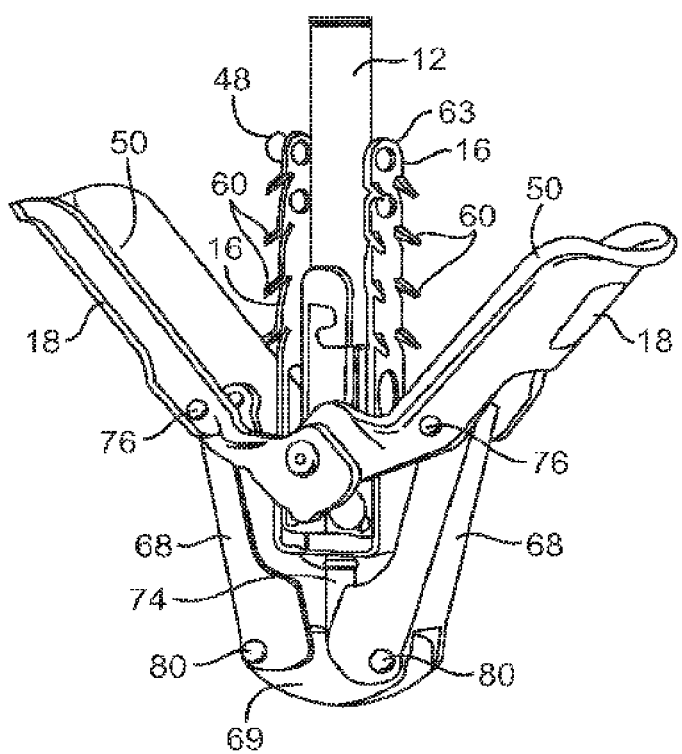

FIGS. 5A-5B illustrate the fixation device 14 in the open position. In the open position, the distal elements 18 are rotated so that the engagement surfaces 50 face a first direction. Distal advancement of the stud 74 relative to coupling member 19 by action of the actuator rod 64 applies force to the distal elements 18 which begin to rotate around joints 76 due to freedom of movement in this direction. Such rotation and movement of the distal elements 18 radially outward causes rotation of the legs 68 about joints 80 so that the legs 68 are directly slightly outwards. The stud 74 may be advanced to any desired distance correlating to a desired separation of the distal elements 18. In the open position, engagement surfaces 50 are disposed at an acute angle relative to shaft 12, and are preferably at an angle of between 90 and 180 degrees relative to each other. In one embodiment, in the open position the free ends 54 of arms 53 have a span therebetween of about 10-20 mm, usually about 12-18 mm, and preferably about 14-16 mm.

Proximal elements 16 are typically biased outwardly toward arms 53. The proximal elements 16 may be moved inwardly toward the shaft 12 and held against the shaft 12 with the aid of proximal element lines 90 which can be in the form of sutures, wires, nitinol wire, rods, cables, polymeric lines, or other suitable structures. The proximal element lines 90 may be connected with the proximal elements 16 by threading the lines 90 in a variety of ways. When the proximal elements 16 have a loop shape, as shown in FIG. 5A, the line 90 may pass through the loop and double back. When the proximal elements 16 have an elongate solid shape, as shown in FIG. 5B, the line 90 may pass through one or more of the openings 63 in the element 16. Further, a line loop 48 may be present on a proximal element 16, also illustrated in FIG. 5B, through which a proximal element line 90 may pass and double back. Such a line loop 48 may be useful to reduce friction on proximal element line 90 or when the proximal elements 16 are solid or devoid of other loops or openings through which the proximal element lines 90 may attach. A proximal element line 90 may attach to the proximal elements 16 by detachable means which would allow a single line 90 to be attached to a proximal element 16 without doubling back and would allow the single line 90 to be detached directly from the proximal element 16 when desired. Examples of such detachable means include hooks, snares, clips or breakable couplings, to name a few. By applying sufficient tension to the proximal element line 90, the detachable means may be detached from the proximal element 16 such as by breakage of the coupling. Other mechanisms for detachment may also be used. Similarly, a lock line 92 may be attached and detached from a locking mechanism by similar detachable means.

In the open position, the fixation device 14 can engage the tissue which is to be approximated or treated. This embodiment is adapted for repair of the mitral valve using an antegrade approach from the left atrium. The interventional tool 10 is advanced through the mitral valve from the left atrium to the left ventricle. The distal elements 18 are oriented to be perpendicular to the line of coaptation and then positioned so that the engagement surfaces 50 contact the ventricular surface of the valve leaflets, thereby grasping the leaflets. The proximal elements 16 remain on the atrial side of the valve leaflets so that the leaflets lie between the proximal and distal elements. In this embodiment, the proximal elements 16 have frictional accessories, such as barbs 60 which are directed toward the distal elements 18. However, neither the proximal elements 16 nor the barbs 60 contact the leaflets at this time.

The interventional tool 10 may be repeatedly manipulated to reposition the fixation device 14 so that the leaflets are properly contacted or grasped at a desired location. Repositioning is achieved with the fixation device in the open position. In some instances, regurgitation may also be checked while the device 14 is in the open position. If regurgitation is not satisfactorily reduced, the device may be repositioned and regurgitation checked again until the desired results are achieved.

Figure 6A:
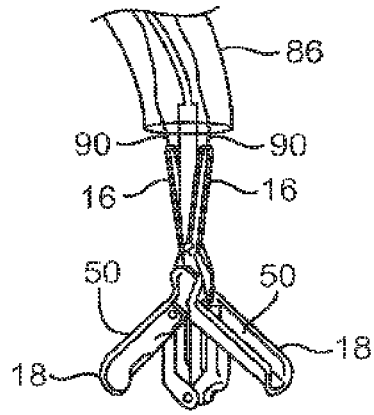
Figure 6B:
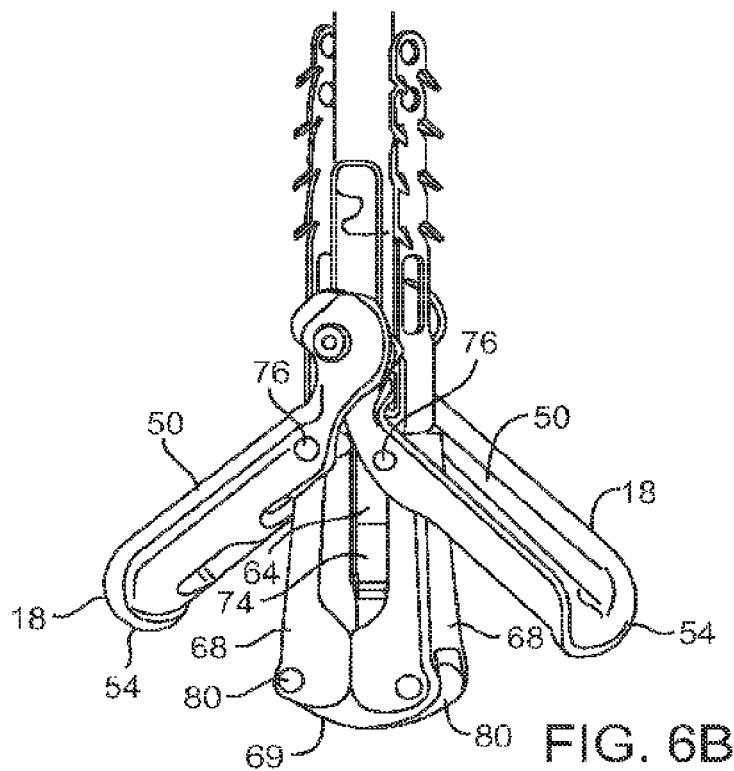

It may also be desired to invert the fixation device 14 to aid in repositioning or removal of the fixation device 14. FIGS. 6A-6B illustrate the fixation device 14 in the inverted position. By further advancement of stud 74 relative to coupling member 19, the distal elements 18 are further rotated so that the engagement surfaces 50 face outwardly and free ends 54 point distally, with each arm 53 forming an obtuse angle relative to shaft 12. The angle between arms 53 is preferably in the range of about 270 to 360 degrees. Further advancement of the stud 74 further rotates the distal elements 18 around joints 76. This rotation and movement of the distal elements 18 radially outward causes rotation of the legs 68 about joints 80 so that the legs 68 are returned toward their initial position, generally parallel to each other. The stud 74 may be advanced to any desired distance correlating to a desired inversion of the distal elements 18. Preferably, in the fully inverted position, the span between free ends 54 is no more than about 20 mm, usually less than about 16 mm, and preferably about 12-14 mm. In this illustration, the proximal elements 16 remain positioned against the shaft 12 by exerting tension on the proximal element lines 90. Thus, a relatively large space may be created between the elements 16, 18 for repositioning. In addition, the inverted position allows withdrawal of the fixation device 14 through the valve while minimizing trauma to the leaflets. Engagement surfaces 50 provide an atraumatic surface for deflecting tissue as the fixation device is retracted proximally. It should be further noted that barbs 60 are angled slightly in the distal direction (away from the free ends of the proximal elements 16), reducing the risk that the barbs will catch on or lacerate tissue as the fixation device is withdrawn.

Figure 7A:
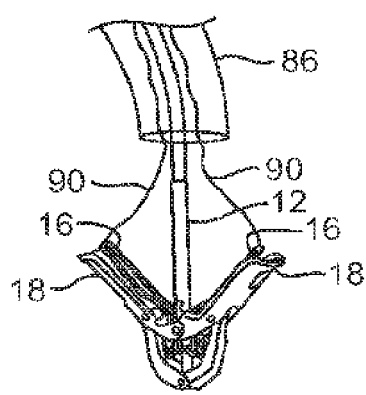
Figure 7B:
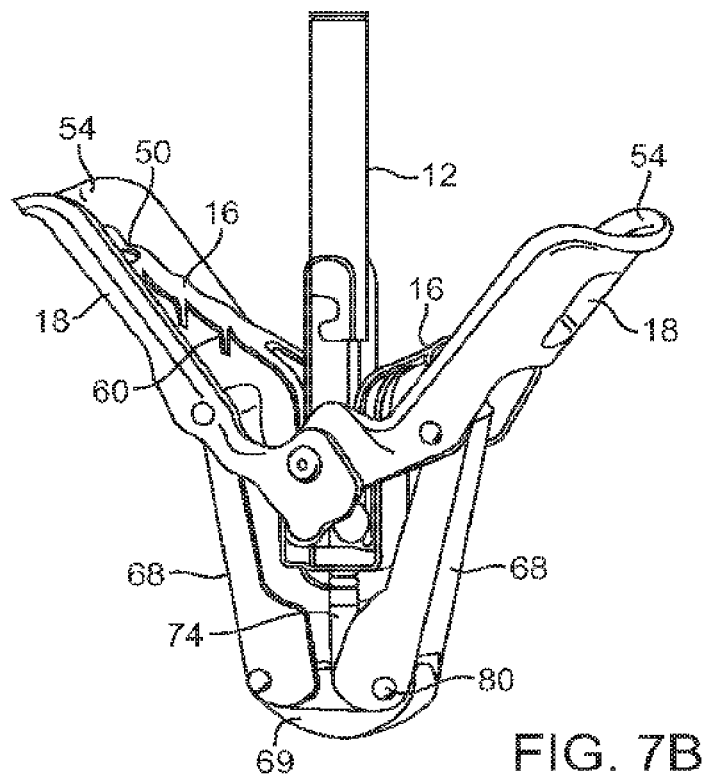

Once the fixation device 14 has been positioned in a desired location against the valve leaflets, the leaflets may then be captured between the proximal elements 16 and the distal elements 18. FIGS. 7A-7B illustrate the fixation device 14 in such a position. Here, the proximal elements 16 are lowered toward the engagement surfaces 50 so that the leaflets are held therebetween. In FIG. 7B, the proximal elements 16 are shown to include barbs 60 which may be used to provide atraumatic gripping of the leaflets. Alternatively, larger, more sharply pointed barbs or other penetration structures may be used to pierce the leaflets to more actively assist in holding them in place. This position is similar to the open position of FIGS. 5A-5B, however the proximal elements 16 are now lowered toward arms 53 by releasing tension on proximal element lines 90 to compress the leaflet tissue therebetween. At any time, the proximal elements 16 may be raised and the distal elements 18 adjusted or inverted to reposition the fixation device 14, if regurgitation is not sufficiently reduced.

After the leaflets have been captured between the proximal and distal elements 16, 18 in a desired arrangement, the distal elements 18 may be locked to hold the leaflets in this position or the fixation device 14 may be returned to or toward a closed position.

It may be appreciated that the fixation devices 14 of the present invention may have any or all of the above described functions and features. For example, the fixation devices 14 may or may not be moveable to an inverted position. Or, the fixation devices 14 may or may not include proximal elements 16. Thus, the above described aspects of the fixation devices 14 are simply preferred embodiments and are not intended to limit the scope of the present invention.

II. Stabilization of Leaflets

A variety of devices and techniques are provided to stabilize the leaflets prior to grasping. Such stabilization is aimed to assist in effectively and efficiently grasping the leaflets thereby increasing the likelihood that the desired amount of leaflet will be incorporated into the fixation device without necessitating multiple grasps. It may be appreciated that the stabilization devices and techniques may be used in combination with the above described fixation device or may be used with any suitable grasping and/or fixing device. Further, many of such stabilization techniques and devices may be used to stabilize valve leaflets, or other tissues, for any purpose.

Figure 8A:
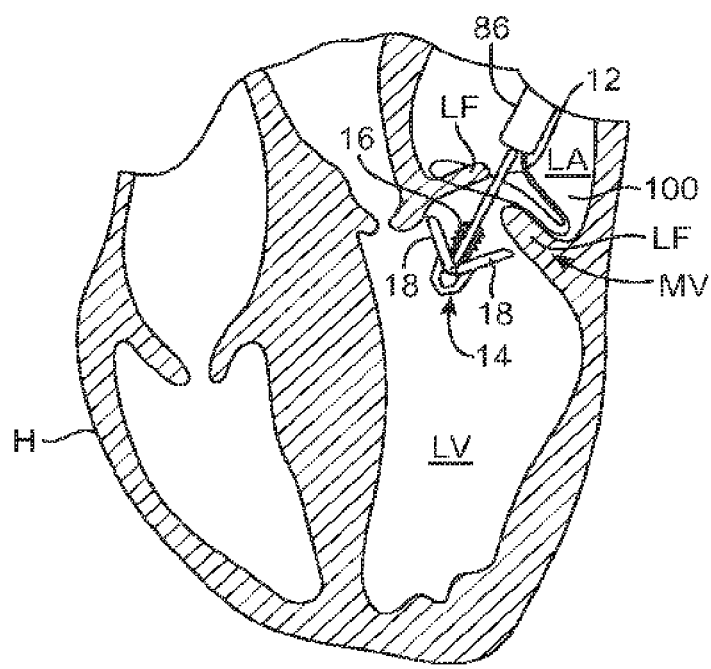
FIGS. 8A-8L, 9A-9B, 10A-10B, 11A-11B illustrate embodiments of devices which stabilize the valve leaflets by reducing upward mobility and flailing of the leaflets.

Typically in cases of mitral valve regurgitation, a portion of the leaflet LF is moving out of phase with the other leaflets or portions of the leaflets. This can occur due to an elongation or disconnection of the structures (chordae tendinae) holding the leaflets stable and in synchrony. Such a malfunction can lead to one leaflet or portion of a leaflet to swing or "flail" above the level of healthy coaptation, thereby allowing blood to regurgitate into the right atrium. FIGS. 8A-8L, 9A-9B, 10A-10B illustrate embodiments of devices which stabilize the valve leaflets by reducing upward mobility and flailing of the leaflets thereby allowing the user to more reliably grasp the targeted leaflets. In these embodiments, a catheter 86 is advanced into a left atrium LA of a heart H, as illustrated in FIG. 8A, and a fixation device 14 is advanced through the catheter 86 and through a mitral valve MV having leaflets LF so that at least a portion of the fixation device 14 is positioned within a left ventricle LV. The valve leaflets LF are shown flailing upwards toward the left atrium LA while the fixation device 14 resides below the valve, within the left ventricle LV. In this example, the fixation device 14 resembles the fixation device described above in relation to FIG. 3 and includes proximal elements 16 and distal elements 18. The fixation device 14 is at least partially opened to extend the distal elements 18 radially outwardly while the proximal elements 16 remain held against the shaft 12. It is desired to engage the leaflets LF with the distal elements 18 so that the proximal elements 16 may be lowered grasping the leaflets LF therebetween.

Figure 8B:
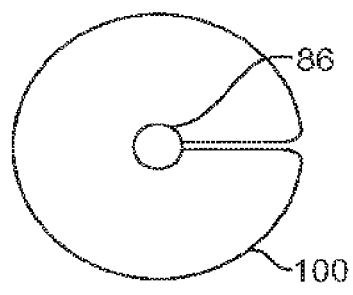
Figure 8C:
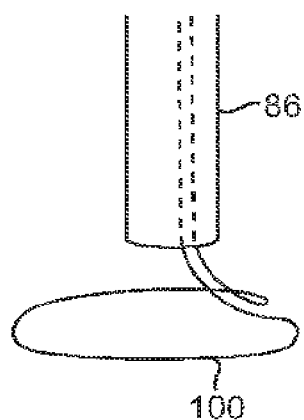
Figure 8D:
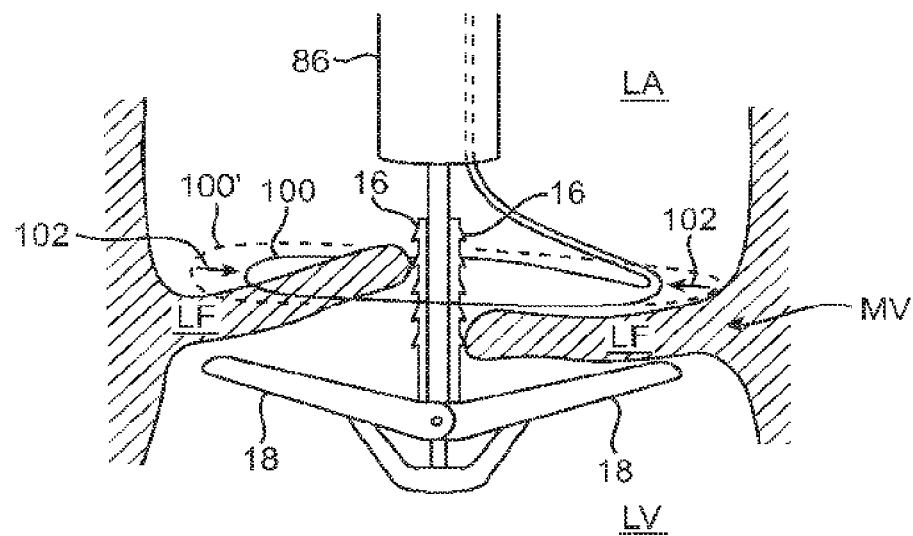

One or more stabilizing loops 100 may be advanced from the catheter 86 and positioned against the atrial side of the leaflets LF. FIG. 8B illustrates a cross-sectional top view of an embodiment of a stabilizing loop 100. The loop 100 is shown extending radially outwardly from the catheter 86 to form a circular shape. The diameter of the circular shape may be varied by advancement or retraction of the loop 100 from the catheter 86. The loop 100 may be comprised of any suitable material such as metal, polymer, or fiber, and may have any suitable form such as wire, ribbon, links, or weave. FIG. 8C provides a side view of the embodiment shown in FIG. 8B. The circular shape of the loop 100 resides in a plane substantially perpendicular to the catheter 86. Thus, the loop 100 may be positioned along the annulus of the valve, as illustrated in FIG. 8A. In this position, the leaflets LF may still flail upwards. Referring to FIG. 8D, the diameter of the loop 100 may then be reduced, as indicated by arrows 102. This may be achieved by partial retraction of the loop 100 into the catheter 86. Continual reduction of the diameter draws the loop 100 from the annulus toward the center of the valve. As the loop 100 travels (prior loop 100' shown in dashed line), the loop 100 restricts upward motion or flailing of the leaflets LF in a controlled manner and positions the leaflets LF for optimal grasping between the proximal and distal elements 16, 18.

Figure 8E:
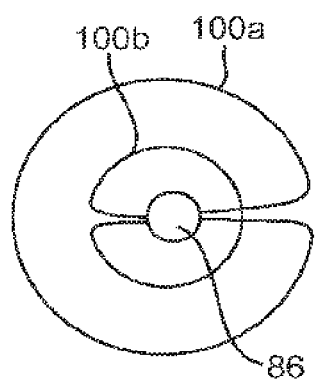
Figure 8F:
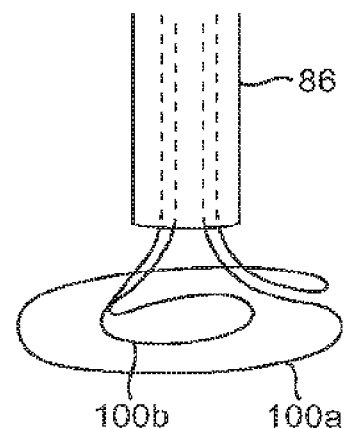

It may be appreciated that more than one loop 100 may be present to stabilize the leaflets; the loops may be concentric, adjacent to each other, in separate planes or in any suitable arrangement. For example, FIG. 8E illustrates an embodiment having a first loop 100a and a second loop 100b. The loops 100a, 100b function similarly to the embodiment illustrated in FIGS. 8A-8D, however, the second loop 100b is smaller and located concentrically within the first loop 100a. The diameters of the loops 100a, 100b may have any suitable size and the relationship of the diameters may vary. FIG. 8F provides a side view of the embodiment shown in FIG. 8E. As shown, the circular shapes of the loops 100a, 100b reside in a plane substantially perpendicular to the catheter 86. Thus, the loops 100a, 100b may be positioned against the valve leaflets LF to stabilize the leaflets LF. The diameter of the loops 100a, 100b may then be reduced, simultaneously or individually, by partial retraction of the loops 100a, 100b into the catheter 86. Continual reduction of the diameters draw the loops 100a, 100b toward the center of the valve. Again, as the loops 100a, 100b travel, the loops 100a, 100b restrict upward motion or flailing of the leaflets LF in a controlled manner and positions the leaflets LF for optimal grasping between the proximal and distal elements 16, 18.

Figure 8G:
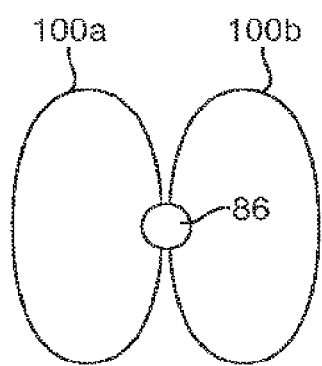
Figure 8H:
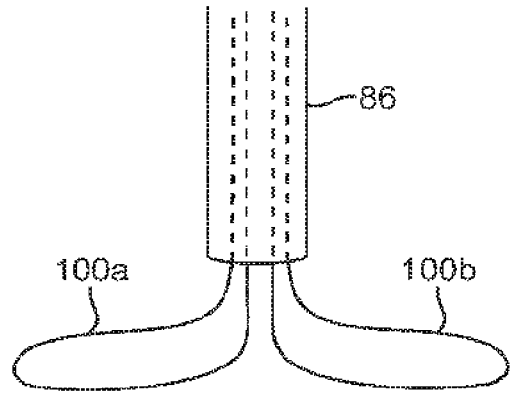
Figure 8I:
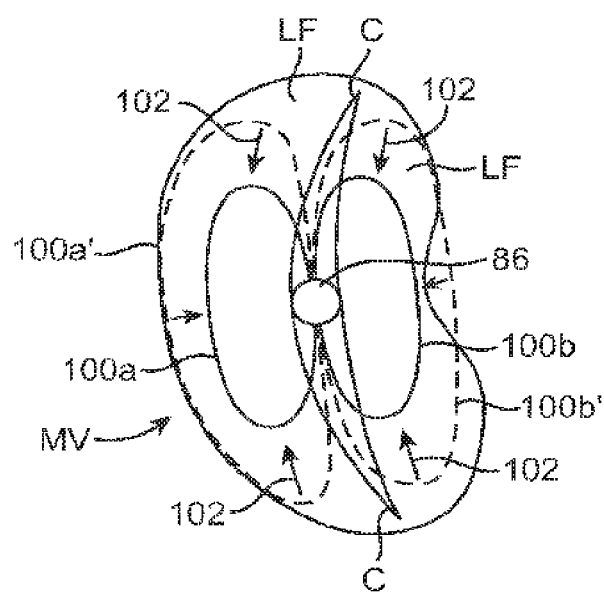

FIG. 8G illustrates another embodiment having a first loop 100a and a second loop 100b. However, in this embodiment, the loops 100a, 100b are non-concentric, each loop extending from an opposite side of the catheter 86. The diameters of the loops 100a, 100b may have any suitable size and the relationship of the diameters may vary. FIG. 8H provides a side view of the embodiment shown in FIG. 8G. As shown, the circular shapes of the loops 100a, 100b reside in a plane substantially perpendicular to the catheter 86. Thus, the loops 100a, 100b may be positioned against the valve leaflets LF to stabilize the leaflets LF. FIG. 8I provides a top view of the mitral valve MV wherein the catheter 86 is positioned above the valve MV so that the fixation device (not shown) may be passed through the leaflets LF. The loops 100a, 100b are shown extended radially outwardly toward the annulus. The diameter of the loops 100a, 100b may then be reduced, as indicated by arrows 102. This may be achieved by partial retraction of the loops 100a, 100b into the catheter 86. Continual reduction of the diameter draws the loops 100a, 100b from the annulus toward the center of the valve. As the loops 100a, 100b travel (prior loops 100a', 100*b*' shown in dashed line), the loops 100*a*, 100*b* restricts upward motion or flailing of the leaflets LF in a controlled manner and positions the leaflets LF for optimal grasping between the proximal and distal elements 16, 18. As shown, each loop 100*a*, 100*b* restricts movement of an individual leaflet LF. However, it may be appreciated that the catheter 86 may be oriented (such as at a 90 degree rotation) so that each loop 100*a*, 100*b* contacts more than one leaflet LF.

Figure 8J:
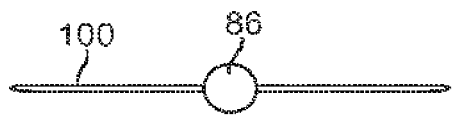
Figure 8K:
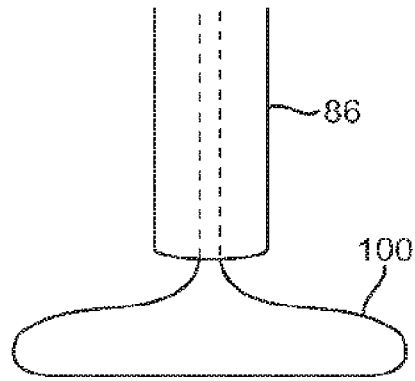
Figure 8L:
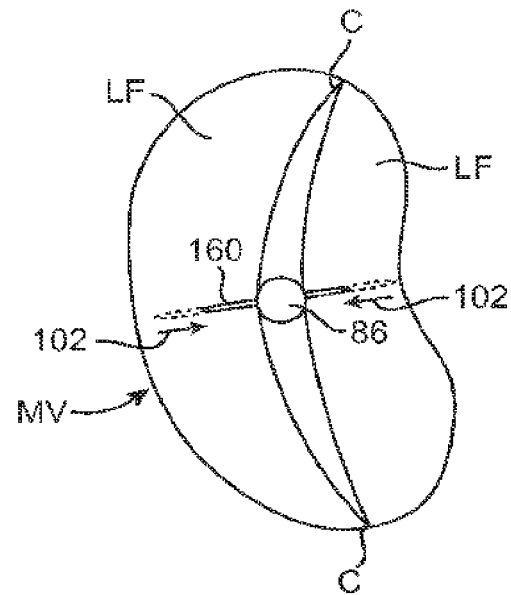

FIG. 8J illustrates an embodiment having a single loop 100 which resides in a plane substantially parallel to the catheter 86. FIG. 8K provides a side view of the embodiment shown in FIG. 8J. The loop 100 may have any suitable shape and diameter. Thus, the loop 100 may be positioned against the valve leaflets LF to stabilize the leaflets LF. FIG. 8L provides a top view of the mitral valve MV wherein the catheter 86 is positioned above the valve MV so that the fixation device (not shown) may be passed through the leaflets LF. The loop 100 is shown extended radially outwardly toward the annulus, perpendicular to the commissures C. Such positioning restricts upward movement of the leaflets LF. In addition, the diameter of the loop 100 may then be reduced, as indicated by arrows 102. This may be achieved by partial retraction of the loop 100 into the catheter 86. Continual reduction of the diameter draws the loop 100 from the annulus toward the center of the valve. As the loop 100 travels (prior loop 100' shown in dashed line), the loop 100 maintains restricted upward motion or flailing of the leaflets LF and positions the leaflets LF for optimal grasping between the proximal and distal elements 16, 18.

It may be appreciated that in any of the embodiments described above, the loops may be extended to stabilize both leaflets or may be extended to stabilize one leaflet that is flailing. This may be achieved by orientation of the catheter 86, shape of the loop 100, amount of extension of the loop 100 or any other method. The embodiments illustrated in FIGS. 8G-8I are particularly suited for single leaflet flailing wherein only the first loop 100*a* may be present. It may further be appreciated that the loops 100 may include surface treatments or accessories, such as rollers or grippers, to assist in stabilization of the leaflets.

Figure 9A:
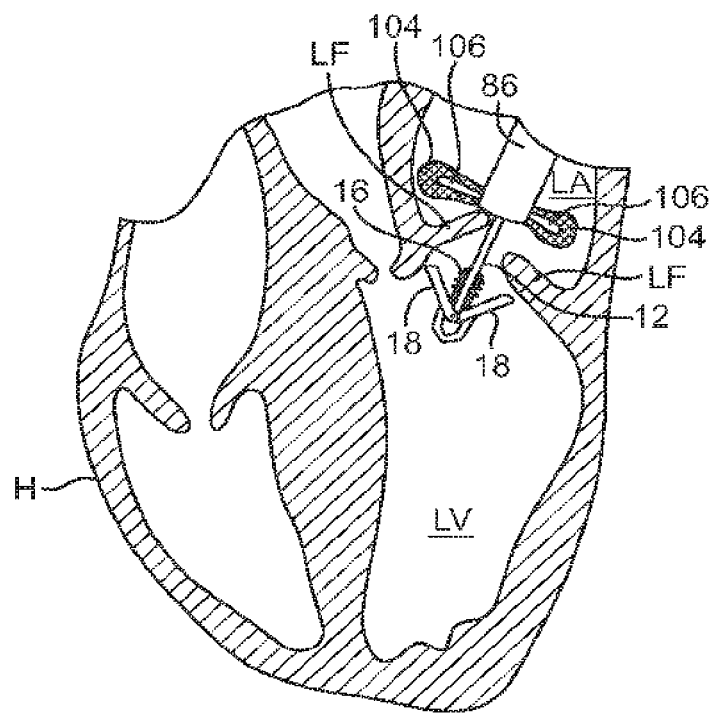
Figure 9B:
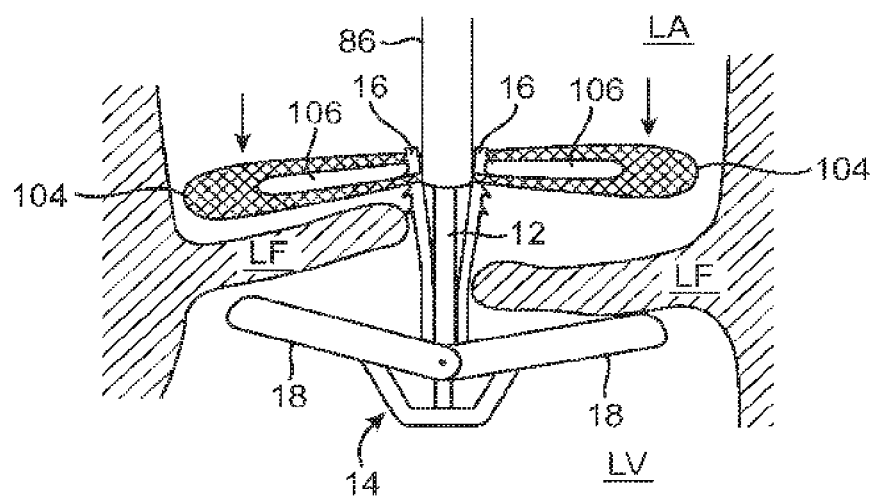

FIGS. 9A-9B illustrate another embodiment which stabilizes the valve leaflets LF by reducing upward mobility and flailing of the leaflets LF. As shown in FIG. 9A, a catheter 86 is advanced into a left atrium LA of a heart H and a fixation device 14 is advanced through the catheter 86 and through a mitral valve MV having leaflets LF so that at least a portion of the fixation device 14 is positioned within a left ventricle LV. The valve leaflets LF are shown flailing upwards toward the left atrium LA while the fixation device 14 resides below the valve, within the left ventricle LV. In this example, the fixation device 14 resembles the fixation device described above in relation to FIG. 3 and includes proximal elements 16 and distal elements 18. The fixation device 14 is at least partially opened to extend the distal elements 18 radially outwardly while the proximal elements 16 remain held against the shaft 12. It is desired to engage the leaflets LF with the distal elements 18 so that the proximal elements 16 may be lowered grasping the leaflets LF therebetween.

One or more flaps 104 may extend radially outwardly from the catheter 86, as shown, and be positioned against the atrial side of the leaflets LF. The flaps 104 may be comprised of any suitable material such as metal, polymer, or fiber, and may have any suitable form such as a solid, a mesh, or a weave. Further, the flaps 104 may have any suitable shape and may include one or more cutouts 106. As shown in FIG. 9B, the cutouts 106 may be sized and positioned to allow the proximal elements 16 of the fixation device 14 to extend therethrough. This allows the flaps 104 to be held against the atrial side of the leaflets LF restricting upward motion or flailing of the leaflets LF. This positions the leaflets LF for optimal grasping between the proximal and distal elements 16, 18. Once the leaflets have been grasped, the flaps 104 may be removed with the catheter 86 or may be left behind to assist in holding the leaflets LF.

Figure 10A:
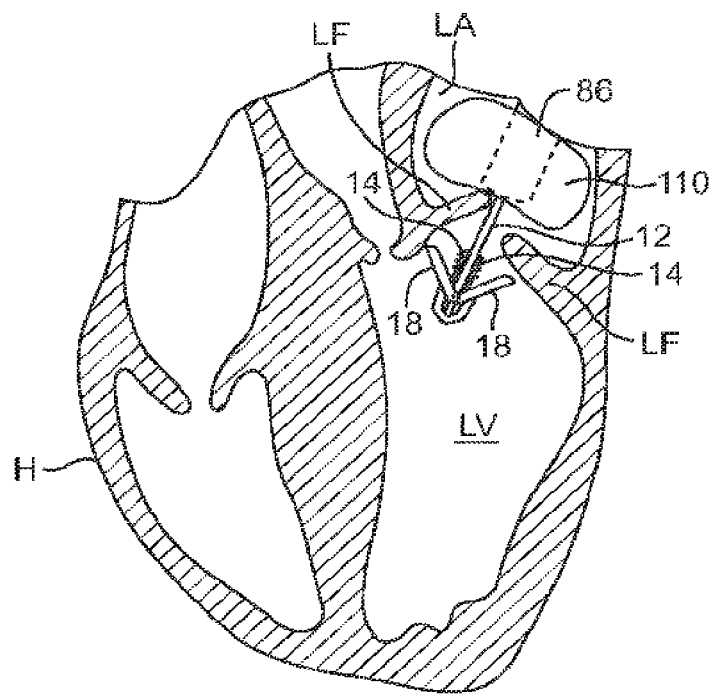
Figure 10B:
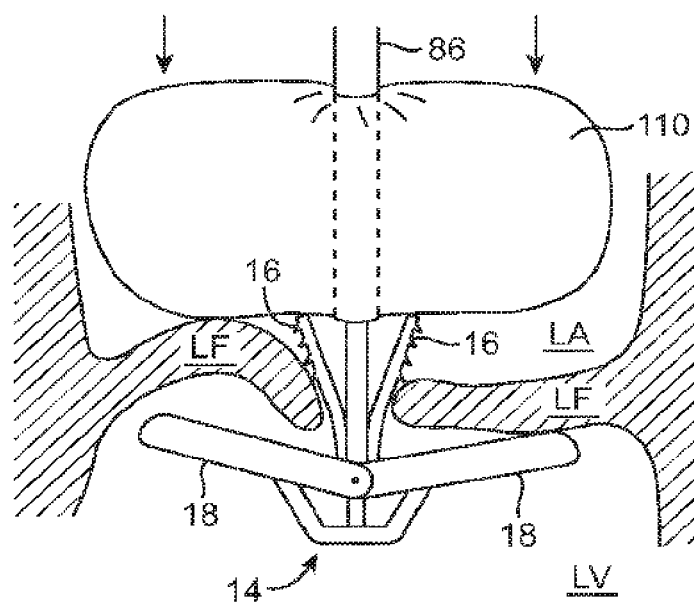

FIGS. 10A-10B illustrate another embodiment which stabilizes the valve leaflets LF by reducing upward mobility and flailing of the leaflets LF. As shown in FIG. 10A, a catheter 86 is advanced into a left atrium LA of a heart H and a fixation device 14 is advanced through the catheter 86 and through a mitral valve MV having leaflets LF so that at least a portion of the fixation device 14 is positioned within a left ventricle LV. The valve leaflets LF are shown flailing upwards toward the left atrium LA while the fixation device 14 resides below the valve, within the left ventricle LV. In this example, the fixation device 14 resembles the fixation device described above in relation to FIG. 3 and includes proximal elements 16 and distal elements 18. The fixation device 14 is at least partially opened to extend the distal elements 18 radially outwardly while the proximal elements 16 remain held against the shaft 12. It is desired to engage the leaflets LF with the distal elements 18 so that the proximal elements 16 may be lowered grasping the leaflets LF therebetween.

One or more expandable members 110 may extend radially outwardly from the catheter 86, as shown, and be positioned against the atrial side of the leaflets LF. The expandable member 110 may be comprised of any suitable material such as silicone or polyurethane and may have any suitable form such as a balloon. FIG. 10B provides an additional view of the embodiment. As shown, the expandable member 110 may be expanded within the left atrium and held against the atrial side of the leaflets LF restricting upward motion or flailing of the leaflets LF. This positions the leaflets LF for optimal grasping between the proximal and distal elements 16, 18.

Figure 11A:
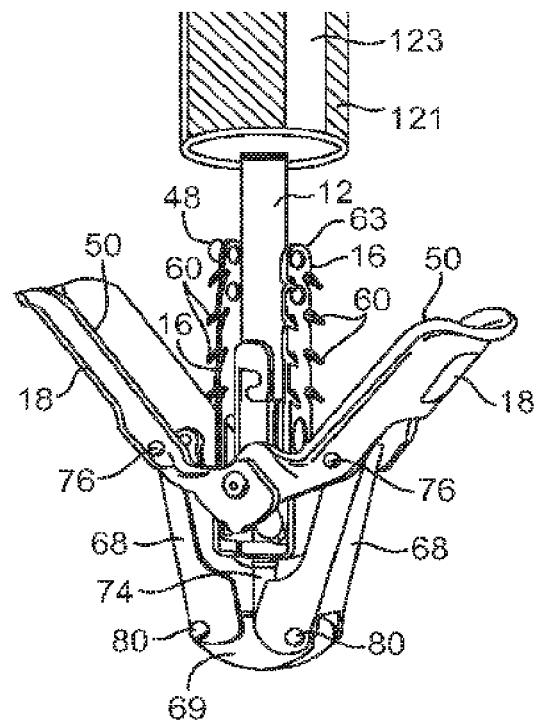
Figure 11B:
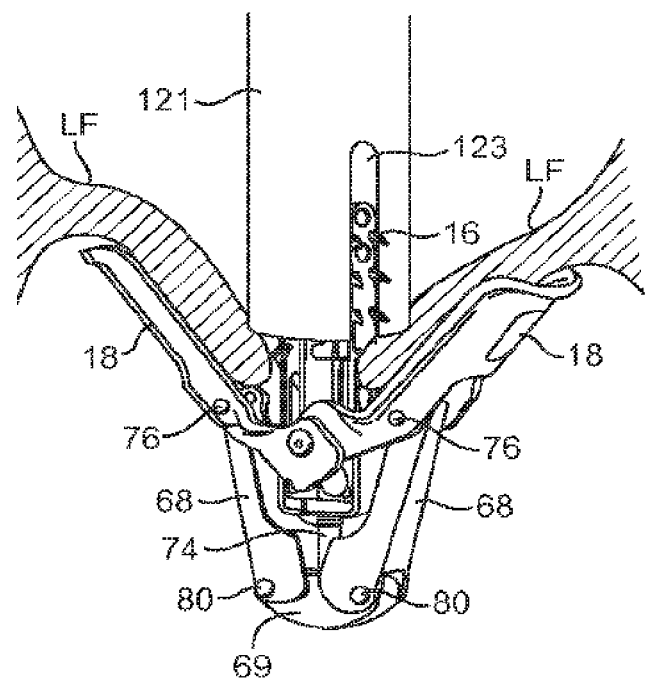

FIGS. 11A-11B illustrate another embodiment which stabilizes the valve leaflets LF by reducing upward mobility and flailing of the leaflets LF. In this example, the fixation device 14 resembles the fixation device described above in relation to FIG. 3 and includes proximal elements 16 and distal elements 18. Again, the fixation device 14 is advanced through a catheter and through a mitral valve MV having leaflets LF so that the distal elements 18 of the fixation device 14 are positioned within a left ventricle LV. The fixation device 14 is at least partially opened to extend the distal elements 18 radially outwardly while the proximal elements 16 remain held against the shaft 12. It is desired to engage the leaflets LF with the distal elements 18 so that the proximal elements 16 may then be lowered grasping the leaflets LF therebetween. However, prior to lowering the proximal elements 16, an overtube 121 having slots 123 is advanced over the shaft 12 and be positioned against the atrial side of the leaflets LF, as illustrated in FIG. 11B. The overtube 121 may be comprised of any suitable material such as polyimide, poly ethyl ethyl ketone (PEEK™), nylon resins (such as PEBAX®), or polyurethane and the slots may have any suitable dimension to allow passage of the proximal elements 16 therethrough. Holding of the leaflets LF by the overtube 121 restricts upward motion or flailing of the leaflets LF, and allows confirmation that leaflets are positioned correctly prior to lowering the proximal elements 16. This positions the leaflets LF for optimal grasping between the proximal and distal elements 16, 18. The proximal elements 16 may then be released, wherein the proximal elements 16 pass through the slots 123 hold the leaflets between the proximal and distal elements 16, 18. The overtube 121 may then be retracted and removed.

Figure 12A:
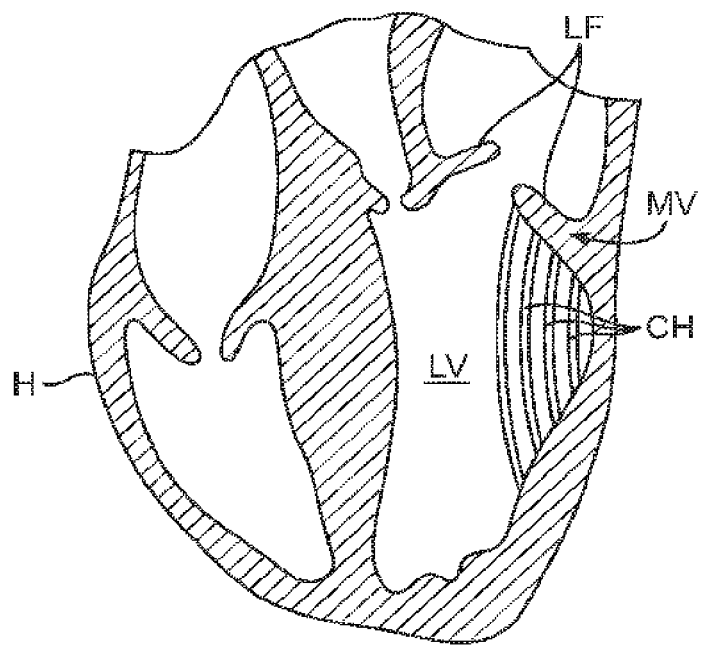
FIGS. 12A-12B illustrate an embodiments which stabilizes the valve leaflets by applying tension to the chordae attached to the leaflets.
Figure 12B:
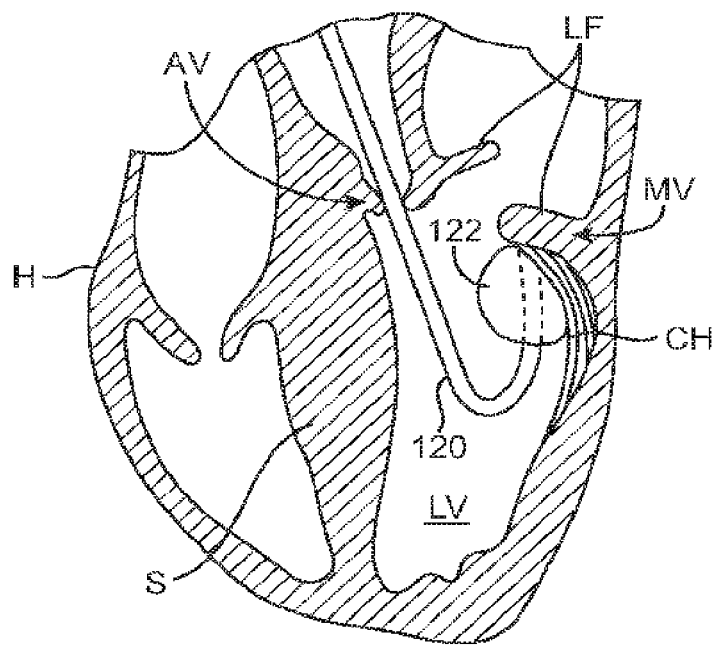

FIGS. 12A-12B illustrate embodiment which stabilizes the valve leaflets by applying tension to the chordae attached to the leaflets. Such stabilization may be desired to reducing upward mobility and flailing of the leaflets or to simply reduce movement of the leaflets. FIG. 12A illustrates a heart H having a mitral valve MV comprised of leaflets LF. Chordae CH are shown extending from one of the leaflets LF to the left ventricle LV. It may be appreciated that chordae are numerous and extend from both leaflets to the left ventricle however select chordae are illustrated for simplicity. As shown in FIG. 12B, a catheter 120 having an expandable member 122, such as a balloon, may be advanced to the left ventricle LV wherein the catheter 120 is positioned and the expandable member 122 expanded so that tension is applied to the chordae CH. FIG. 12B shows the catheter 120 advanced through the aortic valve AV however the catheter 120 may approach the chordae CH via any suitable pathway, including through the mitral valve MV or through the septum S. Applying tension to the chordae CH adjusts the position of the attached leaflet LF. Thus, the leaflet LF may be manipulated and repositioned by manipulating the catheter 120 and expandable member 122, including varying expansion of the expandable member 122. In particular, by pressing laterally against the chordae CH with the expandable member 122 the leaflet LF may be drawn downward restricting upward mobility and flailing of the leaflet LF. Once the leaflets LF are disposed in a desirable position, the leaflets LF may be fixed by a fixation device such as described in relation to FIG. 3. Alternatively, a grasper may be employed to tension the chordae CH.

Figure 13:
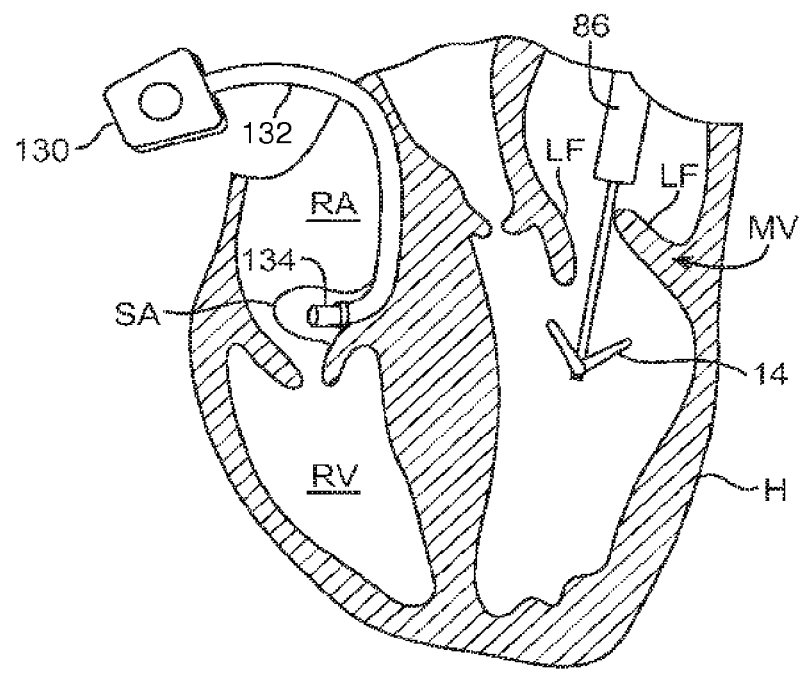
FIG. 13 illustrates a pacing lead extending to the sinoatrial node which regulates movement of leaflets to assist in grasping of the leaflets.
Figure 14:
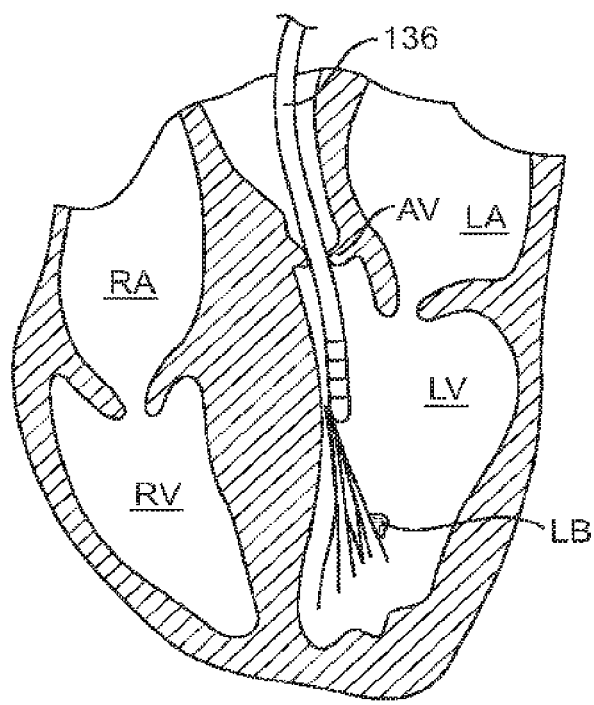
FIG. 14 illustrates pacing of the left ventricle directly with a pacing catheter.

The above described embodiments focus on mechanically stabilizing the valve leaflets. Additional embodiments focus on stabilizing the valve leaflets by physiologically slowing the motion of the leaflets. This may be achieved by slowing the natural pace of the heart. In one embodiment, illustrated in FIG. 13, a pacemaker 130, or pulse generator, is shown having a pacing lead 132 with an electrode 134 which extend to the sinoatrial node SA in the right atrium RA. Pacing is achieved when the pacemaker 130 sends electrical impulses through the pacing lead 132 to the electrode 134 which stimulates the sinoatrial node SA. This stimulates the right atrium RA to pump blood into the right ventricle RV and thereon through the heart H. Thus, the pumping of the heart and therefore movement of the leaflets of the valves can be regulated with the use of the pacemaker 130. FIG. 13 illustrates a fixation device 14 passed through the leaflets LF of the mitral valve MV. The movement of the leaflets LF may be paced so that, for example, the mitral valve MV stays in systole (closed) for a longer period of time to aid in grasping the leaflets LF with the fixation device 14. Similarly, as illustrated in FIG. 14, the left ventricle LV may be paced directly with a pacing catheter 136 by stimulating left bundle LB. This may be achieved by advancing the pacing catheter 136 through the aortic valve AV to the left ventricle LV as shown.

III. Grasping Assistance

To assist in effectively and efficiently grasping the leaflets, a variety of devices and techniques are provided. Many of the devices and techniques will be described as adjuncts to the fixation device described in relation to FIG. 3. However, many features may be used with any suitable grasping and/or fixing device. Further, many of such techniques and devices may be used to grasp valve leaflets, or other tissues, for any purpose.

In some situations, one or more leaflets LF are not grasped between the proximal elements 16 and distal elements 18 in a desired position. For example, a less than desired amount of the leaflet LF may be grasped. Such decreased purchase may, for example, reduce the effectivity of the regurgitation treatment and/or increase the risk of the leaflet LF slipping out of the fixation device. Once a portion of the leaflet LF is grasped, the leaflet LF position may be adjusted; for example, the leaflet LF may be "pulled in" or advanced toward the shaft 12 of the fixation device 14 to increase the purchase. Embodiments to assist in such adjustment are provided in FIGS. 15-17, 18A-18B.

Figure 15:
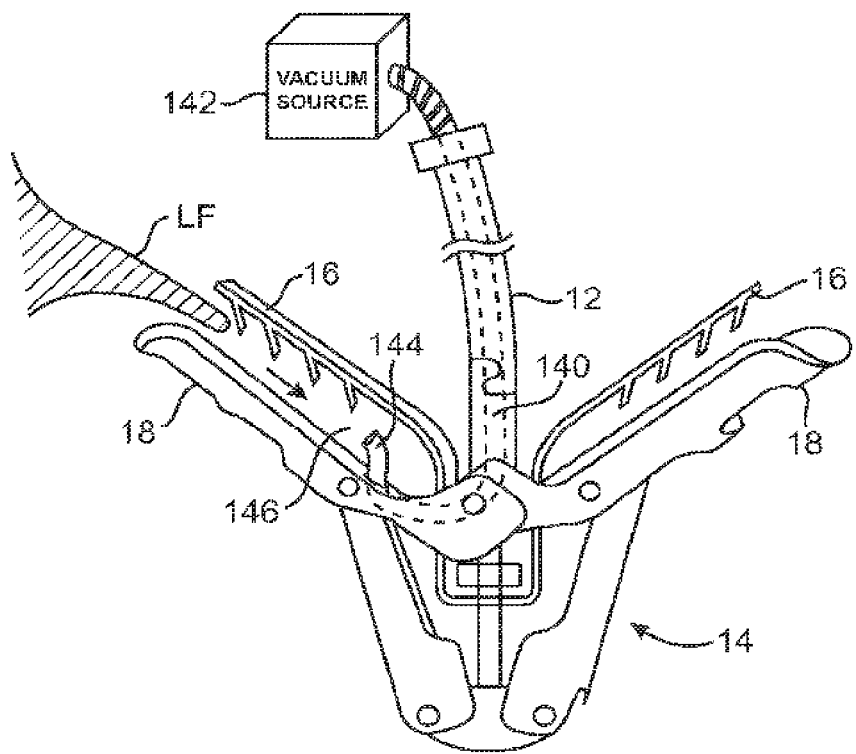
FIG. 15 illustrates an embodiment of a fixation device having a vacuum line.

FIG. 15 illustrates an embodiment of a fixation device 14 similar to the fixation device 14 illustrated in FIG. 3. As shown, a leaflet LF is partially grasped between a proximal element 16 and a distal element 18. In this embodiment, a vacuum line 140 extends through the shaft 12 and is connected to a vacuum source 142. The vacuum line 140 has a distal end 144 which protrudes into a space 146 between the proximal and distal element 16, 18. Actuation of the vacuum source 142 applies suction to the space 146 which draws the leaflet LF inward toward the shaft 12. Thus, the leaflet LF, once grasped, may be repositioned within the proximal and distal elements by suction force. It may be appreciated that the same vacuum line 140 or an additional vacuum line may apply suction to a leaflet between the other proximal and distal elements. Further, it may be appreciated that suction force may be applied during the initial grasp to assist in the act of grasping.

Figure 16:
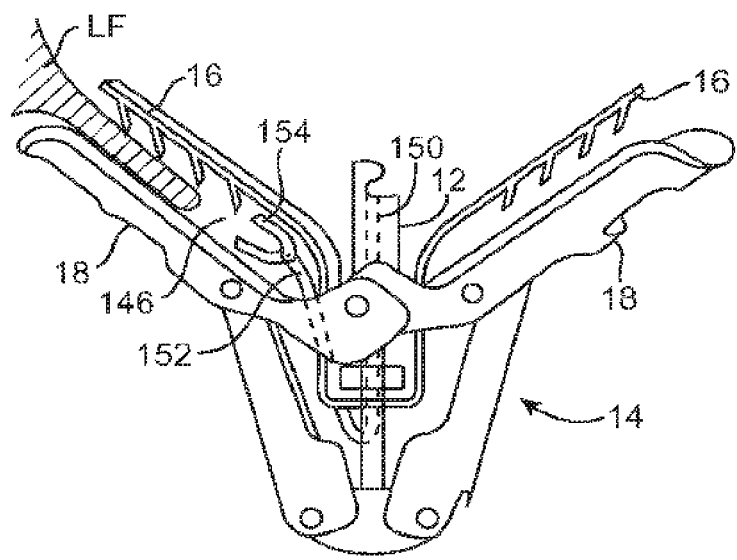
FIG. 16, illustrates an embodiment of a fixation device having an adjunct-grasper.

Similarly, as illustrated in FIG. 16, another embodiment of a fixation device 14 is shown similar to the fixation device 14 illustrated in FIG. 3. Again, a leaflet LF is partially grasped between a proximal element 16 and a distal element 18. In this embodiment, an adjunct-grasper channel 150 extends through the shaft 12 for passage of an adjunct-grasper 152 having jaws 154, however any type of grasping mechanism may be present such as atraumatic hooks, clamps or claws. The jaws 154 protrude into a space 146 between the proximal and distal element 16, 18. The adjunct-grasper 152 may be advanced to grasp the leaflet LF with the jaws 154 and retracted to pull the leaflet LF inward toward the shaft 12. Thus, the leaflet LF may be repositioned by manipulation of the adjunct-grasper 152. It may be appreciated that the same or an additional adjunct-grasper 152 may be used to reposition a leaflet between the other proximal and distal elements. Further, it may be appreciated that the adjunct-grasper 152 may be used during the initial grasp to assist in the act of grasping.

Figure 17:
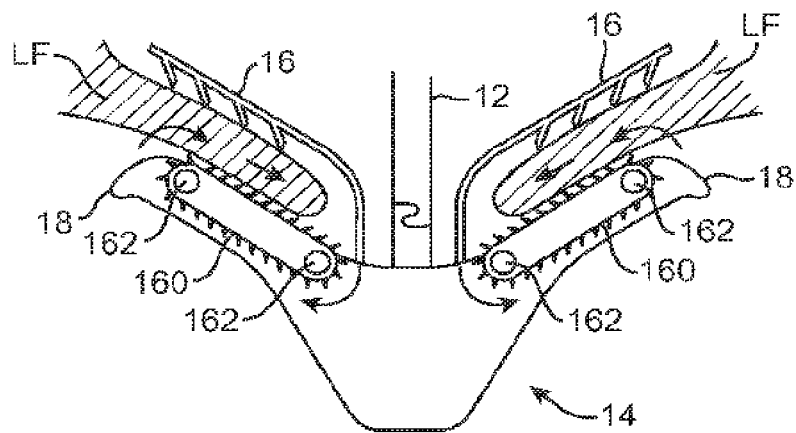
FIG. 17 illustrates an embodiment of a fixation device having a conveyor belt.

FIG. 17 illustrates another embodiment of a fixation device 14 similar to the fixation device 14 illustrated in FIG. 3. Again, a leaflet LF is partially grasped between a proximal element 16 and a distal element 18. In this embodiment, a conveyor belt 160 is disposed within each distal element 18 so that a surface of the belt 160 contacts the grasped leaflet LF. The conveyor belt 160 is mounted on one or more rollers 162. Rotation of the rollers 162 moves the conveyor belt 160 which in turn moves the contacted leaflet LF. For example, clockwise rotation of the rollers 162 may pull or drag the leaflet LF inwardly toward the shaft 12, as shown. Similarly, counterclockwise rotation of the rollers 162 may pull or drag the leaflet LF outwardly. Thus, the leaflet LF may be repositioned by movement of the conveyor belt 160. It may be appreciated that conveyor belts 160 disposed within the distal elements 18 may function independently or in unison.

Further, it may be appreciated that the conveyor belts 160 may be used during the initial grasp to assist in the act of grasping.

Figure 18A:
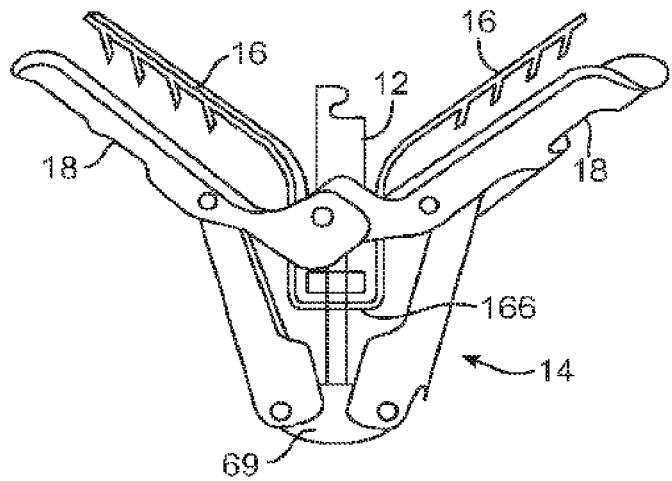
FIGS. 18A-18B illustrates an embodiment of a fixation device having proximal elements which are adjustable inwardly to draw grasped tissue further into the fixation device.
Figure 18B:
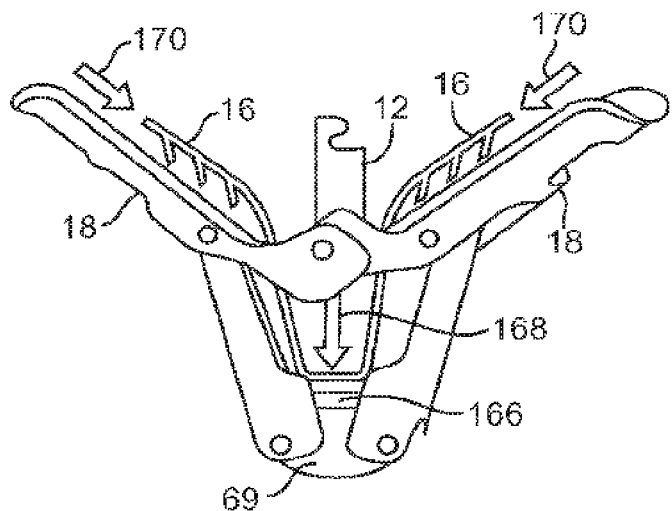

FIGS. 18A-18B illustrate another embodiment of a fixation device 14 similar to the fixation device 14 illustrated in FIG. 3 having proximal elements 16 and distal elements 18. In this embodiment, the proximal elements 16 are connected by a bridge 166 which straddles the shaft 12. Referring to FIG. 18B, once a leaflet is grasped between the proximal and distal elements 16, 18, a force may be applied to move the bridge 166 toward the base 69 of the fixation device 14, as indicated by arrow 168. Due to the curvature of the proximal elements 16, such movement of the bridge 166 draws the proximal elements 16 inwardly toward the shaft 12 (as indicated by arrows 170) which it turn draws the grasped leaflet inwardly toward the shaft 12. Similarly, force applied to move the bridge 166 away from the base 69 moves the proximal elements 16 outwardly. Thus, the leaflets may be repositioned by movement of the bridge 166. It may be appreciated that the bridge 166 may move toward the base 69 due to movement of the distal elements 18 toward the closed position. Or, the proximal elements 16 may be attached to a cam, or other suitable element, so as the distal elements 18 close, the proximal elements 14 are drawn inwardly toward the shaft 12. Thus, the proximal elements 16 may move while the distal elements 18 are static, or both the proximal elements 16 and the distal elements 18 may move relative to each other. It may further be appreciated that in some embodiments, the distal elements 18 may move while the proximal elements 16 are static.

FIGS. 19A-19C illustrate an embodiment of a fixation device 14 similar to the fixation device 14 illustrated in FIG. 3 with the inclusion of a passageway through the shaft 12 for passage of a pre-grasper 176 as shown. The pre-grasper 176 has a shaft 178 and jaws 180 disposed near its distal end 182, however any type of grasping mechanism may be present such as atraumatic hooks, clamps or claws. Referring to FIG. 19B, the fixation device 14 is advanced through the mitral valve in an atrial approach as described above so that the fixation device 14 resides within the ventricle. The pre-grasper 176 is advanced through the shaft 12 and manipulated to grasp a portion of one or both of the leaflets LF. The pre-grasper 176 may be steered by any suitable mechanisms, including pullwires, or the pre-grasper 176 may be pre-formed in a desired configuration. Further, the pre-grasper 176 may be rotated within the shaft 12. The pre-grasper 176 may grasp one leaflet or the pre-grasper 176 may grasp both leaflets, such as in a coapted orientation, to stabilize the leaflet(s) and/or move the leaflet(s) to a desired orientation. Once the leaflets are satisfactorily oriented, the fixation device 14 may be used to grasp the leaflets LF as illustrated in FIG. 19C. The pre-grasper 176 may then be released from the leaflets LF and removed by withdrawal through the passageway in the shaft 12. Alternatively, the pre-grasper 176 can be left in place to reinforce the fixation of the leaflets.

Figure 20:
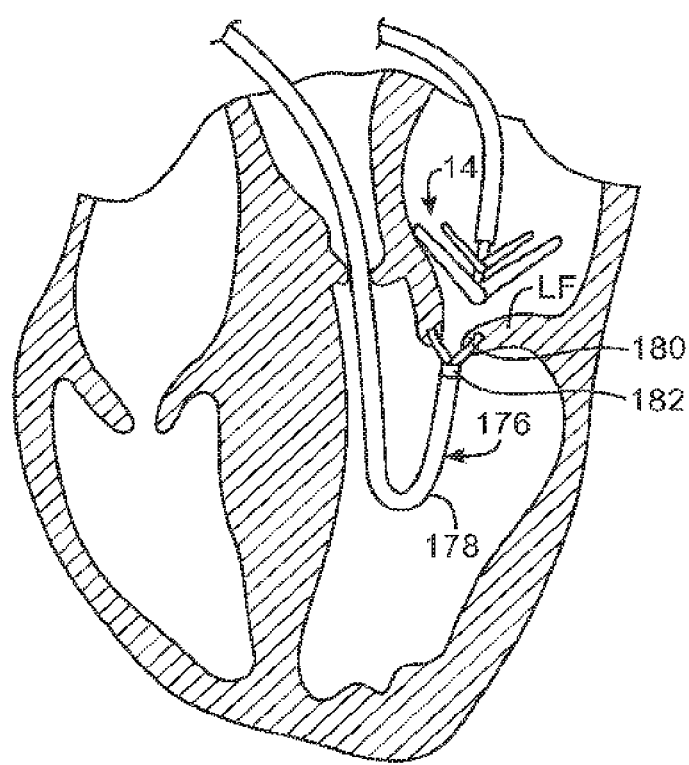
FIG. 20 illustrates a fixation device advanced via an atrial approach and a pre-grasper advanced via a ventricular approach.

In other embodiments the pre-grasper 176 is separately advanced to the tissue to leaflets LF, such as by a different approach. FIG. 20 illustrates the fixation device 14 advanced via an atrial approach and the pre-grasper 176 advanced via a ventricular approach. Again, the pre-grasper 176 has a shaft 178 and jaws 180 disposed near its distal end 182, however any type of grasping mechanism may be present such as atraumatic hooks, clamps or claws. The pre-grasper 176 is advanced and manipulated to grasp a portion of one or both of the leaflets LF. The pre-grasper 176 may be steered by any suitable mechanisms, including pullwires, or the pre-grasper 176 may be pre-formed in a desired configuration. Further, the pre-grasper 176 may be rotated. The pre-grasper 176 may grasp one leaflet or the pre-grasper 176 may grasp both leaflets, such as in a coapted orientation, to stabilize the leaflet(s) and/or move the leaflet(s) to a desired orientation. Once the leaflets are satisfactorily oriented, the fixation device 14 may be used to grasp the leaflet. LF the fixation device 14 is advanced through the mitral valve in an atrial approach as described above so that the fixation device 14 resides within the ventricle. This is typically achieved by passing at least a portion of the fixation device 14 through the leaflets LF adjacent to the area of the leaflets grasped by the pre-grasper 176. The pre-grasper 176 may then be released from the leaflets LF and removed by withdrawal. Alternatively, the pre-grasper 176 can be left in place to reinforce the fixation of the leaflets. It may be appreciated that in other embodiments, the fixation device 14 is advanced via a ventricular approach and the pre-grasper 176 advanced via an atrial approach.

Figure 21A:
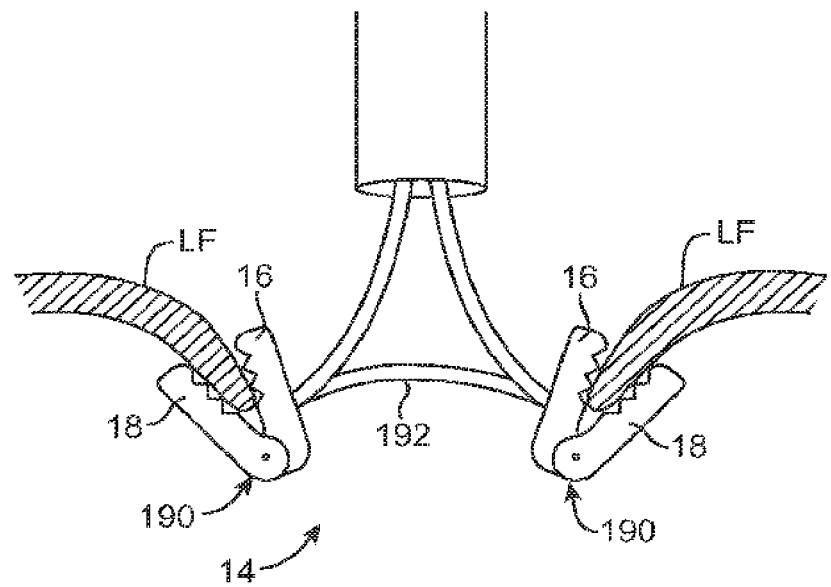
FIGS. 21A-21B illustrate embodiments of a fixation device having two single-sided fixation elements joinable by a tether.
Figure 21B:
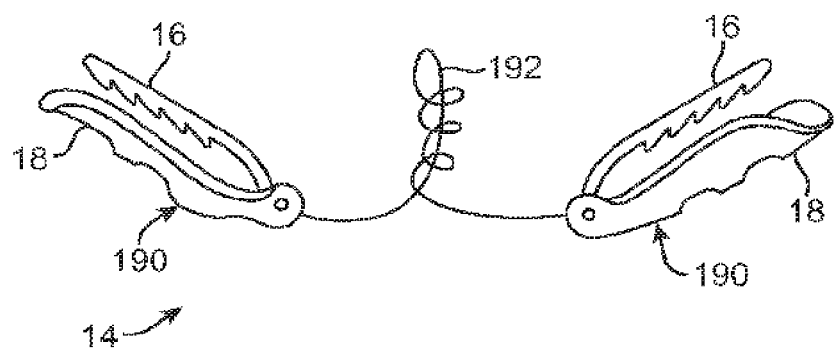

FIGS. 21A-21B illustrate embodiments of a fixation device 14 having two single-sided fixation elements 190 joinable by a tether 192. Each single-sided fixation element 190 is comprised of at least a proximal element 16 and a distal element 18. In some embodiments, the single-sided fixation element 190 resembles one half of the fixation device 14 illustrated in FIG. 3. FIG. 21A illustrates a pair of single-sided fixation elements 190, each fixation element 190 grasping a leaflet LF between its proximal element 16 and distal element 18. The fixation elements 190 may be delivered to the leaflets LF through a delivery catheter 191, each element 190 connected to an elongate delivery apparatus 193 which passes through the catheter 191. The fixation elements 190 are also connected to each other by the tether 192. Once, the fixation elements 190 have satisfactorily grasped the leaflets LF the fixation elements 190 may be detached from the delivery apparatuses 193 and left behind to hold the leaflets LF in a desired orientation via the tether 192. Alternatively, the tether 192 may be shortened or tensioned to draw the fixation elements 190 together, thereby coapting the leaflets LF. In some embodiments, such as illustrated in FIG. 21B, the tether 192 comprises a resilient element, such as a coil or spring, that "self-shortens" upon release from the catheter 191. Other means of shortening or tensioning the tether 192 may include applying a suture fastener to the tether 192, preferred embodiments of which are described and illustrated in U.S. patent application Ser. No. 10/087,004. In other embodiments, each one-sided fixation element 190 is attached to an individual tether which extends through the catheter 191. The individual tethers may then be knotted together, the knot being pushed toward the fixation elements 190 so as to tie them together at a desired distance.

Thus, the fixation elements 190 may be linked, attached, coupled or joined together to hold the leaflets LF in the coapted position. It may be appreciated that any number of single-sided fixation elements 190 may be used, some or all of which may be joinable by one or more tethers 192. Further, it may be appreciated that at least one of the single-sided fixation elements 190 may be used to grasp tissues other than valve leaflets, such as chordae, to assist in treatment of the valve. For example, the elements 190 may join leaflet to leaflet, leaflet to papillary muscle, leaflet to chordae, etc. Still further, it may be appreciated that each of the single-sided fixation elements 190 may be deployed from opposite sides of the valve, such as from an atrial approach and a ventricular approach, and joined across the valve. Thus, one single-sided fixation element 190 may be deployed on an anterior side of the valve and one on a posterior side of the valve, the elements 190 then cinched together to correct regurgitation.

Figure 22:
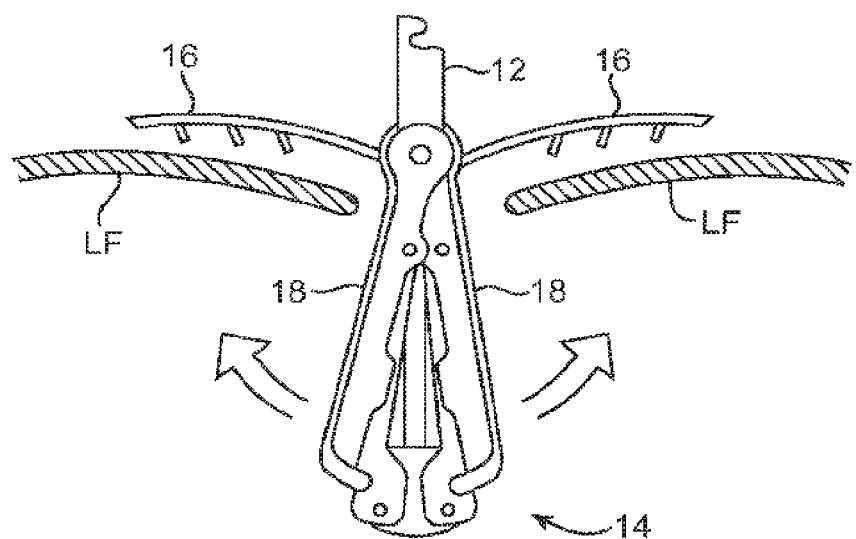
FIG. 22 illustrates an embodiment of fixation device having self-engaging distal elements.

FIG. 22 illustrates an embodiment of a fixation device 14 similar to the fixation device 14 illustrated in FIG. 3, including proximal elements 16 and distal elements 18. However, in this embodiment, the distal elements 18 are "self-engaging". The fixation device 14 may be positioned within the mitral valve so that the distal elements 18 are disposed within the ventricle and the proximal elements 16 are disposed within the atrium, as illustrated in FIG. 22. Rather than engaging the leaflets LF with the distal elements 18 and then lowering the proximal elements 16 to grasp the leaflets LF therebetween, the proximal elements 16 are first lowered to engage the leaflets LF. Lowering of the proximal elements 16 may stabilize the leaflets LF and reduce possible upward motion or flailing of the leaflets LF. The distal elements 18 may then self-engage or automatically move toward a closed position to engage the leaflets LF and grasp the leaflets LF between the proximal and distal elements 16, 18. Self-engagement may be actuated by a variety of mechanisms, including a mechanism that signifies lowering of the proximal elements 16 to a predetermined position or a sensor that senses sufficient engagement of the proximal elements 16 with the leaflets LF. It may be appreciated that the method of lowering the proximal elements 16 prior to engagement of the distal elements 18 may be utilized with the fixation device 14 of FIG. 3 without automatic engagement of the distal elements 18.

Once the leaflets have been grasped, a variety of features may assist in holding the grasped leaflets within the fixation device. For example, FIG. 23 illustrates an embodiment of a fixation device 14 having suction to maintain leaflet position after grasping, particularly during movement of the distal elements 18 toward a closed position. In this embodiment, suction lines 200 extend to suction ports 202 disposed on the engagement surfaces 50 of the distal elements 18. The suction lines 200 extend through the fixation device to a vacuum source similarly to the embodiment illustrated in FIG. 15. Once the distal elements 18 engage the leaflets with the engagement surfaces 50, suction applied through the suction ports 202, assists to hold the leaflets against the engagement surfaces 50. Such suction may be applied prior to, during and/or after lowering of any proximal elements 14 to hold the leaflets therebetween. As mentioned, such suction may be particularly helpful in securing the leaflets within the fixation device 14 during movement of the distal elements 18 toward a closed position.

In another example, FIGS. 24A-24B illustrate an embodiment of a fixation device 14 having extended frictional accessories. As described previously, the proximal elements 16 optionally include frictional accessories, frictional features or grip-enhancing elements to assist in grasping and/or holding the leaflets. And, as described and illustrated in FIG. 5B, the frictional accessories may comprise barbs 60 having tapering pointed tips extending toward engagement surfaces 50. FIG. 24A illustrates proximal elements 16 having extended barbs 206 which are directed toward engagement surfaces 50 of the distal elements 18. Likewise, FIG. 24B provides a closer view of the barbs 206 on the proximal elements 16 of FIG. 24A. As shown, the length L is extended. Such extended barbs 206 may be comprised of any suitable material, including rubber, flexible or rigid polymers or various metals. In preferred embodiments, the extended barbs 206 are atraumatic, the additional length L providing increased surface area to hold the leaflets with frictional forces.

FIGS. 25A-25B illustrate an embodiment of a fixation device 14 having a textured gripping surface 212 to assist in holding the grasped leaflets within the fixation device 14. An embodiment of the textured gripping surface 212 is illustrated in FIG. 25A. The surface 212 includes a plurality of protrusions 214 which extend outwardly at an angle. The protrusions may be comprised of any suitable material, preferably flexible material such as silicones, polymers, or fibers. The protrusions 214 are angled in a substantially uniform direction to provide friction against an object moving in the opposite direction. The textured gripping surface 212 may be applied to any suitable portion of the fixation element 14, such as the proximal elements 14 or the engagement surfaces 50 of the distal elements 18. FIG. 25B illustrates a fixation element 14 having the textured gripping surface 212 on a covering 210 over the distal elements 18. The covering 210 may be present to promote tissue growth. In this embodiment, the covering comprises a biocompatible fabric cover positioned over the distal elements 18. The covering 210 may optionally be impregnated or coated with various therapeutic agents, including tissue growth promoters, antibiotics, anti-clotting, blood thinning, and other agents. Alternatively or in addition, the covering 210 may be comprised of a bioerodable, biodegradable or bioabsorbable material so that it may degrade or be absorbed by the body after the repaired tissues have grown together. It may be appreciated that such a covering 210 may cover the distal elements 18 and/or proximal elements 16 of any of the fixation devices 14 described herein. The textured gripping surface 212 is shown disposed on the covering 210 which covers the engagement surfaces 50. The protrusions 214 are angled toward the shaft 12 of the fixation device 14. Therefore, leaflet LF may be drawn toward the shaft 12 in the same direction as the protrusions 214 encountering minimal friction. However, leaflet LF' moving away from the shaft 12 encounters significant friction from the protrusions 214 as the protrusions 214 are engaged and resist movement of the leaflet LF'. Thus, the textured gripping surface 212 resists movement of the leaflets away from the shaft 12, assisting in holding the grasped leaflets within the fixation device 14.

FIGS. 26A-26B illustrate another embodiment of a fixation device 14 having a textured gripping surface 212 to assist in holding the grasped leaflets within the fixation device 14. In this embodiment, the surface 212 includes a plurality of protrusions 214 which extend outwardly at an angle. The protrusions may be comprised of any suitable material, preferably a rigid material capable of piercing into and/or through the leaflet. Therefore, the protrusions may also be pointed or sharpened. The textured gripping surface 212 may be applied to any suitable portion of the fixation element 14, preferably the engagement surfaces 50 of the distal elements 18. FIG. 26A shows leaflets LF grasped by the distal elements 18, the protrusions 214 extending through the leaflets LF which assist in holding the leaflets LF in place. The proximal elements 16 may then be released, grasping the leaflets LF between the proximal and distal elements 16, 18. In some embodiments, the proximal elements 16 apply force to the protrusions 214, bending the protrusions 214 toward the engagement surfaces 50 so that the protrusions 214 "staple" the leaflets LF to the engagement surfaces 50, as illustrated in FIG. 26B. Alternatively, the protrusions 214 may have barbed or arrowhead shaped tips which may similarly act to staple the leaflets LF to the engagement surfaces 50.

IV. Grasping Assessment

Once the tissue or leaflets have been grasped, it is often desired to evaluate or assess the quality of the grasp, such as the amount of purchase, orientation of the tissues, and likelihood that the fixation device will maintain the grasp over time. Thus, a variety of devices and techniques are provided to assess the grasp. It may be appreciated that the assessment devices and techniques may be used in combination with the above described fixation devices or may be used with any suitable grasping and/or fixing device. Further, many of such assessment devices and techniques may be used to assess grasping of valve leaflets, or other tissues, for any purpose.

Figure 27A:
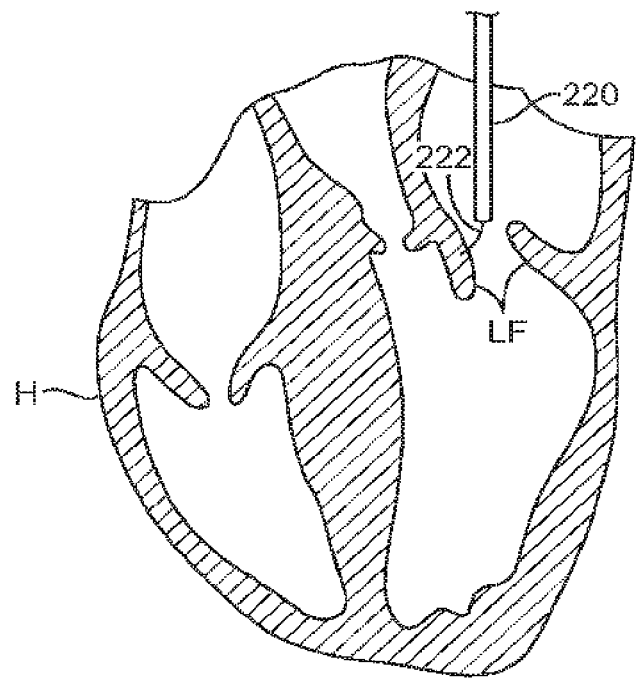
FIGS. 27A-27B illustrate injecting leaflets with a substance which enhances visibility.
Figure 27B:
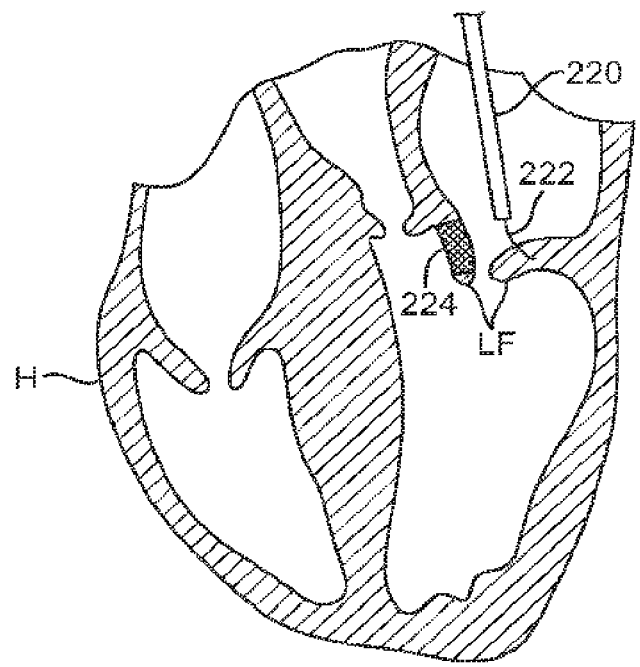

One method of determining quality of grasp is to visualize the grasp by means of fluoroscopy, ultrasound, echocardiography or other known visualization techniques. Using these techniques, a physician or practitioner may be able to observe an image of the fixation device and the grasped tissue to determine if the grasp is desirable. The fixation device may be visually differentiated from the surrounding tissue by enhancing the visibility of portions of the surrounding tissue, particularly the tissue intended to be grasped, such as the valve leaflets. Thus, as illustrated in FIGS. 27A-27B, the leaflets LF may be injected with a substance which enhances visibility prior to and/or after grasping with the fixation device. Example substances include liquid contrast material or bioabsorbable polymer beads having air bubbles trapped within. As shown in FIG. 27A, an injection catheter 220 having a needle 222 may be advanced to the leaflet LF to inject the substance. Exemplary injection catheters are described in U.S. Pat. Nos. 6,685,648; 4,578,061; 6,540,725; 6,165,164. FIG. 27B illustrates a leaflet LF having the substance 224 injected therein (as indicated by shading) and another leaflet being injected by the needle 222 of the injection catheter 220.

Figure 28:
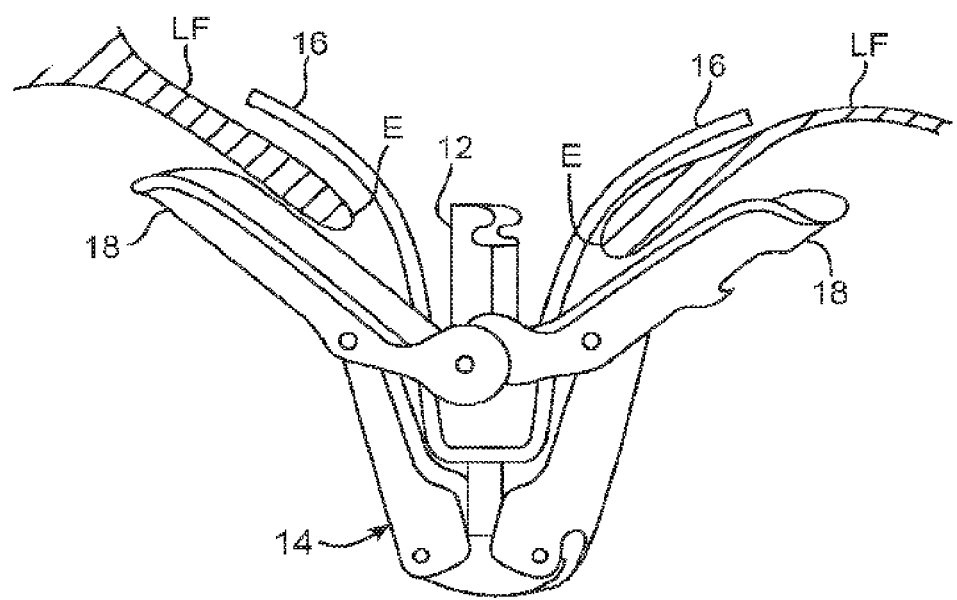
FIG. 28 illustrates a fixation device wherein the proximal elements and distal elements have enhanced visibility.

Alternatively, portions of the fixation device may have enhanced visibility to differentiate the fixation device from the surrounding tissue. For example, FIG. 28 illustrates a fixation device 14 wherein the proximal elements 16 and distal elements 18 have enhanced visibility, as indicated by shading. Such enhanced visibility may assist differentiation of the proximal and distal elements 16, 18 from valve leaflets LF captured therebetween. Further, the practitioner may be able to determine where the leaflet edges E are located with respect to the proximal and distal elements 16, 18, e.g. how closely the edges E are to the shaft 12 of the fixation element 14. This may indicate the size of the purchase. In some embodiments, surfaces of the fixation device are roughened, such as by bead blasting, to enhance visibility such as echogenicity. In other embodiments, at least portions of the fixation device 14 have an enhanced visibility covering. Such a covering may be comprised of cloth having titanium threads, spun polyester or other material which provides echogenicity. Alternatively or in addition, the covering may be stamped or impregnated with materials which provide echogenicity, such as barium sulfate. Or, the visibility of the covering may be enhanced by a bulky appearance of the covering.

In some embodiments, the fixation device includes an ultrasound receiving indicator. The ultrasound receiving indicator is typically disposed along a proximal or distal element near a target area. The indicator is used to determine the presence or absence of tissue within the target area thereby assessing the quality of the grasp. The indicator comprises a chip or other device that resonates or vibrates at a specific ultrasonic frequency which differs from the general frequency used to visualize the remainder of the fixation device and the surrounding tissue. Therefore, when the specific ultrasonic frequency is used for visualization, the indicator provides a bright visual artifact on an echocardiogram image. This indicates that the tissue is not sufficiently grasped within the target area because the indicator is freely vibrating. However, if the tissue is compressed between the proximal and distal elements within the target area, the tissue compresses the indicator, reducing or damping the vibration of the indicator. Thus, if the bright visual artifact is not seen at the specific ultrasonic frequency, it may be determined that the tissue is sufficiently grasped within the target area of the fixation device. This allows the practitioner to actively evaluate the grasp by viewing a dynamic change in the image being viewed at the time of interrogation with the specific ultrasonic frequency.

Alternatively, the indicator may comprise a chip or other device that resonates at the same general frequency used to visualize the remainder of the fixation device and the surrounding tissue. When the general frequency is used for visualization, the indicator provides a bright visual artifact on an echocardiogram image. This indicates that the tissue is not sufficiently grasped within the target area because the indicator is freely vibrating. Again, if the tissue is compressed between the proximal and distal elements within the target area, the tissue compresses the indicator, reducing or damping the vibration of the indicator. Thus, if the bright visual artifact is not seen at the general ultrasonic frequency, it may be determined that the tissue is sufficiently grasped within the target area of the fixation device. This allows the practitioner to evaluate the grasp by viewing more static images of the echocardiogram. It may be appreciated that the above described ultrasound receiving indicators may both be used with real time ultrasonic images, however one allows evaluation of the grasp based on viewing a dynamic change in an image due to interrogation with a specific ultrasonic frequency and the other allows evaluation of the grasp based on viewing a more static image at a general ultrasonic frequency.

In other embodiments, the fixation device includes a magnetic indicator. The magnetic indicator is typically disposed along a proximal or distal element near a target area. The indicator is used to determine the presence or absence of tissue within the target area thereby assessing the quality of the grasp. The indicator comprises a device, such as a ball bearing, that is movable when a magnetic field is applied. Such a magnetic field may be locally applied, such as by a catheter, or globally applied, such as by magnetic resonance imaging. Movement of the indicator may be visualized by any suitable medium, such as fluoroscopy. Such movement indicates that the tissue is not sufficiently grasped within the target area because the indicator is freely movable. However, if the tissue is compressed between the proximal and distal elements within the target area, the tissue compresses the indicator, reducing or damping the movement of the indicator. Thus, if movement is reduced or not seen when the magnetic field is applied, it may be determined that the tissue is sufficiently grasped within the target area of the fixation device. This allows the practitioner to actively evaluate the grasp.

Figure 29:
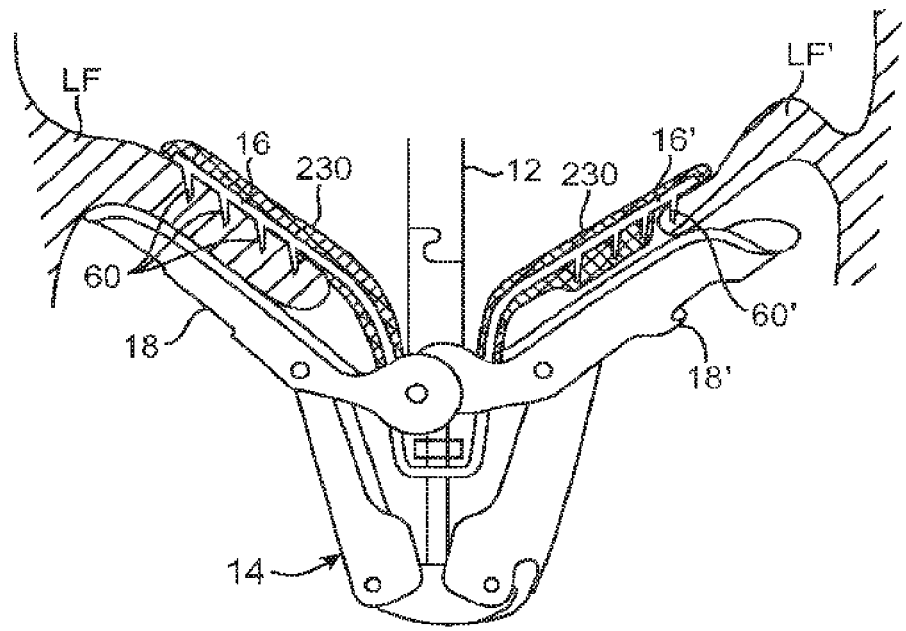
FIG. 29 illustrates a fixation device wherein the position of a grasped leaflet within a fixation device may be determined based on the visibility of frictional elements.

In other embodiments, the position of a grasped leaflet within a fixation device may be determined based on the visibility of frictional elements. Such frictional elements typically have an observable shape, such as barbs, and are coated or comprised of an enhanced visibility material. FIG. 29 illustrates a fixation device 14 having such barbs 60 disposed on the proximal elements 16 as frictional elements. In this embodiment, the proximal elements 16 have a visually opaque or semi-opaque covering 230 which cover the barbs 60. The covering 230 may be comprised of, for example, fibers made from gold or platinum wire or polymer fibers coated or sputtered for radiopacity. When a leaflet LF is grasped and captured between the proximal element 16 and distal element 18, the leaflet LF presses the covering 230 against the proximal element 16 causing the barbs 60 to extend through the covering 230. The exposed barbs 60 are visibly observable by visualization techniques. The quantity and location of visible barbs 60 indicates the position of the grasped leaflet. For example, when a leaflet LF' is grasped and partially captured between the proximal element 16' and distal element 18', only a portion of the barbs 60 (such as single barb 60') are exposed. Thus, the low quantity and outward location of the visible barb 60' indicate that the leaflet LF is not fully captured. The leaflet LF may then be released and regrasped.

Figure 30:
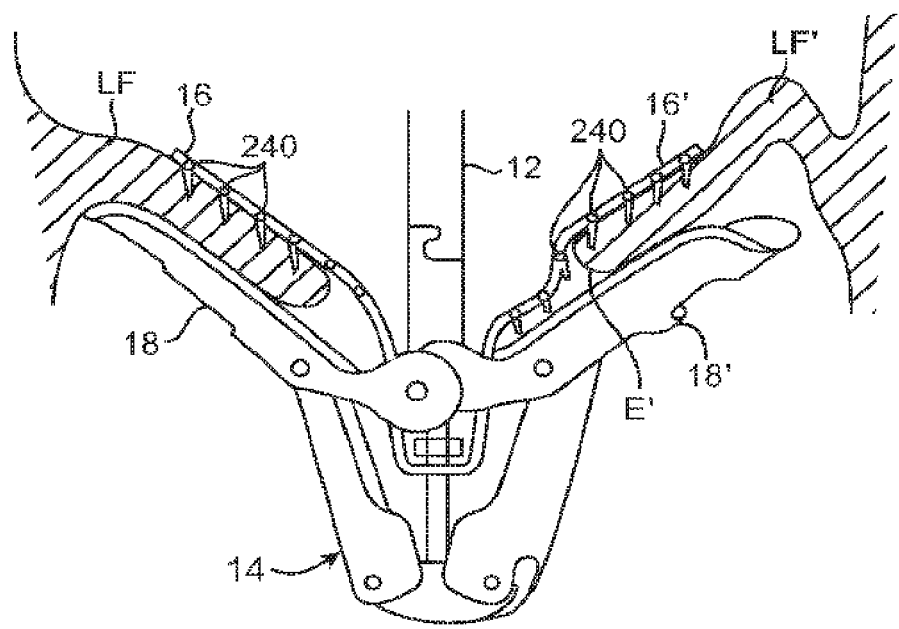
FIG. 30 illustrates a fixation device wherein the proximal elements are comprised of segmental parts separated by hinges or flexible areas.

In still other embodiments, the position of a grasped leaflet within a fixation device may be determined based the visible shape of the proximal elements 16. In such embodiments, the proximal elements 16 may be comprised of segmental parts separated by hinges or flexible areas 240, as illustrated in FIG. 30. The proximal elements 16 are coated or comprised of an enhanced visibility material. When a leaflet LF is grasped and fully captured between the proximal element 16 and distal element 18, the proximal element 16 has a shape which substantially follows the contour of the distal element 18. When a leaflet LF' is grasped and partially captured between the proximal element 16' and distal element 18', the proximal element 16' may flex at a flexible area 240 near an edge E' of the partially captured leaflet LF'. The proximal element 16' may also flex due to a variety of other misorientations of the grasped leaflet LF'. Visualization of the shape of the segmental proximal element indicates the locations in which irregularities occur which may indicate how much of the leaflet has been captured. If the leaflet is not desirably captured, the leaflet LF may then be released and regrasped.

Figure 31A:
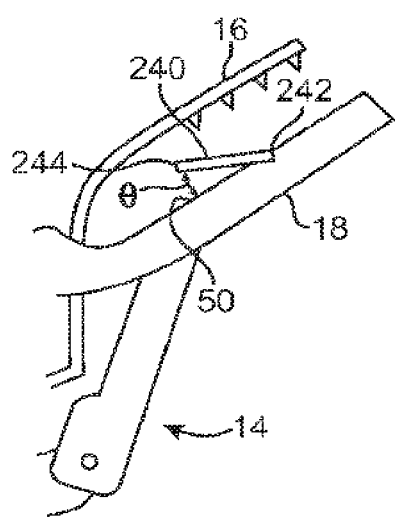
FIGS. 31A-31B, 32A-32C, 33, 34A-34B, 35, 36A-36B illustrate embodiments of a fixation device wherein the position of a grasped tissue within a fixation device is determined based on the visibility of an indicator associated with the distal elements.
Figure 31B:
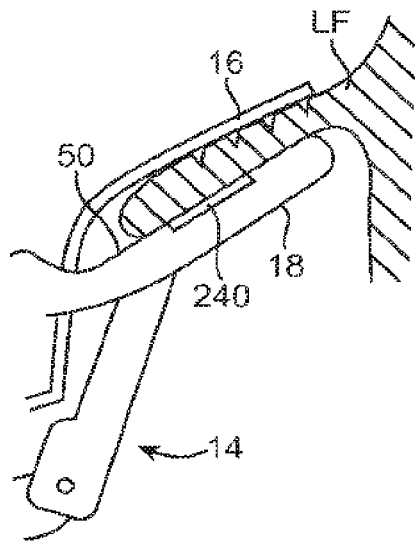

In additional embodiments, the position of a grasped leaflet within a fixation device may be determined based the visibility of an indicator associated with the distal elements 18. For example, FIGS. 31A-31B illustrate an embodiment of a fixation device 14 having a distal element 18 which includes a flap 240. The flap 240 has an attached end 242 which is attached to the engagement surface 50 or a portion of the distal element 18 and a free end 244 which extends toward the proximal element 16. The flap 240 forms an angle θ with the engagement surface 50. The flap 240 is typically flexible or is attached so that the flap 240 is able to move throughout the angle θ. The flap 240 is coated or comprised of an enhanced visibility material so that the practitioner may observe the flap 240 and its angle θ by visualization techniques. In preferred embodiments, the distal element 18 is also coated or comprised of an enhanced visibility material. Prior to grasping a tissue, such as a leaflet, the flap 240 is fully visible and is positioned having a maximum angle θ, as illustrated in FIG. 31A. When a leaflet LF is grasped between the proximal and distal elements 16, 18, the leaflet LF presses the flap 240 toward the engagement surface 50. When the leaflet LF is fully captured, the leaflet LF may press the flap 240 so that it is parallel with or uniform with the engagement surface 50, as illustrated in FIG. 31B. Thus, the lack of observable flap 240 may be an indicator that the leaflet LF has been satisfactorily grasped. Alternatively, the practitioner may be able to determine the extent of grasp or purchase based on the angle θ. For example, flap 240 having an angle (θ/2) may indicate that the leaflet LF only extends half way along the engagement surface 50. If this is not desirable, the leaflet LF may then be released and regrasped. It may be appreciated that the flap 240 may have any suitable shape, size or location, including location on a proximal element 16 or any other suitable element. Further, more than one flap 240 may be present.

Figure 32A:
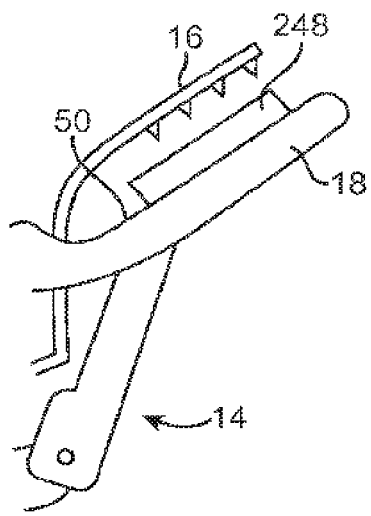
Figure 32B:
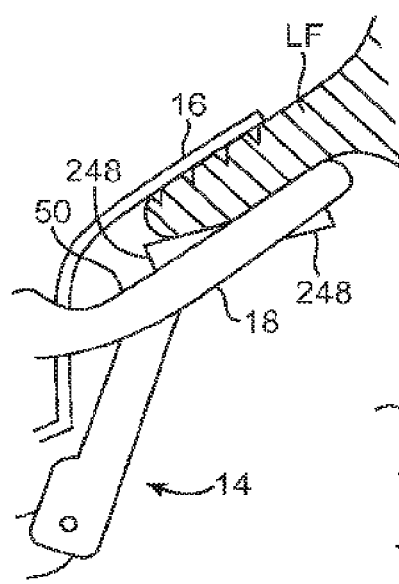
Figure 32C:
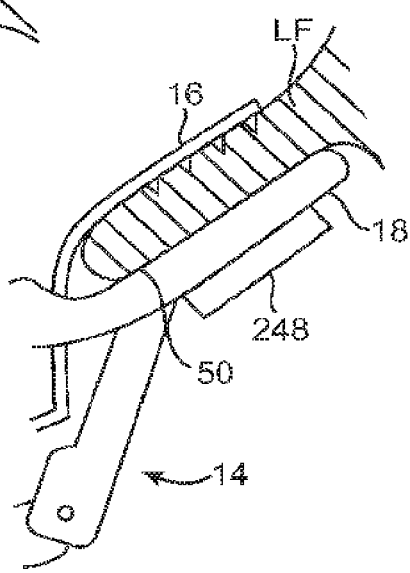

FIGS. 32A-32C illustrate another embodiment wherein the position of a grasped leaflet within a fixation device may be determined based the visibility of an indicator associated with the distal elements 18. Here the indicator comprises a floating block 248 associated with the distal element 18. The floating block 248 is coupled with the distal element 18 so that it may pass through the distal element 18 upon application of force. The block 248 is coated or comprised of an enhanced visibility material so that the practitioner may observe the block 248 by visualization techniques. In preferred embodiments, the distal element 18 is also coated or comprised of an enhanced visibility material. Typically, the block 248 biased, such as spring biased, so that the block 248 is raised toward the proximal element 14, as illustrated in FIG. 32A, prior to grasping a tissue, such as a leaflet. When a leaflet LF is grasped between the proximal and distal elements 16, 18, the leaflet LF presses the block 248 toward the engagement surface 50. When the leaflet LF is partially captured, as illustrated in FIG. 32B, a portion of the block 248 may be visible raised from the engagement surface 50 and a portion may be visible extending from the opposite side. The practitioner may determine the position of the leaflet LF based on the rotation point of the block 248. When the leaflet LF is fully captured, as illustrated in FIG. 32C, the leaflet LF may move the block 248 so that it is fully passed through the distal element 18 and extends outwardly from the opposite side. Thus, the practitioner may determined the desirability of the grasp based on the position of the floating block 248. It may be appreciated that the block 248 may have any suitable shape, size or location including location on a proximal element 16 or any other suitable element. Further, more than one block 248 may be present.

Figure 33:
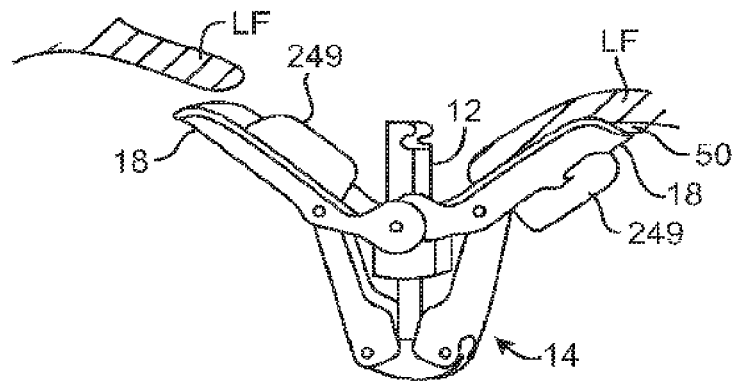

FIG. 33 illustrate an embodiment wherein the indicator comprises a bladder or reservoir 249 associated with the distal element 18. The reservoir 249 is coupled with the distal element 18 so that it may pass through the distal element 18 upon application of force. The reservoir 249 is filled with an enhanced visibility material so that the practitioner may observe the reservoir 249 by visualization techniques. Typically, the reservoir 249 is positioned so that it is raised toward the proximal element 14, as illustrated in the left side of FIG. 33, prior to grasping a tissue, such as a leaflet LF. When a leaflet LF is grasped between the proximal and distal elements 16, 18, as illustrated in the right side of FIG. 33, the leaflet LF presses the reservoir 249 toward the engagement surface 50. When the leaflet LF is partially captured, a portion of the reservoir 249 may be visible raised from the engagement surface 50 and a portion may be visible extending from the opposite side. The practitioner may determine the position of the leaflet LF based on the position of the reservoir 249. When the leaflet LF is fully captured, the leaflet LF may move the reservoir 249 so that it is fully passed through the distal element 18 and extends outwardly from the opposite side. Thus, the practitioner may determined the desirability of the grasp based on the position of the reservoir 249.

Figure 34A:
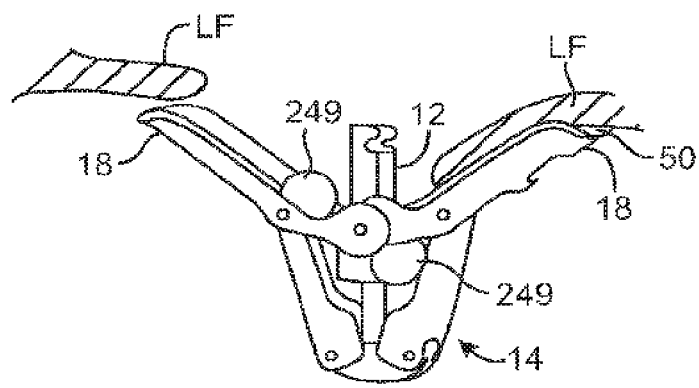
Figure 34B:
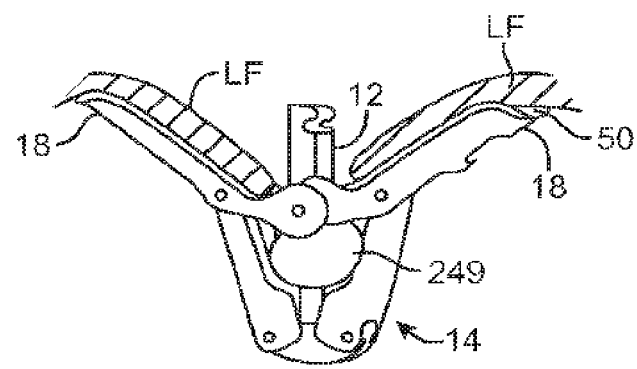

Similarly, as illustrated in FIGS. 34A-34B, the reservoir 249 may have particular size, shape, and/or location so that when both reservoirs 249 are appropriately displaced (indicating both leaflets satisfactorily grasped) the reservoirs 249 may come together to form a distinctive size or volume, as illustrated in FIG. 34B. This may indicate to the practitioner that the leaflets LF are desirably grasped. It may be appreciated that the reservoirs 249 of FIG. 33 and FIGS. 34A-34B may have any suitable shape, size or location including location on a proximal element 16 or any other suitable element. Further, more than one reservoir 249 may be present.

Figure 35:
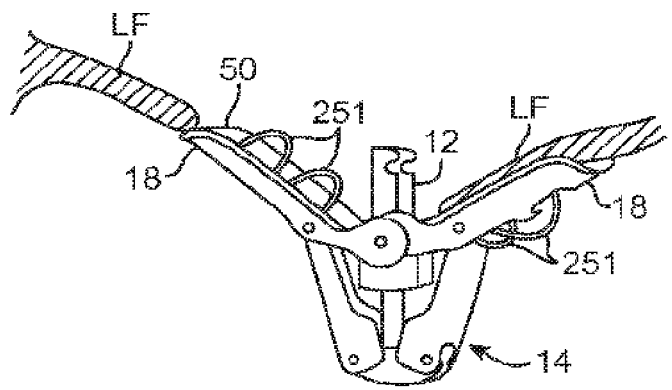

FIG. 35 illustrates another embodiment wherein the position of a grasped leaflet within a fixation device may be determined based the visibility of an indicator associated with the distal elements 18. Here the indicator comprises one or more loops 251, such as wire loops, associated with the distal element 18. The loops 251 are coupled with the distal element 18 so that the loops 251 may pass through the distal element 18 upon application of force. The loops 251 are coated or comprised of an enhanced visibility material so that the practitioner may observe the loops 251 by visualization techniques. Typically, the loops 251 are biased, such as spring biased, so that the loops 251 are raised toward the proximal element 14, as illustrated in the left side of FIG. 35, prior to grasping a tissue, such as a leaflet LF. When a leaflet LF is grasped between the proximal and distal elements 16, 18, the leaflet LF presses the loops 251 toward the engagement surface 50. When the leaflet LF is fully captured, as illustrated in the right side of FIG. 35, the leaflet LF may move the loops 251 so that they are fully passed through the distal element 18 and extend outwardly from the opposite side. Thus, the practitioner may determine the desirability of the grasp based on the position of the loops 251. It may be appreciated that the loops 251 may have any suitable shape, size or location including location on a proximal element 16 or any other suitable element.

Figure 36A:
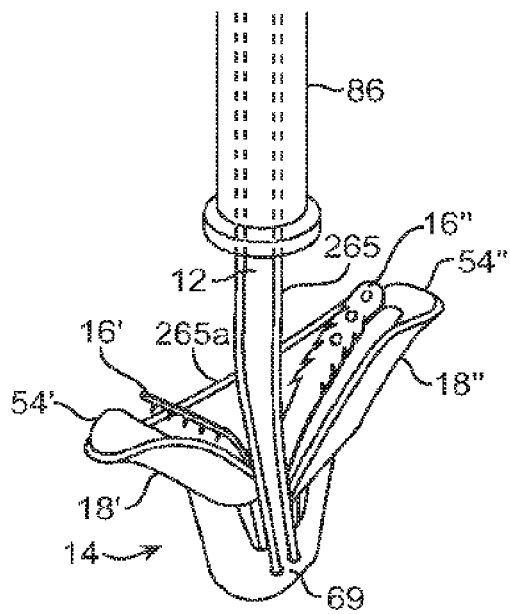
Figure 36B:
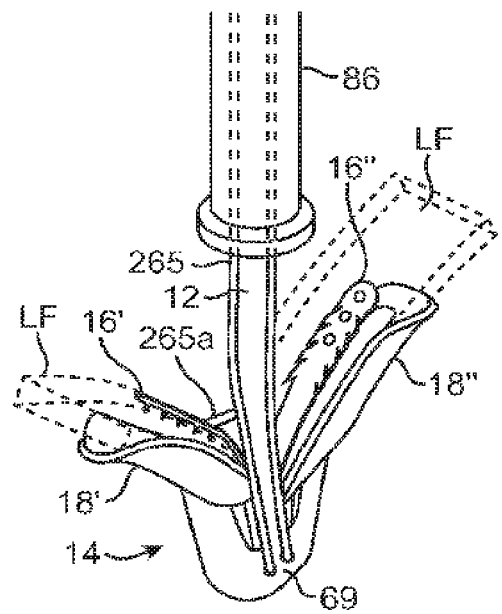

FIGS. 36A-36B illustrate another embodiment wherein the position of a grasped leaflet within a fixation device may be determined based the visibility of an indicator associated with the distal elements 18. Here the indicator comprises at least one slackline 265, such a wire, suture, thread, filament, polymer, or strand, which extends around portions of the fixation device 14. In this embodiment, as shown in FIG. 36A, the slackline 265 extends through a lumen in catheter 86 and along the shaft 12 toward the base 69 of the fixation device 14. The slackline 265 then extends around a free end 54' of one of the distal elements 18' and continues across to a free end 54" of the opposite distal element 18", creating an indicator segment 265a between the distal elements 18', 18". The slackline 265 then extends toward the base 69 and returns along the shaft 12 to another lumen (or the same lumen) in catheter 86. The slackline 265 is coated or comprised of an enhanced visibility material so that the practitioner may observe the slackline 265 by visualization techniques. The slackline 265 also has sufficient slack to allow movement of at least the indicator segment 265a when force is applied, such as by a leaflet. FIG. 36B illustrates the fixation device 14 of FIG. 36A wherein a pair of leaflets LF are desirably grasped. Here, desirable positioning of the leaflets between the proximal elements 16', 16" and distal elements 18', 18" forces the indicator segment 265a into a different configuration, in this case lowering the indicator segment 265a. Thus, the practitioner may determine the desirability of the grasp based on the position of the indicator segment 265a. It may be appreciated that the indicator segment 265a and/or the slackline 265 may have any configuration, and more than one slackline 265 may be present.

Figure 37A:
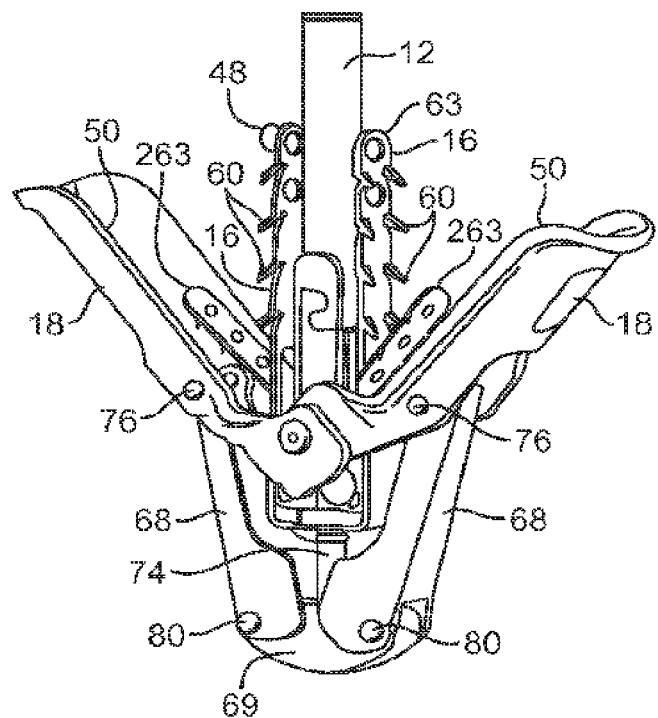
FIGS. 37A-37B illustrate embodiments of a fixation device having mini-grippers.

In other embodiments, the position of one or more leaflets LF within the fixation device 14 may be determined or verified prior to releasing of the proximal elements 16. For example, FIG. 37A illustrates an embodiment of a fixation device 14 having mini-grippers 263 which may be shaped similarly to the proximal elements 16 yet are smaller in size. Each mini-gripper 263 is disposed between a set of proximal and distal elements 16, 18. The fixation device 14 is positioned to so that the leaflets are engaged by the engagements surfaces 50 of the distal elements 18. The mini-grippers 263 are then released, each extending radially outwardly from the shaft 12 a short distance along the engagement surfaces 50 of the distal elements 18. It may be appreciated that the mini-grippers 263 may be released independently or simultaneously. If the mini-grippers 263 grasp the leaflets, it may be determined that the leaflets are adequately positioned within the fixation device 14 since such grasping indicates that the leaflets extend to a desired distance relative to the shaft 12. Once desired grasping of the leaflets is determined, the proximal elements 16, may be released to grasp the leaflets between the proximal and distal elements 16, 18. The mini-grippers 263 may remain in place or be removed.

Alternatively, both the mini-grippers 263 and the proximal elements 16 may be deployed simultaneously. The proximal elements 16 may then be raised or released while the mini-grippers 263 remain deployed, thereby confirming whether the leaflets are still held by the mini grippers 263. If the mini-grippers 263 still hold the leaflets, it may be determined that the leaflets are adequately positioned within the fixation device 14 since such grasping indicates that the leaflets extend to a desired distance relative to the shaft 12. Once desired grasping of the leaflets is determined, the proximal elements 16, may be re-released to grasp the leaflets between the proximal and distal elements 16, 18. The mini-grippers 263 may remain in place or be removed.

Figure 37B:
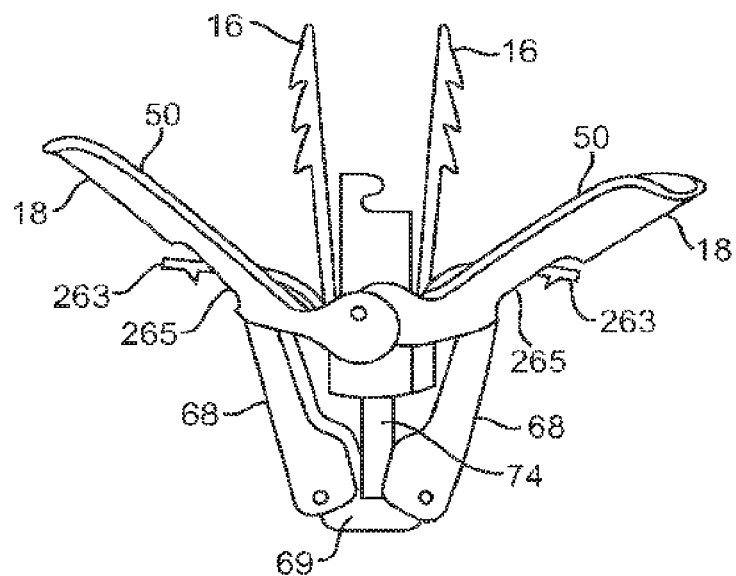

In yet other embodiments, as illustrated in FIG. 37B, the mini-grippers 263 may extend through a window 265 or space in the distal elements 18 if the released mini-grippers 263 do not contact the leaflets in the target area. Thus, visualization of the mini-grippers 263 extending beyond the distal elements 18, as shown, indicates that the leaflets have not been desirably grasped. Such visualization may be achieved prior to or after release of the proximal elements 16. When the mini-grippers 263 are released simultaneously with the proximal elements 16, such visualization allows grasping assessment to be achieved without additional movement of the proximal elements 16.

Figure 38A:
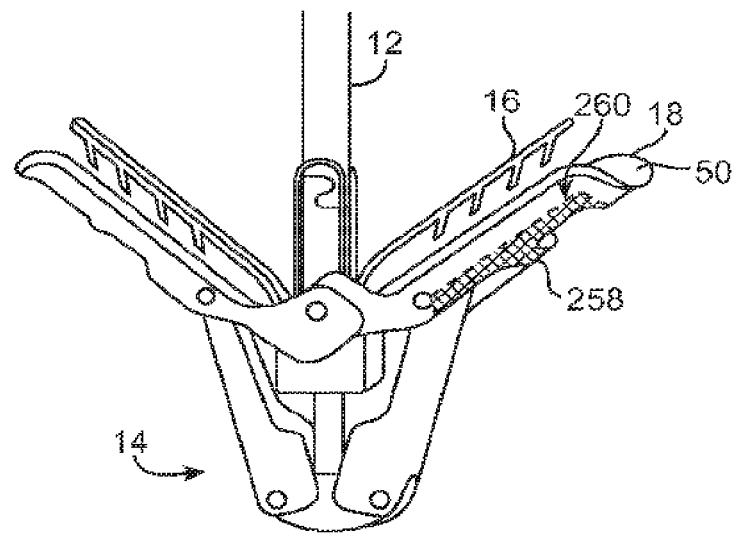
FIGS. 38A-38B illustrate an embodiment having a reservoir within the distal elements which releases a substance
Figure 38B:
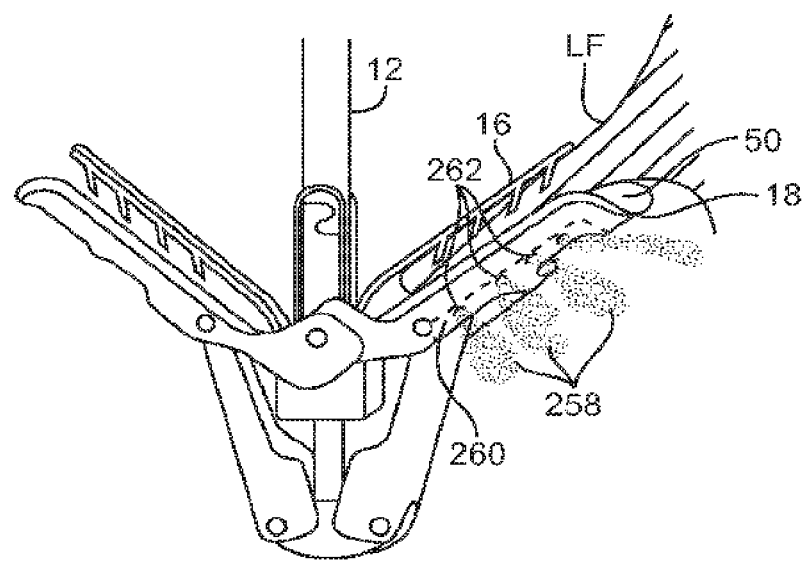

In other embodiments, the position of a grasped leaflet within a fixation device may be determined based the visibility of a released substance which is visible under visualization techniques, such as liquid contrast material or bioabsorbable polymer beads having air bubbles trapped within. In one embodiment illustrated in FIG. 38A, the substance 258 is contained in a bladder or reservoir 260 within the distal element 18. When a leaflet LF is grasped between the proximal and distal elements 16, 18, the leaflet LF presses the reservoir 260 releasing the substance 258 through ports 262, as illustrated in FIG. 38B. The ports 262 may be disposed along the length of the distal element 18 so that the substance 258 is expelled through the ports 262 only in the areas where the leaflet LF is engaged. Therefore, the practitioner may be able to determine the extent of grasp or purchase based on the location and/or amount of expelled substance 258. It may be appreciated that the reservoir 260 may have any suitable shape, size or location, including location on a proximal element 16 or any other suitable element. Further, more than one reservoir 260 may be present.

Figure 39A:
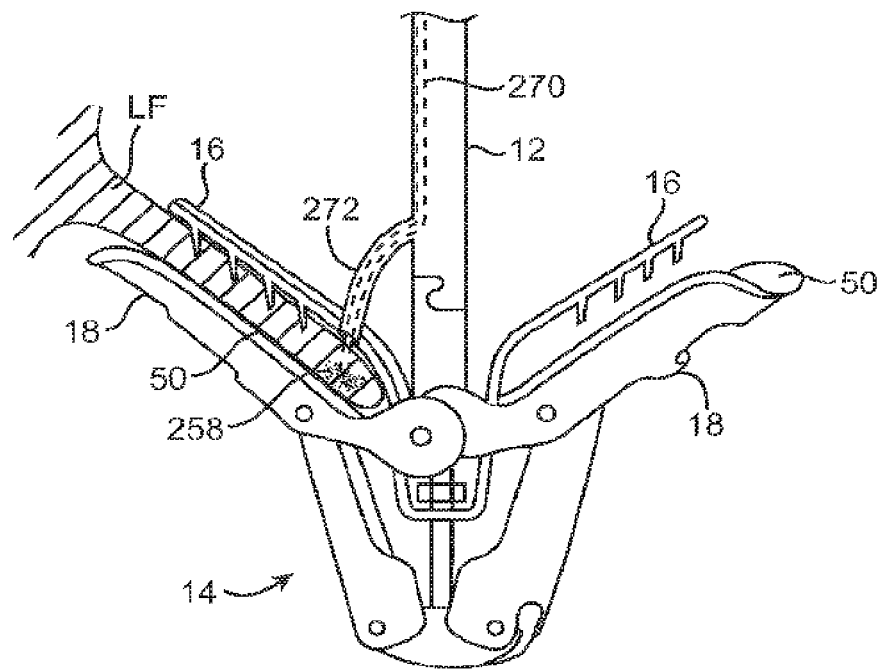
FIGS. 39A-39B illustrate an embodiment of a fixation device wherein the position of the grasped tissue within a fixation device is determined based on the visibility of a released substance from a conduit.
Figure 39B:
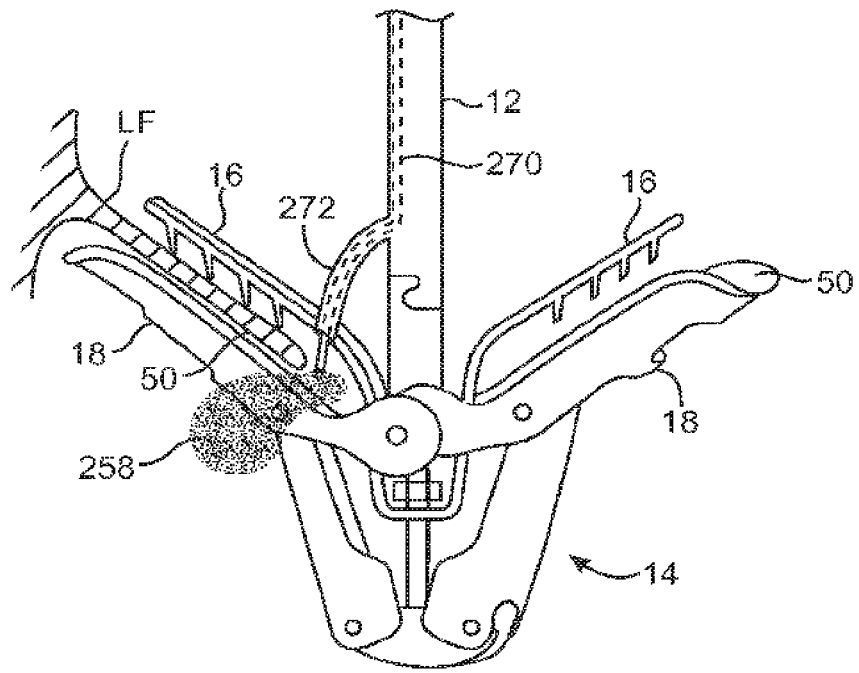

Another embodiment, illustrated in FIGS. 39A-39B, the position of a grasped leaflet LF within a fixation device 14 is also determined based the visibility of a released substance which is visible under visualization techniques, such as liquid contrast material or bioabsorbable polymer beads having air bubbles trapped within. Here, the substance 258 is released through a lumen 270 which extends through the shaft 12 of the fixation device 14 and through an conduit 272, as illustrated in FIG. 39A. The conduit 272 is directed toward a target area of the engagement surface 50 of the distal element 18. The target area is positioned so that a grasped leaflet LF covering the target area is considered sufficiently grasped. When a leaflet LF covers the target area, as illustrated in FIG. 39A, the released or injected substance 258 is blocked by the leaflet LF. Such blockage may either prevent injection of the substance 258, cause injection of the substance 258 into the leaflet LF, or allow some visibility of the substance 258 on the side of the leaflet LF receiving the injected substance 258. Thus, the practitioner may determine that the leaflet LF is satisfactorily grasped due to the lack of or reduced quantity of substance 258 or the location of the injected substance 258 (i.e. within the leaflet or on the side of the leaflet receiving the injected substance 258). When a leaflet LF does not cover the target area, as illustrated in FIG. 39B, the released or injected substance 258 is not blocked by the leaflet LF. Therefore, the substance 258 will be injected into the area between the proximal and distal elements 16, 18 and is free to extravagate into the circulation. Thus, the practitioner may determine that the leaflet LF is not satisfactorily grasped due to the visibility of extravagated substance 258. It may be appreciated that the conduit 272 may have a variety of forms, sizes and orientations and may be directed toward a variety of target areas. Further, more than one conduit 272 may be present. It may also be appreciated that needles, tubes or other instruments may be advanced through the conduit 272 to deliver the substrate or for any other purpose.

It may also be appreciated that the above described lumen 270 and conduit 272 may alternatively be used to draw suction. When a leaflet LF covers the target area, as illustrated in FIG. 39A, suction drawn through the conduit 272 will cause the leaflet LF to press against the conduit 272 preventing blood from entering the conduit 272. However, when a leaflet LF does not cover the target area, blood will be suctioned up through the conduit 272. Therefore, the practitioner may determine whether the leaflet LF is satisfactorily grasped based on the presence of blood suctioned through the conduit 272.

Figure 40A:
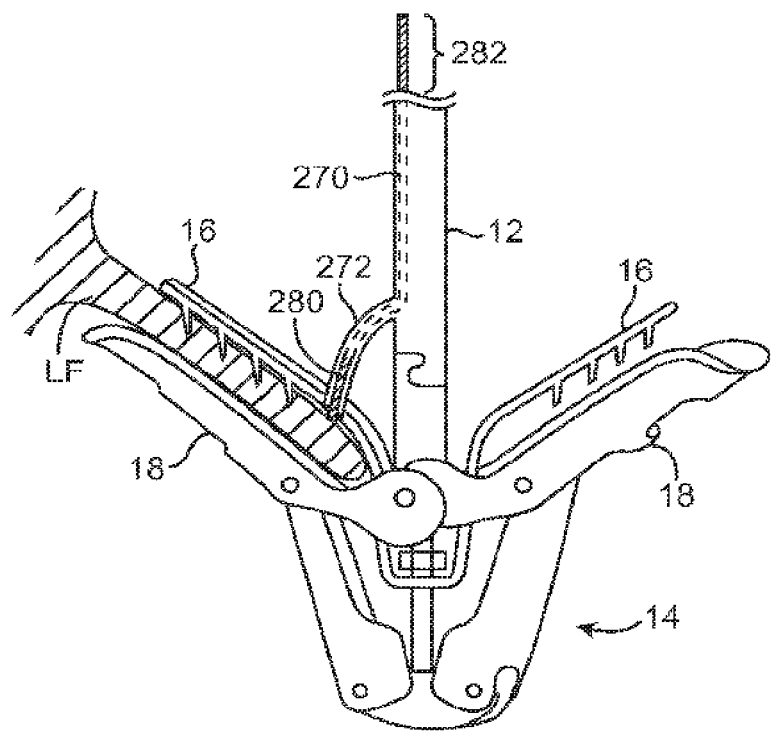
FIGS. 40A-40B illustrate an embodiment of a fixation device having a probe connected with an insertion depth gauge to determine if a tissue has been desirably grasped.
Figure 40B:
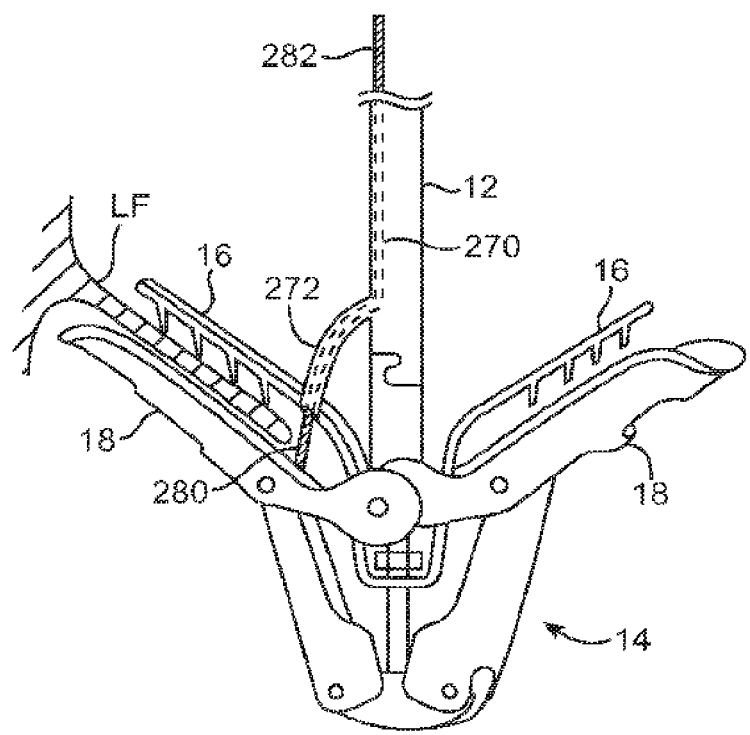

Similarly, an embodiment, illustrated in FIGS. 40A-40B, is provided having a lumen 270 which extends through the shaft 12 of the fixation device 14 and through a conduit 272. Again, the conduit 272 is directed toward a target area of the engagement surface 50 of the distal element 18. The target area is positioned so that a grasped leaflet LF covering the target area is considered sufficiently grasped. In this embodiment, a probe 280 is advanceable through the lumen 270. In addition, the probe 280 is connected with an insertion depth gauge 282 so that the practitioner is able to determine the advancement distance of the probe 280. When a leaflet LF covers the target area, as illustrated in FIG. 40A, the probe 280 may only be advanced until it contacts the leaflet LF. Thus, the practitioner may determine that the leaflet LF is satisfactorily grasped due to the minimal advancement distance indicated by the insertion depth gauge 282. When a leaflet LF does not cover the target area, as illustrated in FIG. 40B, the probe 280 is able to advance further toward the distal element 18. Thus, the practitioner may determine that the leaflet LF is not satisfactorily grasped due to the advancement distance. Again, it may be appreciated that the conduit 272 may have a variety of forms, sizes and orientations and may be directed toward a variety of target areas. Further, more than one conduit 272 may be present.

Figure 41A:
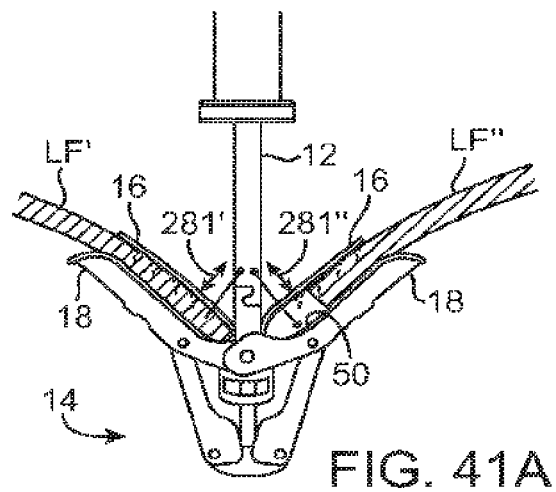
FIGS. 41A-41F illustrate embodiments of fixation devices having detectable elements extending toward the engagement surfaces to determine if a tissue has been desirably grasped.
Figure 41B:
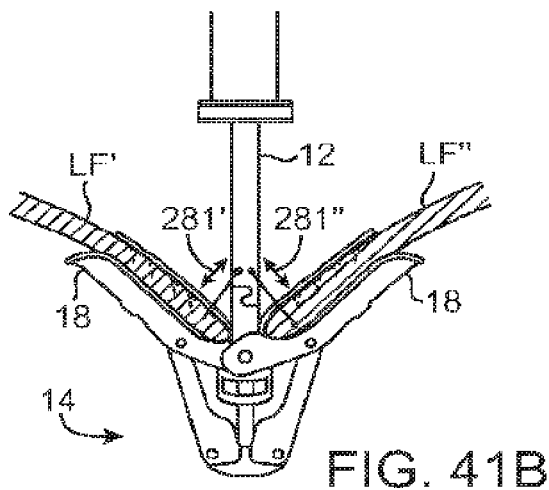

Similarly, as illustrated in FIGS. 41A-41F, detectable elements 281 may extend from the shaft 12 of the fixation device 14. In FIGS. 41A-41B, the detectable elements 281 are coupled with the proximal elements 16 so that release of each proximal element 16 draws an associated detectable element 281 toward a target area of the engagement surface 50 of the associated distal element 18. Each target area is positioned so that a grasped leaflet LF covering the target area is considered sufficiently grasped. When a leaflet LF' covers its corresponding target area, as illustrated in the left side of FIG. 41A, the detectable element 281' contacts the leaflet LF'. When a leaflet LF" does not cover its corresponding target area, as illustrated in the right side of FIG. 41A, the detectable element 281" is able to advance toward the target area, extending a further distance than if a leaflet were present. The detectable elements 281', 281" are comprised of a detectable material or coating, such as a material which is detectable by fluoroscopy, conductance or impedance signal. Therefore, the practitioner is able to detect the position of the detectable elements 281', 281" and consequently determine if the leaflets are desirably grasped, as illustrated in FIG. 41B. The detectable elements 281', 281" are then released from the proximal elements 16 and removed upon detachment of the fixation device 14. It may be appreciated that the detectable elements 281 may be individually extendable from the shaft 12 (i.e. not coupled with the proximal elements 16). Also, in other embodiments, the detectable elements 281 may form a circuit when contacting the engagement surface 50 of the associated distal element 18. For example, when a leaflet LF' covers its corresponding target area, the detectable element 281' contacts the leaflet LF', such as illustrated above in the left side of FIG. 41A. Thus, the detectable element 281' does not contact the engagement surface 50 and the circuit remains open. When a leaflet LF" does not cover its corresponding target area, such as illustrated in the right side of FIG. 41A, the detectable element 281" is able to advance toward the target area and contact the engagement surface, completing the circuit. The integrity of the circuit may be detected by any suitable device, such as an ohmmeter or an ammeter, thereby indicating if the leaflets are desirably grasped.

Figure 41C:
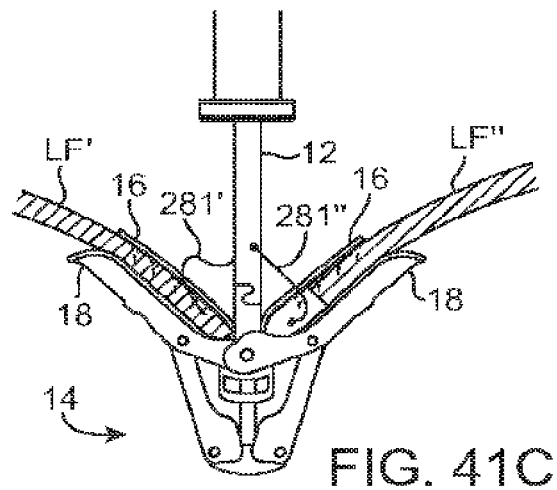
Figure 41D:
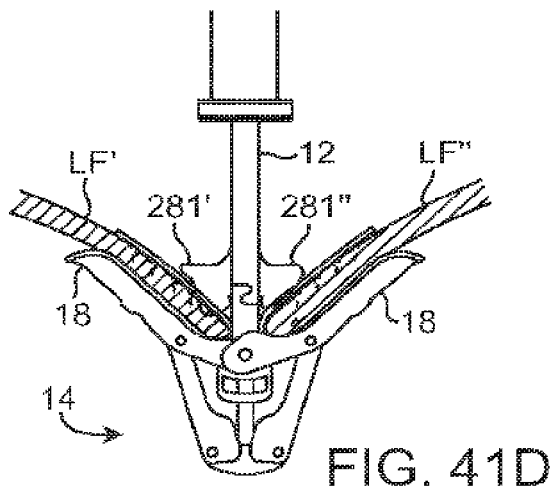

In FIGS. 41C-41D, the detectable elements 281 are each advanceable from the shaft 12 toward a target area of the engagement surface 50 of its associated distal element 18. When a leaflet LF' covers its corresponding target area, as illustrated in the left side of FIG. 41C, the detectable element 281' contacts the leaflet LF' and creates a first shape. When a leaflet LF" does not cover its corresponding target area, as illustrated in the right side of FIG. 41C, the detectable element 281" is able to advance toward the target area, creating a second shape which differs from the first shape. The detectable elements 281', 281" are comprised of a detectable material or coating, such as a material which is detectable by fluoroscopy or by impedance signal. Therefore, the practitioner is able to detect the shapes of the detectable elements 281. When both leaflets are desirably grasped, both detectable elements 281', 281" will substantially form the first shape, as illustrated in FIG. 41D.

Figure 41E:
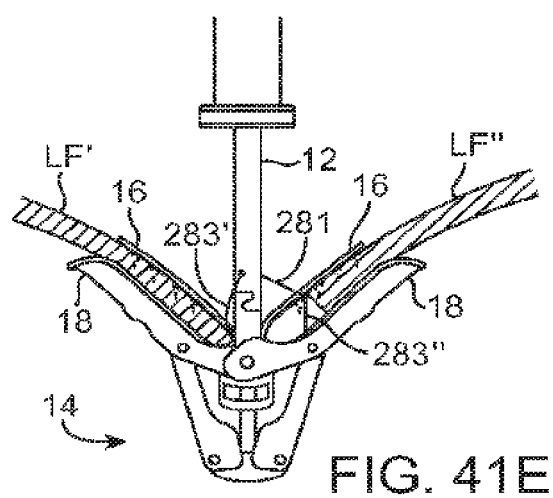
Figure 41F:
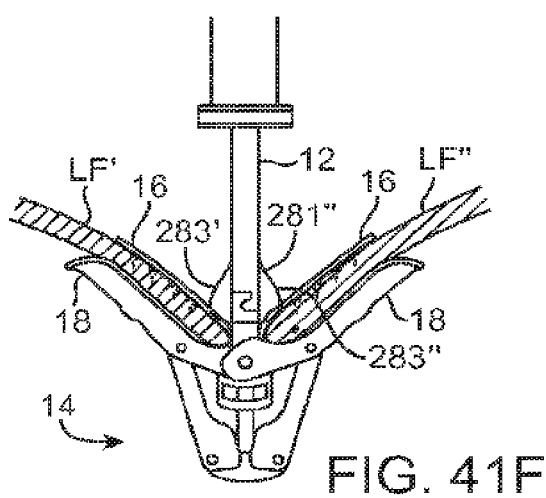

In FIGS. 41E-41F, a single detectable element 281 is advanceable from the shaft 12 toward target areas of the engagement surfaces 50 of the distal elements 18. When a leaflet LF' covers its corresponding target area, as illustrated in the left side of FIG. 41E, a portion 283' of the detectable element 281 contacts the leaflet LF' and creates a first shape. When a leaflet LF" does not cover its corresponding target area, as illustrated in the right side of FIG. 41F, a portion 283" of the detectable element 281 is able to advance toward the target area, creating a second shape which differs from the first shape. The detectable element 281 is comprised of a detectable material or coating, such as a material which is detectable by fluoroscopy or by impedance signal. Therefore, the practitioner is able to detect the shape of the portions 283' 283" of the detectable element 281. When both leaflets are desirably grasped, both portions 283' 283" of the detectable element 281 will substantially form the first shape, as illustrated in FIG. 41F, creating a symmetrical shape.

Figure 42A:
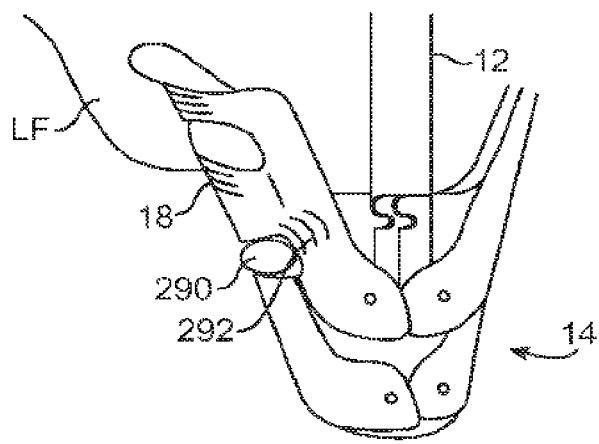
FIG. 42A-42B illustrate a fixation device having at least one sensor disposed on or within a distal element.
Figure 42B:
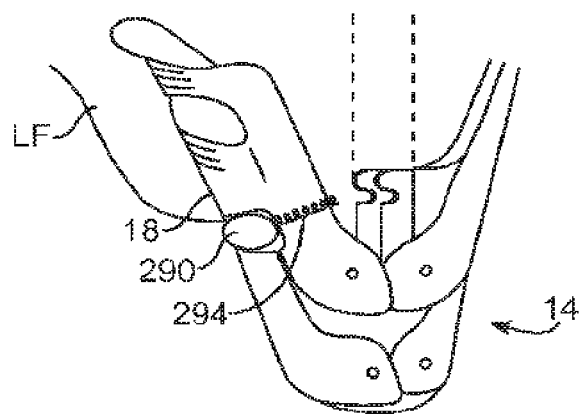
Figure 43:
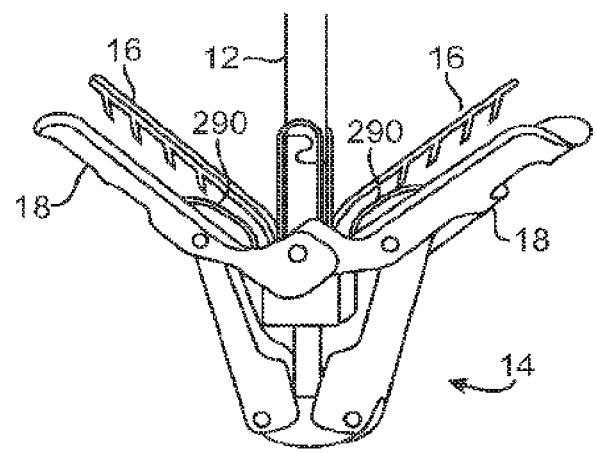
FIG. 43 illustrate a fixation device having sensors which extend into a target area between the proximal and distal elements.

In some embodiments, the fixation device includes one or more sensors to determine the position of a grasped tissue. Typically, the sensor determines the presence or absence of tissue on or near the sensor. For example, FIGS. 42A-42B illustrate a fixation device 14 having at least one sensor 290 disposed on or within a distal element 18. In this embodiment, the sensor 290 is positioned near the shaft 12 to determine if a grasped leaflet LF is fully inserted into the fixation device 14 or only partially inserted. As shown in FIG. 42A, the sensor 290 may emit a first signal 292 when the leaflet LF is not detected near the sensor 290 indicating that the leaflet LF is not fully engaged. When the leaflet LF is fully engaged, as illustrated in FIG. 42B, the sensor 290 detects the leaflet LF near the sensor 290 and emits a second signal 294, which differs from the first signal 292. The sensor 290 may have any suitable form, such as a conductor, a strain gauge, a radiosensor, an optical sensor, an ultrasound sensor, an infrared sensor, an electrical resistance sensor, an intravascular ultrasound (IVUS) sensor or a pressure sensor, to name a few. Alternatively, the sensor 290 may comprise a resonating sensor that responds to magnetic energy in the fixation device 14 to indicate leaflet insertion. For example, magnetic energy may be applied to the fixation device 14 wherein the sensor 290 does not resonate or is not activated if the leaflet is not sufficiently inserted. It may be appreciated that any number of sensors 290 may be present and may be disposed on or within any element, including the proximal elements 16. FIG. 43 illustrates a fixation device 14 having sensors 290 which extend into a target area between the proximal and distal elements 16, 18.

Figure 44A:
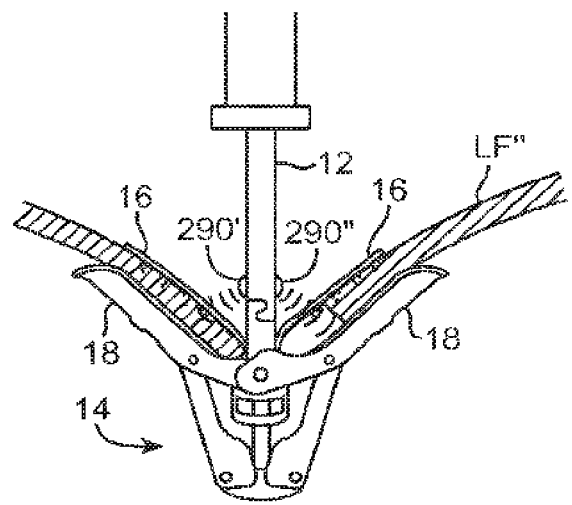
FIGS. 44A-44B illustrate a fixation device having sensors positioned on the shaft.
Figure 44B:
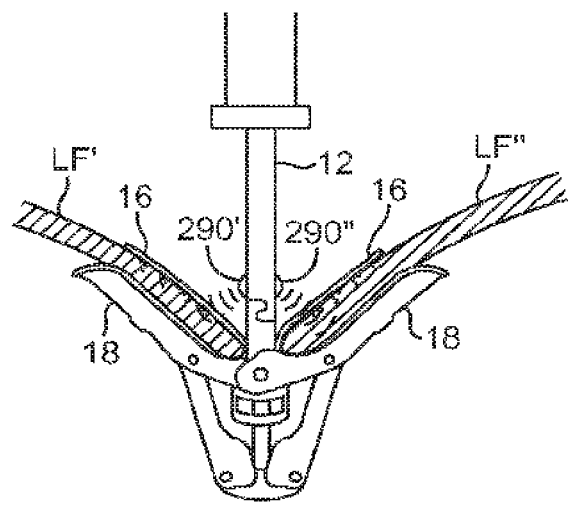

FIGS. 44A-44B illustrate a fixation device 14 having sensors 290', 290" positioned on the shaft 12. In this embodiment, the sensors 290', 290" emit ultrasound signals toward a portion of the distal elements 18 near the shaft 12. In FIG. 44A, leaflet LF'" is not detected by the sensor 290" since the leaflet LF'" is not grasped between the corresponding proximal and distal elements 16, 18 and the leaflet LF'" does not extend into the path of the emitted signals. The practitioner may then reposition the fixation device 14. FIG. 44B illustrates a fixation device 14 having both leaflets LF', LF" desirably grasped so that both sensors 290', 290" sense the leaflets LF', LF".

It may also be appreciated that sensors may be used to actuate movement of the fixation device. For example, sensors in the form of strain gauges may be disposed on each of the distal elements. Engaging the distal elements with the leaflets applied tension to the distal elements which is measurable by the strain gauges. Therefore, when the strain gauges measure a predetermined quantity, the proximal elements may be automatically lowered to grasp the leaflets therebetween. It may be appreciated that the strain gauge measurements may be used to actuate a variety of other movements or simply indicate to the practitioner that such movements are acceptable.

V. Fixation Assessment

Once the quality of the grasp of the tissue has been assessed, it is often desired to evaluate or assess the quality of the fixation of the tissue. This can be achieved by evaluating the improvement in the medical condition being treated. In the case of valve leaflet fixation, improvement in regurgitation may be evaluated. It is often desired to assess the fixation prior to decoupling the fixation device from the delivery catheter so that the fixation device may be repositioned if the improvement is not satisfactory. Thus, a variety of devices and techniques are provided to assess the fixation prior to decoupling the fixation device from the delivery catheter. It may be appreciated that the assessment devices and techniques may be used in combination with the above described fixation devices or may be used with any suitable grasping and/or fixing device. Further, many of such assessment devices and techniques may be used to assess fixation for any purpose.

Figure 45A:
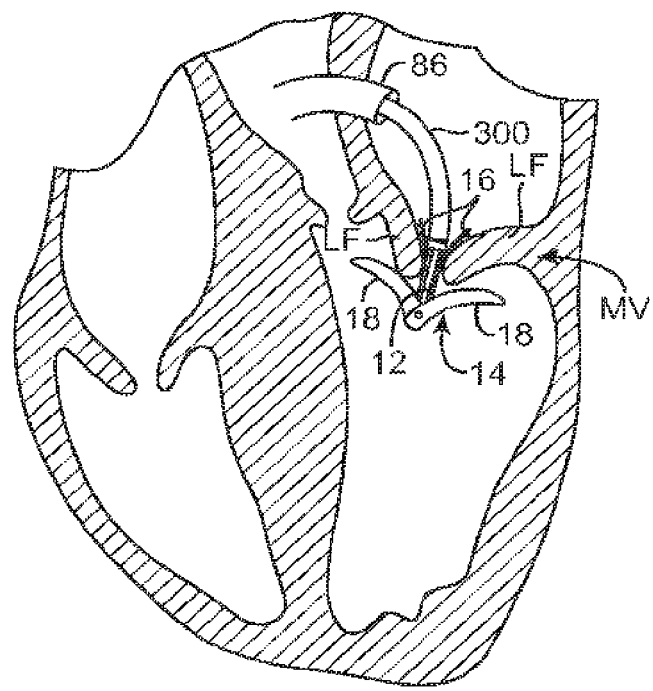
FIG. 45A-45B, 46A-46B illustrate fixation devices and methods for simulating the resultant placement and function of a fixation device that has been positioned to grasp leaflets of the mitral valve.
Figure 45B:
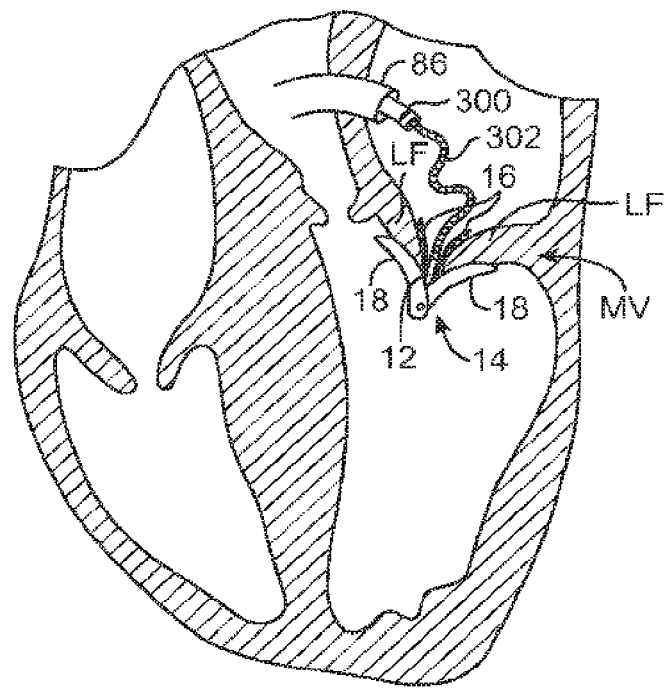

FIGS. 45A-45B illustrate an embodiment of devices and methods for simulating the resultant placement and function of a fixation device 14 that has been positioned to grasp leaflets LF of the mitral valve MV. In this embodiment, the fixation device 14 is delivered to the mitral valve MV by a catheter 86. The fixation device 14 is removably coupled to a shaft 12 which is passed through a catheter 86. In addition, a sheath 300 is provided which passes through the catheter 86 and over the shaft 12 to provide support while the fixation device 14 is positioned within the valve MV and the leaflets LF are grasped between the proximal and distal elements 16, 18. Once the leaflets LF are satisfactorily grasped, the sheath 300 may be retracted, as illustrated in FIG. 45B. Retraction of the sheath 300 exposes a flexible linkage 302 which extends from the shaft 12 to the catheter 86. The flexible linkage 302 allows the fixation device 14 to move freely, mimicking the behavior of the fixation device 14 after decoupling from the shaft 12. The improvement in regurgitation may then be assessed. If the improvement is considered unsatisfactory, the sheath 300 may be advanced to cover the flexible linkage 302 and provide support for repositioning of the fixation device 14. Upon repositioning, the sheath 300 may then be retracted and the function of the valve again assessed. This may be repeated as many times as desired. Once the improvement is considered satisfactory, the fixation device 14 may be decoupled from the shaft 12.

Figure 46A:
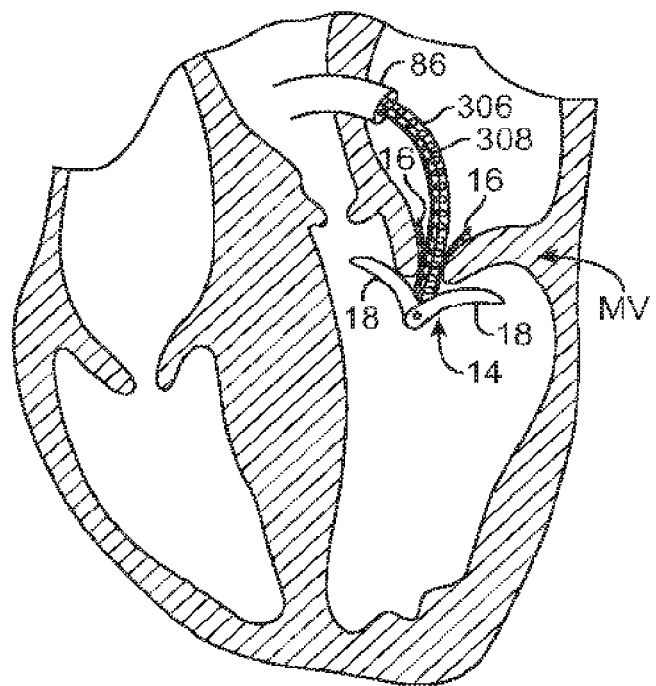
Figure 46B:
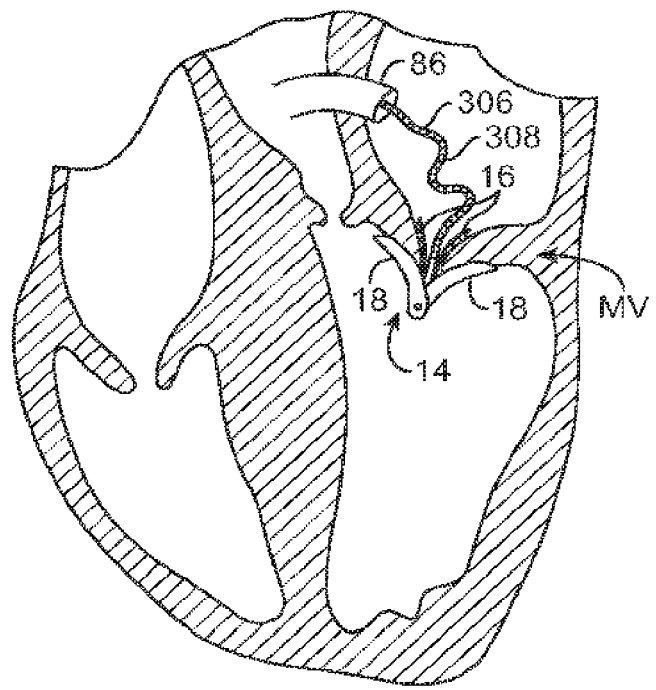

Similarly, FIGS. 46A-46B also illustrate an embodiment of devices and methods for simulating the resultant placement and function of a fixation device 14 that has been positioned to grasp leaflets LF of the mitral valve MV. In this embodiment, the fixation device 14 is delivered to the mitral valve MV by a catheter 86. The fixation device 14 is removably coupled to a shaft 12 which is passed through a catheter 86. Here, the shaft 12 is comprised of a flexible structure 306, such as a compression coil, that is held rigid by a center actuation wire 308. The wire 308 is held taught to provide support while the fixation device 14 is positioned within the valve MV and the leaflets LF are grasped between the proximal and distal elements 16, 18. Once the leaflets LF are satisfactorily grasped, the wire 308 tension is released to allow the flexible structure 306 to flex which allows the fixation device 14 to move freely, mimicking the behavior of the fixation device 14 after decoupling from the shaft 12. The improvement in regurgitation may then be assessed. If the improvement is considered unsatisfactory, the tension may be reapplied to the wire 308 to provide support for repositioning of the fixation device 14. Upon repositioning, tension may again be released and the function of the valve assessed. This may be repeated as many times as desired. Once the improvement is considered satisfactory, the fixation device 14 may be decoupled from the shaft 12.

In other embodiments, the fixation device may be decoupled from the shaft while maintaining a tether, such as a suture line, to the catheter. This allows the fixation device 14 to be evaluated while it is decoupled from the shaft but provides assistance in retrieval of the fixation device for repositioning. The tether may be present specifically for this purpose, or other elements used in the positioning of the fixation device 14 may be used as a tether, such as a lock line 92 or a proximal element line 90. Alternatively, a snare may be extended from the catheter 86 to retrieve the fixation device 14. In any case, the fixation device may be retrieved with the tether, recoupled with the shaft 12 and repositioned until a satisfactory result is achieved.

Although the foregoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. A fixation device, comprising:
   a first distal element and a second distal element;
   a first proximal element moveable relative to the first distal element between a first position of the first proximal element and a second position of the first proximal element to grasp a first leaflet of a heart valve in a first target area defined by the first proximal element and the first distal element;
   a second proximal element moveable relative to the second distal element between a first position of the second proximal element and a second position of the second proximal element to grasp a second leaflet of the heart valve in a second target area defined by the second proximal element and the second distal element;
   a first indicator coupled with the first distal element to indicate a presence of the first leaflet in the first target area, wherein the first indicator extends into the first target area and is configured to pass through the first distal element by the presence of the first leaflet grasped within the first target area; and
   a second indicator coupled with the second distal element to indicate a presence of the second leaflet in the second target area, wherein the second indicator extends into the second target area and is configured to pass through the second distal element by the presence of the second leaflet grasped within the second target area.

2. The fixation device of claim 1, wherein the first indicator is configured to change its orientation by the presence of the first leaflet grasped within the first target area; and
   wherein the second indicator is configured to change its orientation by the presence of the first leaflet grasped within the first target area.

3. The fixation device of claim 1, wherein the first indicator comprises an enhanced visibility material viewable using a visualization technique; and
   wherein the second indicator comprises an enhanced visibility material viewable using the visualization technique.

4. The fixation device of claim 3, wherein the first distal element comprises an enhanced visibility material viewable using the visualization technique; and
   wherein the second distal element comprises an enhanced visibility material viewable using the visualization technique.

5. The fixation device of claim 3, wherein the visualization technique comprises at least one of fluoroscopy, ultrasound, and echocardiography.

6. The fixation device of claim 1, wherein the first indicator comprises one or more wire elements; and
   wherein the second indicator comprises one or more wire elements.

7. The fixation device of claim 6, wherein the one or more wire elements of the first indicator comprise an enhanced visibility material viewable using a visualization technique; and
   wherein the one or more wire elements of the second indicator comprise an enhanced visibility material viewable using the visualization technique.

8. The fixation device of claim 6, wherein the one or more wire elements of the first indicator are biased towards the first proximal element; and
   wherein the one or more wire elements of the second indicator are biased towards the second proximal element.

9. The fixation device of claim 1, wherein:
   the first indicator is configured to extend outwardly from a side of the first distal element opposite the first target area upon passing through the first distal element, and
   the second indicator is configured to extend outwardly from a side of the second distal element opposite the second target area upon passing through the second distal element.

10. The fixation device of claim 9, wherein:
    the first distal element has a first engagement surface defining a first concave recess, the first indicator being positioned at least partially within the concave recess when the first leaflet is not present within the first target area, and
    the second distal element has a second engagement surface defining a second concave recess, the second indicator being positioned at least partially within the second concave recess when the second leaflet is not present within the second target area.

11. The fixation device of claim 9, wherein the first and second indicators are each comprised of wire loops coated with enhanced visibility material visible by a visualization technique and are biased toward the first and second proximal elements, respectively.

12. A fixation device, comprising: a first distal element and a second distal element; a first proximal element moveable relative to the first distal element between a first position of the first proximal element and a second position of the first proximal element to grasp a first leaflet of a heart valve in a first target area defined by the first proximal element and the first distal element; a second proximal element moveable relative to the second distal element between a first position of the first proximal element and a second position of the first proximal element to grasp a second leaflet of the heart valve in a second target area defined by the second proximal element and the second distal element; a first indicator coupled with the first distal element to indicate a presence of the first leaflet in the first target area, wherein the first indicator is moveable from a first configuration to a second configuration by the presence of the first leaflet grasped within the first target area, wherein, in the first configuration of the first indicator, the first indicator extends from a first side of the first distal element and into the first target area, and in the second configuration of the first indicator, the first indicator extends from a second side of the first distal element opposite the first side; and a second indicator coupled with the second distal element to indicate a presence of the second leaflet in the second target area, wherein the second indicator is moveable from a first configuration to a second configuration by the presence of the second leaflet grasped within the second target area, wherein, in the first configuration of the second indicator, the second indicator extends from a first side of the second distal element and into the second target area, and in the second configuration of the second indicator, the second indicator extends from a second side of the second distal element opposite the first side of the second distal element.

13. The fixation device of claim 12, wherein the first and second indicators are biased toward their respective first configuration.

14. The fixation device of claim 12, wherein: the first distal element has a first inner surface and a first outer surface, the first inner surface at least partially defining the first target area, and the first outer surface being disposed opposite the first inner surface, wherein the first indicator is configured to pass through the first inner and outer surfaces when transitioning from the first configuration thereof to the second configuration thereof, and the second distal element has a second inner surface and a second outer surface, the second inner surface at least partially defining the second target area, and the second outer surface being disposed opposite the second inner surface, wherein the second indicator is configured to pass through the second inner and second surfaces when transitioning from the first configuration thereof to the second configuration thereof.

15. The fixation device of claim 14, wherein the first and second inner surfaces are each concavely shaped.

16. The fixation device of claim 14, wherein the first and second indicators each include a flexible loop.

17. The fixation device of claim 16, wherein the first and second indicators each include an enhanced visibility material viewable using a visualization technique.

* * * * *